(12) United States Patent
Bhuniya et al.

(10) Patent No.: US 7,365,064 B2
(45) Date of Patent: Apr. 29, 2008

(54) BENZOXAZINE AND BENZOTHIAZINE DERIVATIVES AND PHARMACEUTICAL COMPOSITIONS CONTAINING THEM

(75) Inventors: Debnath Bhuniya, Hyderabad (IN); Saibal Kumar Das, Hyderabad (IN); Gurram Ranga Madhavan, Hyderabad (IN); Javed Iqbal, Hyderabad (IN); Ranjan Chakrabarti, Hyderabad (IN)

(73) Assignees: Dr. Reddy's Laboratories Limited, Hyderabad (IN); Dr. Reddy's Laboratories, Inc., Bridgewater, NJ (US)

( * ) Notice: Subject to any disclaimer, the term of this patent is extended or adjusted under 35 U.S.C. 154(b) by 288 days.

(21) Appl. No.: 10/492,454

(22) PCT Filed: Oct. 15, 2002

(86) PCT No.: PCT/IB02/04275

§ 371 (c)(1),
(2), (4) Date: Dec. 17, 2004

(87) PCT Pub. No.: WO03/033481

PCT Pub. Date: Apr. 24, 2003

(65) Prior Publication Data

US 2005/0113368 A1    May 26, 2005

(30) Foreign Application Priority Data

Oct. 16, 2001  (IN)  .................... 848/MAS/2001

(51) Int. Cl.
*C07D 265/36*    (2006.01)
*C07D 279/16*    (2006.01)
*A61K 31/5415*   (2006.01)
*A61K 31/538*    (2006.01)

(52) U.S. Cl. .................... 514/230.5; 544/105
(58) Field of Classification Search ............... 544/105; 514/230.5
See application file for complete search history.

(56) References Cited

FOREIGN PATENT DOCUMENTS

| WO | 99/20614 | 4/1999 |
|----|----------|--------|
| WO | 00/66572 | 11/2000 |
| WO | 02/30914 | 4/2002 |

*Primary Examiner*—Kahsay T Habte
(74) *Attorney, Agent, or Firm*—Lee Banks; Robert A. Franks; Anjum Swaroop

(57) ABSTRACT

The present invention relates to novel antidiabetic, hypolipidemic, antiobesity and hypocholesterolemic compounds of formula (I) their derivatives, their analogs, their tautomeric forms, their stereoisomers, their polymorphs, their pharmaceutically acceptable salts, their pharmaceutically acceptable solvates and pharmaceutically acceptable compositions containing them, to a process for preparing such compounds. More particularly, the present invention relates to novel alkyl carboxylic acids of the general, their derivatives, their analogs, their tautomeric forms, their stereoisomers, their polymorphs, their pharmaceutically acceptable salts, their pharmaceutically acceptable solvates and pharmaceutically acceptable compositions containing them, to a process for preparing such compounds. The present invention also relates to processes for the preparation of the compounds of formula (I), novel intermediates, processes for their preparation, their use in the preparation of the above said compounds and their use as antidiabetic, hypolipidemic, antiobesity and hypocholesterolemic compounds

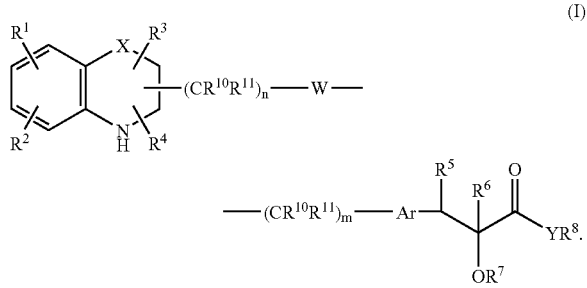

17 Claims, No Drawings

BENZOXAZINE AND BENZOTHIAZINE DERIVATIVES AND PHARMACEUTICAL COMPOSITIONS CONTAINING THEM

FIELD OF THE INVENTION

The present invention relates to novel antidiabetic, hypolipidemic, antiobesity and hypocholesterolemic compounds, their derivatives, their analogs, their tautomeric forms, their stereoisomers, their polymorphs, their pharmaceutically acceptable salts, their pharmaceutically acceptable solvates and pharmaceutically acceptable compositions containing them, to a process for preparing such compounds. More particularly, the present invention relates to novel alkyl carboxylic acids of the general, their derivatives, their analogs, their tautomeric forms, their stereoisomers, their polymorphs, their pharmaceutically acceptable salts, their pharmaceutically acceptable solvates and pharmaceutically acceptable compositions containing them, to a process for preparing such compounds.

The present invention also relates to novel intermediates, processes for their preparation, their use in the preparation of the above said compounds and their use as antidiabetic, hypolipidemic, antiobesity and hypocholesterolemic compounds.

The compounds of the present invention lower plasma glucose, triglycerides, lower total cholesterol (TC) and increase high-density lipoprotein (HDL) and decrease low density lipoprotein (LDL), which have a beneficial effect on coronary heart disease and atherosclerosis.

The compounds of the present invention are useful in reducing body weight and for the treatment and/or prophylaxis of diseases such as atherosclerosis, stroke, peripheral vascular diseases and related disorders. These compounds are useful for the treatment of hyperlipidemia, hyperglycemia, hypercholesterolemia, lowering of atherogenic lipoproteins, VLDL (very low density lipoprotein) and LDL. The compounds of the present invention can be used for the treatment of certain renal diseases including glomerulonephritis, glomerulosclerosis, nephrotic syndrome, hypertensive nephrosclerosis and nephropathy. The said compounds are also useful for the treatment and/or prophylaxis of leptin resistance, impaired glucose tolerance, disorders related to syndrome X such as hypertension, obesity, insulin resistance, coronary heart disease and other cardiovascular disorders. These compounds may also be useful as aldose reductase inhibitors, for improving cognitive functions in dementia, treating diabetic complications, disorders related to endothelial cell activation, psoriasis, polycystic ovarian syndrome (PCOS), inflammatory bowel diseases, osteoporosis, myotonic dystrophy, pancreatitis, arteriosclerosis, retinopathy, xanthoma, eating disorders, inflammation and for the treatment of cancer. The compounds of the present invention are also useful in the treatment and/or prophylaxis of the above said diseases in combination/concomittant with one or more HMG CoA reductase inhibitors, hypolipidemic/hypolipoproteinemic agents such as fibric acid derivatives, nicotinic acid, cholestyramine, colestipol and probucol; insulin, sulfonyl urea, metformin.

BACKGROUND OF THE INVENTION

Atherosclerosis and other peripheral vascular diseases effect the quality of life of millions of people. Therefore, considerable attention has been directed towards understanding the etiology of hypercholesterolemia and hyperlipidemia and development of effective therapeutic strategies.

Hypercholesterolemia has been defined as plasma cholesterol level that exceeds arbitrarily defined value called "normal" level. Recently, it has been accepted that "ideal" plasma levels of cholesterol are much below the "normal" level of cholesterol in the general population and the risk of coronary artery disease (CAD) increases as cholesterol level rises above the "optimum" (or "ideal") value. There is clearly a definite cause and effect-relationship between hypercholesterolemia and CAD, particularly for individuals with multiple risk factors. Most of the cholesterol is present in the esterified forms with various lipoproteins such as Low density lipoprotein (LDL), Intermediate density lipoprotein (IDL), High density lipoprotein (HDL) and partially as Very low density lipoprotein (VLDL). Studies clearly indicate that there is an inverse correlationship between CAD and atherosclerosis with serum HDL-cholesterol concentrations, (Stampfer et al, *N. Engl. J. Med.,* 325 (1991), 373-381) and the risk of CAD increases with increasing levels of LDL and VLDL.

In CAD, generally "fatty streaks" in carotid, coronary and cerebral arteries, are found which are primarily free and esterified cholesterol. Miller et al., (*Br. Med. J.,* 282 (1981), 1741-1744) have shown that increase in HDL-particles may decrease the number of sites of stenosis in coronary arteries of human, and high level of HDL-cholesterol may protect against the progression of atherosclerosis. Picardo et al, *arteriosclerosis* 6 (1986) 434-441 have shown by in vitro experiment that HDL is capable of removing cholesterol from cells. They suggest that HDL may deplete tissues of excess free cholesterol and transfer it to liver, which is known as reverse cholesterol transport, (Macikinnon et al., *J. Biol. chem.* 261 (1986), 2548-2552). Therefore, agents that increase HDL cholesterol would have therapeutic significance for the treatment of hypercholesterolemia and coronary heart diseases (CHD).

Obesity is a disease highly prevalent in affluent societies and in the developing world and is a major cause of morbidity and mortality. It is a state of excess body fat accumulation. The causes of obesity are unclear. It is believed to be of genetic origin or promoted by an interaction between the genotype and environment. Irrespective of the cause, the result is fat deposition due to imbalance between the energy intake versus energy expenditure. Dieting, exercise and appetite suppression have been a part of obesity treatment There is a need for efficient therapy to fight this disease since it may lead to coronary heart disease, diabetes, stroke, hyperlipidemia, gout, osteoarthritis, reduced fertility and many other psychological and social problems.

Diabetes and insulin resistance is yet another disease which severely effects the quality of large population in the world. Insulin resistance is the diminished ability of insulin to exert its biological action across a broad range of concentrations. In insulin resistance, the body secretes abnormally high amounts of insulin to compensate for this defect; failing which, the plasma glucose concentration inevitably raises and develops into diabetes. Among the developed countries, diabetes mellitus is a common problem and is associated with a variety of abnormalities including obesity, hypertension, hyperlipidemia (*J. Clin. Invest.,* 75 (1985) 809-817; *N. Engl. J. Med* 317 (1987) 350-357; *J. Clin. Endocrinol. Metab.,* 66 (1988) 580-583; *J. Clin. Invest.,* 68 (1975) 957-969) and other renal complications (patent publication No. WO 95/21608). It is now increasingly being recognized that insulin resistance and relative hyperinsulinemia have a contributory role in obesity, hypertension, atherosclerosis and type 2 diabetes mellitus. The association of insulin resistance with obesity, hypertension and angina has been described as a syndrome having insulin resistance as the central pathogenic link-Syndrome-X.

Hyperlipidemia is the primary cause for cardiovascular (CVD) and other peripheral vascular disease's. High risk of CVD is related to the higher LDL (Low Density Lipoprotein) and VLDL (Very Low Density Lipoprotein) seen in hyperlipidemia. Patients having glucose intolerance/insulin resistance in addition to hyperlipidemia have higher risk of CVD. Numerous studies in the past have shown that lowering of plasma triglycerides and total cholesterol, in particular LDL and VLDL and increasing HDL cholesterol help in preventing cardiovascular diseases.

Peroxisome proliferator acitivated receptors (PPAR) are members of the nuclear receptor super family. The gamma (γ) isoform of PPAR (PPARγ) has been implicated in regulating differentiation of adipocytes (*Endocrinology*, 135, (1994) 798-800) and energy homeostasis (*Cell*, 83 (1995) 803-812), whereas the alpha (α) isoform of PPAR (PPARα) mediates fatty acid oxidation (*Trend. Endocrin. Metab.*, 4 (1993) 291-296) thereby resulting in reduction of circulating free fatty acid in plasma (*Current Biol.* 5 (1995) 618-621). PPARα agonists have been found useful for the treatment of obesity (WO 97/36579). It has been recently disclosed that compounds which are agonists for both PPARα and PPARγ are suggested to be useful for the treatment of syndrome X (WO 97/25042). Similar effect between the insulin sensitizer (PPARγ agonist) and HMG CoA reductase inhibitor has been observed which may be useful for the treatment of atherosclerosis and xanthoma (EP 0 753 298).

It is known that PPARγ plays an important role in adipocyte differentiation (*Cell*, 87 (1996) 377-389). Ligand activation of PPAR is sufficient to cause complete terminal differentiation (*Cell*, 79 (1994) 1147-1156) including cell cycle withdrawal. PPARγ is consistently expressed in certain cells and activation of this nuclear receptor with PPARγ agonists would stimulate the terminal differentiation of adipocyte precursors and cause morphological and molecular changes characteristics of a more differentiated, less malignant state (*Molecular Cell*, (1998), 465-470; *Carcinogenesis*, (1998), 1949-53; *Proc. Natl. Acad. Sci.*, 94 (1997) 237-241) and inhibition of expression of prostate cancer tissue (*Cancer Research* 58 (1998) 3344-3352). This would be useful in the treatment of certain types of cancer, which express PPARγ and could lead to a quite nontoxic chemotherapy.

Leptin resistance is a condition wherein the target cells are unable to respond to leptin signal. This may give rise to obesity due to excess food intake and reduced energy expenditure and cause impaired glucose tolerance, type 2 diabetes, cardiovascular diseases and such other interrelated complications. Kallen et al (*Proc. Natl. Acad. Sci.* (1996) 93, 5793-5796) have reported that insulin sensitizers which perhaps due to the PPAR agonist expression lower plasma leptin concentrations. However, it has been recently disclosed that compounds having insulin sensitizing property also possess leptin sensitization activity. They lower the, circulating plasma leptin concentrations by improving the target cell response to leptin (WO 98/02159).

PRIOR ART

A few alkyl carboxylic acids, their derivatives and their analogs have been reported to be useful in the treatment of hyperglydemia and hypercholesterolemia. Some of such compounds described in the prior art are outlined below:

i). In our international publication No. WO 99/08501 we have disclosed the compounds of general formula (IIa)

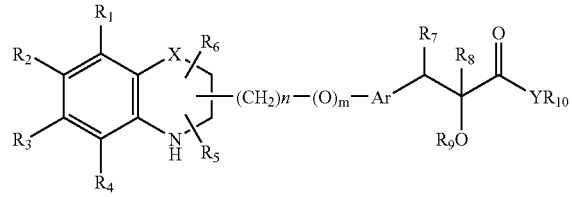

(IIa)

wherein the groups $R^1$, $R^2$, $R^3$, $R^4$ and the groups $R^5$ and $R^6$ when attached to carbon atom, nay be same or different and represent hydrogen, halogen, hydroxy, nitro, cyano, formyl or unsubstituted or substituted groups selected from alkyl, cycloalkyl, alkoxy, cycloalkoxy, aryl, aryloxy, aralkyl, aralkoxy, heterocyclyl, heteroaryl, heteroaralkyl, heteroaryloxy, heteroaralkoxy, acyl, acyloxy, amino, acylamino, monoalkylamino, dialkylamino, arylamino, aralkylamino, alkoxycarbonyl, aryloxycarbonyl, aralkoxycarbonyl, alkylthio, alkoxycarbonylamino, aryloxycarbonylamino, aralkoxycarbonylamino, carboxylic acid or its derivatives, or sulfonic acid or its derivatives; one or both of $R^5$ and $R^6$ may also represent at oxo group when they are attached to carbon atom; $R^5$ and $R^6$ when attached to nitrogen atom represent hydrogen, hydroxy, formyl or unsubstituted or substituted groups selected from alkyl, cycloalkyl, alkoxy, cycloalkoxy, aryl, aralkyl, heterocyclyl, heteroaryl, heteroaralkyl, acyl, acyloxy, amino, acylamino, monoalkylamino, dialkylamino, arylamino, aralkylamino, aryloxy, aralkoxy, heteroaryloxy, heteroaralkoxy, alkoxycarbonyl, aryloxycarbonyl, aralkoxycarbonyl, alkylthio, carboxylic acid derivatives, or sulfonic acid derivatives; X represents a heteroatom selected from oxygen, sulfur, or $NR^{11}$ where $R^{11}$ represents hydrogen or unsubstituted or substituted groups selected from alkyl, cycloalkyl, aryl, aralkyl, acyl, alkoxycarbonyl, ayloxycarbonyl or aralkoxycarbonyl groups; Ar represents unsubstituted or substituted divalent single or fused aromatic or heterocyclic group; $R^7$ represents hydrogen atom, hydroxy, alkoxy, halogen, lower alkyl, unsubstituted or substituted aralkyl group or forms a bond together with the adjacent group $R^8$; $R^8$ represents hydrogen, hydroxy, alkoxy, halogen, lower alkyl group, acyl, unsubstituted or substituted aralkyl or $R^8$ forms a bond together with $R^7$; $R^9$ represents hydrogen, unsubstituted or substituted groups selected from alkyl, cycloalkyl, aryl, aralkyl, alkoxycarbonyl, aryloxycarbonyl, alkylaminocarbonyl, arylaminocarbonyl, acyl, heterocyclyl, heteroaryl or heteroaralkyl groups; $R^{10}$ represents hydrogen, unsubstituted or substituted groups selected from alkyl, cycloalkyl, aryl, aralkyl, alkoxycarbonyl, aryloxycarbonyl, alkylaminocarbonyl, arylaminocarbonyl, acyl, heterocyclyl, heteroaryl or heteroaralkyl groups; Y represents oxygen or $NR^{12}$, where $R^{12}$ represents hydrogen, alkyl, aryl, hydroxyalkyl, aralkyl, heterocyclyl, heteroaryl, heteroaralkyl groups; $R^{10}$ and $R^{12}$ together may form a 5 or 6 membered cyclic structure containing carbon atoms, at least one nitrogen atom and which may optionally contain one or more additional heteroatoms selected from oxygen, sulfur or nitrogen; the linking group represented by —$(CH2)_n$-$(O)_m$— may be attached either through a nitrogen atom or a carbon atom; n is an integer ranging from 1-4 and m is an integer 0 or 1.

An example of these compounds is shown in formula (IIb)

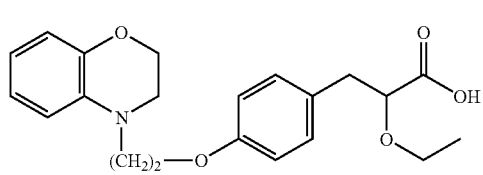

ii) International publication No. WO 00/64888 disclose the compounds of general formula (IIc)

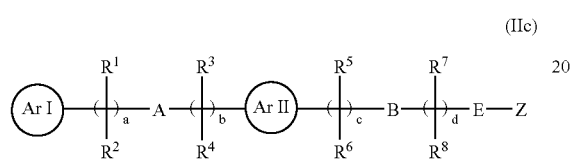

wherein $Ar^1$ and $Ar^2$ are independently aryl, fused arylcycloalkenyl, fused arylcycloalkyl, fused arylheterocyclenyl, fused arylheterocyclyl, heteroaryl, fused heteroarylcycloalkenyl, fused heteroarylcycloalkyl, fused heteroarylcyclenyl or fused heteroarylheterocyclyl; A is O, S, SO, $SO_2$, $NR^{13}$, C(O), $NR^{14}C(O)$, $C(O)NR^{14}$, $NR^{14}C(O)N(R^{15})$, $C(R^{14})=N$; chemical bond and the like; B is O, S, $NR^{19}$, a chemical bond, C(O), $N(R^{20})C(O)$ or $C(O)N(R^{20})$; E is a chemical bond or an ethylene group; a is 0-6; b is 0-4; c is 0-4; d is 0-6; g is 1-5; h is 1-4; $R^1$, $R^3$, $R^5$ and $R^7$ are independently hydrogen, halogen, alkyl, carbonyl, alkoxycarbonyl, or aralkyl; $R^2$, $R^4$, $R^6$ and $R^8$ are independently $-(CH_2)_q-X$; q is 0-3; X is hydrogen, halogen, alkyl, alkenyl, cycloalkyl, heterocyclyl, aryl, heteroaryl, aralkyl, heteroaralkyl, hydroxy, alkoxy, aralkoxy, heteroaralkoxy, carbonyl, alkoxycarbonyl, tetrazolyl, acyl, $acylHNSO_2$, and the like; Z is $R^{21}O_2C$, $R^{21}OC$, cyclo-imide; CN, $R^{21}O_2SHNCO$, $R^{21}O_2SNH$, $R^{21}NCO$, $R^{21}O$-2,4-thiazolidmonyl or tetrazolyl.

An example of these compounds is shown in formula (IId)

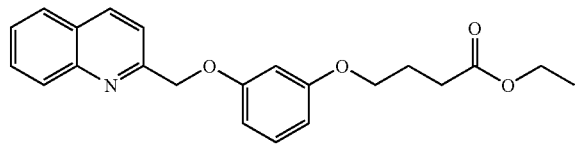

iii) International publication Nos. WO 95/03038 and WO 96/04260 disclose compounds of formula (II e)

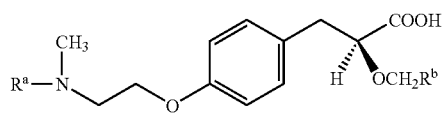

wherein $R^a$ represents 2-benzoxazolyl or 2-pyridyl and $R^b$ represent $CF_3$, $CH_2OCH_3$ or $CH_3$. A typical example is (S)-3-[4-[2-[N-(2-benzoxazolyl)N-methylamino]ethoxy]phenyl]-2-(2,2,2-trifluoroethoxy)propanoic acid (II f).

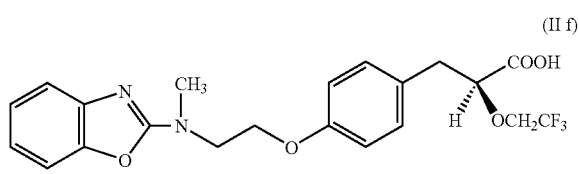

iv) International publication Nos. WO 94/13650, WO 94/01420 and WO 95/17394 disclose the compounds of general formula (II g)

$$A^1\text{-}X\text{-}(CH_2)_n\text{-}O\text{-}A^2\text{-}A^3\text{-}Y.R^2 \qquad (II\ g)$$

wherein $A^1$ represent aromatic heterocycle, $A^2$ represents substituted benzene ring and $A^3$ represents moiety of formula $(CH_2)_m-CH-(OR^1)$, wherein $R^1$ represents alkyl groups, m is an integer of 1-5; X represents substituted or unsubstituted N; Y represents C=O or C=S, $R^2$ represents $OR^3$ where $R^3$ may be hydrogen, alkyl, aralkyl, or aryl group and n is at integer of 2-6.

An example of these compounds is shown in formula (II h)

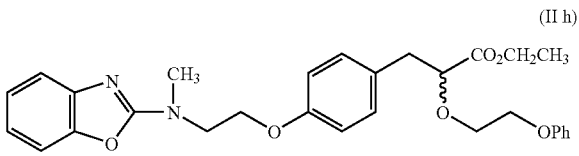

v) International publication No. WO 00/49005 disclose the compounds of general formula (II i)

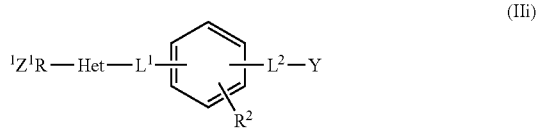

wherein Het is an optionally substituted, saturated partially saturated or fully unsaturated 8 to 10 membered bicyclic ring, $R^1$ is optionally substituted aryl or optionally substituted heteroaryl, $R^2$ is hydrogen halogen, lower alkyl or lower alkoxy, $L^1$ is an $-R^3-R^4$ linkage where $R^3$ is alkylene, alkenylene or alkynylene and $R^4$ is a direct bond, cycloalkylene, heterocycloalkylene, arylene; heteroarylidinyl, $-C(=Z^2)\text{-}NR^5$, $NR^5\text{-}C(=Z^2)$, $-Z^2$-, $-C(=O)$, $-C(=NOR^5)-$, $-NR^5-$, $NR^5-C(=Z^2)$-$NR^5$, $SO_2-NR^5$ $NR^5-SO_2$, $-O-C(=O)$, $-C(=O)-O$, $-O-C(=O)-NR^5$, $-NR^5-C(=O)-O-$; $L^2$ is optionally substituted alkylene or alkenylene, Y is carboxy or an acid bioisostere and $Z^1$ is $NR^5$ and the corresponding N-oxides and their prodrugs and pharmaceutically acceptable salts and solvates.

An example of these compounds is shown in formula (II j)

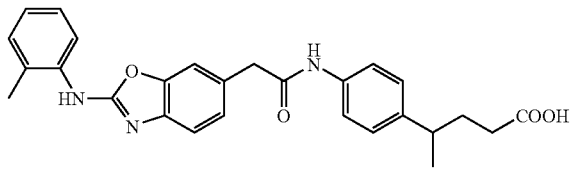

(ii j)

vi) International publication No. WO 94/12181 disclose the compounds of general formula (II k)

X—Y-Z-Aryl-A-B   (II k)

aryl is a 6 membered aromatic ring containing 0, 1, 2 or 3 nitrogen atoms and either unsubstituted or substituted with $R^8$ and $R^9$; X represents $NH_2$, NH—C(=NH)—, and the like or 4 to 10 membered mono or polycyclic aromatic or nonaromatic ring system and containing 0, 1, 2, 3 or 4 heteroatoms selected from N, O or S either unsubstituted or substituted; Y is selected from $C_{0-8}$ alkyl, $C_{4-10}$ cycloalkyl, $C_{0-8}$ alkyl-$NR^3$—CO—$C_{0-8}$ alkyl, $C_{0-8}$alkyl-$CONR^3$—$C_{0-8}$ alkyl, $C_{0-8}$ alkyl-O—$C_{0-8}$ alkyl, $C_{0-8}$ alkyl-$S(O)_n$—$C_{0-8}$ alkyl, $(CH_2)_{0-8}$ aryl-$(CH_2)_{0-8}$, $(CH_2)_{0-6}$ aryl-$SO_n$—, $(CH_2)_{0-8}$ aryl-CO—$(CH_2)_{0-8}$, $(CH_2)_{0-6}$ aryl-$SO_2$—$(CH_2)_{0-6}$—, $(CH_2)_{0-6}$ $NR^3$—$(CH_2)_{0-6}$—, $(CH_2)_{0-6}$ aryl-CH(OH)—$(CH_2)_{0-6}$—, $(CH_2)_{0-8}$—CONH—$(CH_2)_{0-8}$—, $C_{0-8}$ alkyl-$SO_2$—$NR^3$—$C_{0-8}$ alkyl, $C_{0-8}$ alkyl-CO—$C_{0-8}$ alkyl, $C_{0-8}$ alkyl-CH(OH)—$C_{0-8}$ alkyl, where n is an integer from 0-2; Z and A are independently chosen from $(CH_2)_m$, $(CH_2)_mO(CH_2)_n$, $(CH_2)_mNR^3(C_2)_n$, $(CH_2)_mNR^3(CH_2)_n$, $(CH_2)_mCONR^{11}(CH_2)_n$, $(CH_2)_mCO(CH_2)_n$, $(CH_2)_mCS(CH_2)_n$, $(CH_2)_mSO_2(CH_2)_n$, $(CH_2)_mS(CH_2)_n$, $(CH_2)_mSO_2(CH_2)_n$, $(CH_2)_mSO(CH_2)_n$, $(CH_2)_mSO_2NR^3(CH_2)_n$, $(CH_2)_mNR^3SO_2(CH_2)_n$, $(CH_2)_mCR^3=CR^4(CH_2)_n$, $(CH_2)_mC\equiv C(CH_2)_n$, $(CH_2)_mCH(OH)(CH_2)_n$; where m and n are each independently an integer from 0 to 6; Aryl is a 6 membered aromatic ring system containing 0, 1, 2, 3 or 4 N atoms and either unsubstituted or substituted with $R^5$, provided that when A is $(CH_2)_m$, the Aryl ring, bonded by Z and A must contain at least one heteroatom;

B is

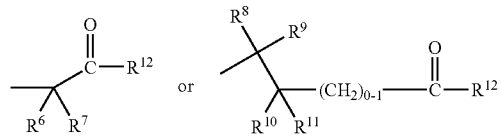

$R^6$, $R^7$, $R^8$, $R^9$, $R^{10}$ and $R^{11}$, are independently selected from hydrogen, fluorine, $(C_{1-8})$ alkyl, hydroxy, hydroxy $(C_{1-6})$ alkyl, carboxy$(C_{0-6})$alkyl, $(C_{1-6})$alkyloxy, aryl $(C_{0-6})$alkyloxy, $(C_{3-8})$cycloalkyl, aryl$(C_{0-6})$alkyl, $(C_{1-6})$ alkylcarbonyloxy, $(C_{0-6})$alkylamino$(C_{0-6})$alkyl and the like; $R^{12}$ is selected from hydroxy, $(C_{1-8})$ alkyloxy, aryl $(C_{0-6})$ alkyl and the like;

An example of these compounds is shown in formula (II l)

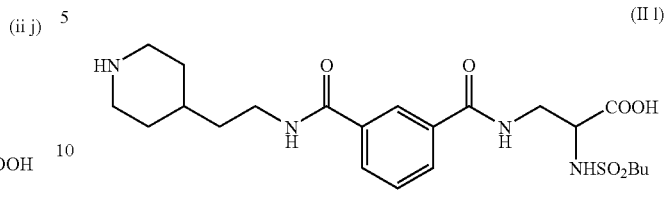

(II l)

vii) International publication No. WO 93/16697 and U.S. Pat. No. 5,227,490 disclose the compounds of general formula (II m)

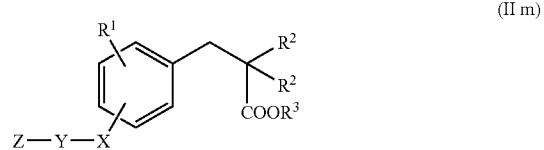

(II m)

$R^1$ is chosen from hydrogen, $C_{1-6}$ alkyl, aryl $C_{4-10}$ alkyl, aryl, carboxy, $C_{1-6}$ alkyloxy, carboxy $C_{0-6}$ alkyl, carboxy $C_{1-6}$ alkyloxy, hydroxy $C_{0-6}$ alkyl, $C_{1-4}$ alkylsulfonyl $C_{0-6}$ alkyl, $C_{0-4}$ alkylamino $C_{0-6}$ alkyl, aryl $C_{0-10}$ alkylamino $C_{0-6}$ alkyl, $C_{2-10}$ acylamino $C_{0-6}$ alkyl, $C_{1-4}$ carboalkoxy $C_{0-6}$ alkyl halogen, $R^2$ is independently chosen from hydrogen, halogen, hydroxy, $C_{1-6}$ alkyl, wherein the alkyl group is substituted or unsubstituted, $C_{1-6}$alkyloxy, aryl $C_{0-4}$ alkyl, aryl $C_{0-6}$ alkyloxy and the like; $R^3$ hydrogen, $C_{1-6}$ alkyl, aryl $C_{1-10}$ alkyl; Z is $NR_4R^5$ or a 4-9 membered mono or bicyclic ring system containing 1, 2 or 3 heteroatoms selected from N, O or S and either unsubstituted or substituted; Y is $C_{1-6}$ alkyl either unsubstituted or substituted, $C_{4-8}$ cycloalkyl, aryl, —C(=O)NH—, —NH(C=O)— and the like; X is O, SO, $SO_2$, S, CO, —$NR^4CO$—, $CONR^4$—, $CH_2$ and the like;

An example of these compounds is shown in formula (II n)

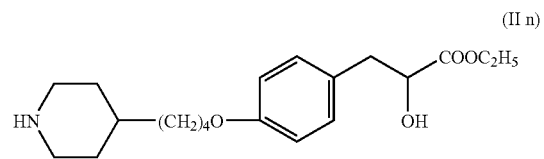

(II n)

Few β-phenyl α-hydroxysubstituted propionic acid derivatives have been reported which have been used as intermediates for the synthesis of target molecules. Some of such compounds described in the prior art are outlined below:

i) European Patent Application EP0816316 discloses compound of formula (IIo)

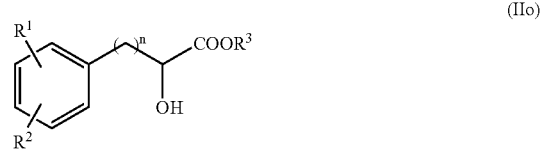

(IIo)

The compound of formula (va) was further converted to 1,2-ethainediaol derivative of the formula (IIp):

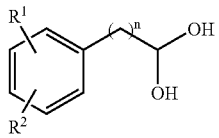
(IIp)

These 1,2-ethanediaol derivatives are useful intermediates for the pharmaceuticals and agricultural chemicals.
ii) Japanese Patent Application JP 10017540 discloses compound of formula (IIq)

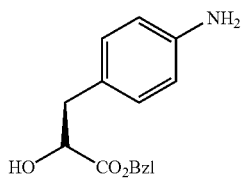
(IIq)

The compound of formula (IIr) was further converted to a compound of formula (vd)

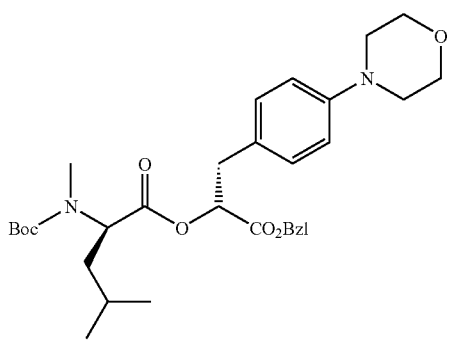
(IIr)

SUMMARY OF THE INVENTION

With an objective to develop novel compounds for the treatment and/or prophylaxis of diseases related to increased levels of lipids, especially to treat hypertriglyceridemia and to lower free fatty acids, for the treatment and/or prophylaxis of diseases described as Syndrome-X which include hyperlipidemia, hyperinsulinemia, obesity, insulin resistance, insulin resistance leading to type 2 diabetes and diabetes complications thereof, for the treatment of diseases wherein insulin resistance is the pathophysiological mechanism, for the treatment of hypertension, atherosclerosis and coronary artery diseases with better efficacy, potency and lower toxicity, we focused our research to develop new compounds effective in the treatment of above mentioned diseases.

The main objective of the present invention is therefore, to provide novel β-aryl-α-oxysubstituted alkylcarboxylic acids and their derivatives, their analogs, their tautomeric forms, their stereoisomers, their polymorphs, their pharmaceutically acceptable salts, their pharmaceutically acceptable solvates and pharmaceutical compositions containing them, or their mixtures.

Another objective of the present invention is to provide novel β-aryl-α-oxysubstituted alkyl carboxylic acids, their derivatives, their analogs, their tautomeric forms, their stereoisomers, their polymorphs, their pharmaceutically acceptable salts, their pharmaceutically acceptable solvates and pharmaceutical compositions containing them or their mixtures which may have agonist activity against PPARα and/or PPARγ, and optionally inhibit HMG CoA reductase, in addition to agonist activity against PPARα and/or PPARγ.

Another objective of the present invention is to provide novel β-aryl-α-oxysubstituted alkyl carboxylic acids and their derivatives, their analogs, their tautomeric forms, their stereoisomers, their polymorphs, their pharmaceutically acceptable salts, their pharmaceutically acceptable solvates and pharmaceutical compositions containing them or their mixtures having enhanced activities, without toxic effect or with reduced toxic effect.

Yet another objective of the present invention is to provide a process for the preparation of β-aryl-α-oxysubstituted alkyl carboxylic acids, their derivatives, their analogs, their tautomeric forms, their stereoisomers, their polymorphs, their pharmaceutically acceptable salts and their pharmaceutically acceptable solvates.

Still another objective of the present invention is to provide pharmaceutical compositions of β-aryl-α-oxysubstituted alkyl carboxylic acids, their analogs, their derivatives, their tautomers, their polymorphs, their salts, solvates or their mixtures in combination with suitable carriers, solvents, diluents and other media normally employed in preparing such compositions.

Another objective of the present invention is to provide novel intermediates, a process for their preparation and use of the intermediates in process for preparation of β-aryl-α-oxysubstituted alkoxy carboxylic acids, their derivatives, their analogs their tautomers, their stereoisomers, their polymorphs, their salts and their pharmaceutically acceptable solvates and their use as antidiabetic, hypolipdemic, antiobesity and hypocholesterolemic compounds.

DETAILED DESCRIPTION OF THE INVENTION

β-Aryl-α-oxysubstituted propionoic acids of the present invention having the general formula (I)

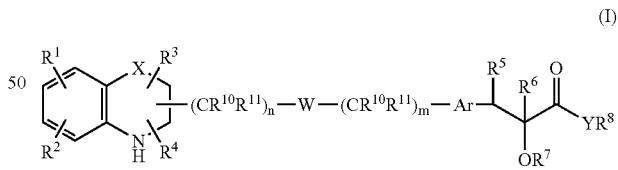
(I)

their derivatives, their analogs, their tautomeric forms, their stereoisomers, their polymorphs, their pharmaceutically acceptable salts, their pharmaceutically acceptable solvates wherein $R^1$, $R^2$ and $R^3$, $R^4$ when attached to the carbon atom, may be same or different and represent hydrogen, halogen, hydroxy, nitro, cyano, formyl or substituted or unsubstituted groups selected from alkyl, cycloalkyl, alkoxy, cycloalkoxy, aryl, aryloxy, aralkyl, aralkoxy, heterocyclyl, heteroaryl, heteroaralkyl, heteroaryloxy, heteroaralkoxy, acyl, acyloxy, hydroxyalkyl, amino, acylamino, monoalkylamino, dialkylamino, arylamino, aralkylamino, alkoxycarbonyl, aryloxycarbonyl, aralkoxycarbonyl, alkoxyalkyl, aryloxyalkyl, aralkoxyalkyl, alkylthio, thioalkyl, alkoxycarbonylamino, aryloxycarbonylamino, aralkoxycarbonylamino, carboxylic acid or its derivatives, or sulfonic acid or its derivatives; one or both of $R^3$ and $R^4$ may represent oxo or thioxo group when they are attached to carbon atom; $R^3$ and $R^4$ when attached to nitrogen atom represent hydrogen, hydroxy, formyl or substituted or unsubstituted groups selected from alkyl, cycloalkyl, alkoxy, cycloalkoxy, aryl, aralkyl, heterocyclyl, heteroaryl, heteroaralkyl, acyl, acyloxy, hydroxyalkyl, amino, acylamino, monoalkylamino, dialkylamino, arylamino, aralkylamino, aminoalkyl, aryloxy, aralkoxy, heteroaryloxy, heteroaralkoxy, alkoxycarbonyl, aryloxycarbonyl, aralkoxycarbonyl, alkoxyalkyl, aryloxyalkyl, aralkoxyalkyl, alkylthio, thioalkyl groups, carboxylic acid derivatives, or sulfonic acid derivatives; X represents a heteroatom selected from oxygen or sulfur; W represents $NR^{12}$, —C(=O)—$(CR^{10}R^{11})_o$—$NR^{12}$, —O-aryl-$(CR^{10}R^{11})_o$—$NR^{12}$, where $R^{12}$ represents hydrogen or substituted or unsubstituted group selected from alkyl, aryl or aralkyl groups; o is an integer ranging from 0-6; $R^{10}$ and $R^{11}$ may be same or different and represent hydrogen or unsubstituted or substituted group selected form alkyl, alkoxyl, aryl or aralkyl group; Ar represents substituted or unsubstituted diavlent single or fused aromatic or heterocyclic group; $R^5$ represents hydrogen atom, hydroxy, alkoxy, halogen, alkyl, substituted or unsubstituted aralkyl group or forms a bond together with the adjacent group $R^6$; $R^6$ represents hydrogen, hydroxy, alkoxy, halogen, alkyl group, acyl, substituted or substituted aralkyl or $R^6$ forms a bond together with $R^5$; $R^7$ may be hydrogen or substituted or unsubstituted groups selected from alkyl, cycloalkyl, aryl, aralkyl, alkoxyalkyl, alkoxycarbonyl, aryloxycarbonyl, alkylaminocarbonyl, aryl, arylaminocarbonyl, acyl, heterocyclyl, heteroaryl, heteroaralkyl groups, $R^8$ may be hydrogen or substituted or unsubstituted groups selected from alkyl, cycloalkyl, aryl, aralkyl, heterocyclyl, heteroaryl or heteroaralkyl groups; Y represents oxygen, sulfur or $NR^9$, where $R^9$ represents hydrogen or substituted or unsubstituted groups selected from alkyl, aryl, hydroxyalkyl, aralkyl heterocyclyl, heteroaryl, or heteroaralkyl groups or $NR^9$ represents chiral amine, chiral amine alcohols derived from chiral amino acid; $R^8$ and $R^9$ together may form a substituted or unsubstituted 5 or 6 membered cyclic structure containing carbon atoms, which may optionally contain one or more heteroatoms selected from oxygen, sulfur or nitrogen m and n are integers ranging from 0-6.

Suitable groups represented by $R^1$, $R^2$, $R^3$, $R^4$, may be selected from hydrogen, halogen atom such as fluorine, chlorine, bromine or iodine; hydroxy, cyano, nitro, formyl, substituted or unsubstituted $(C_1-C_{12})$ alkyl group especially linear or branched $(C_1-C_{10})$ alkyl group such as methyl, ethyl, n-propyl, iso-propyl, n-butyl, iso-butyl, t-butyl, n-pentyl, iso-pentyl, hexyl, heptyl, octyl and, the like; cyclo($C_3$-$C_6$)alkyl group such as cyclopropyl, cyclobutyl, cyclopentyl, cyclohexyl and the like, the cycloalkyl group may be substituted; $(C_1-C_6)$alkoxy such as methoxy, ethoxy, propyloxy, butyloxy, iso-propyloxy and the like, which may be substituted; cyclo($C_3$-$C_6$)alkoxy group such as cyclopropyloxy, cyclobutyloxy, cyclopentyloxy, cyclohexyloxy and the like, the cycloalkoxy group may be substituted; aryl group such as phenyl, naphthyl and the like, the aryl group may be substituted; aryloxy group such as phenoxy, naphthyloxy and the like, the aryloxy group may be substituted; aralkyl such as benzyl, phenethyl, $C_6H_5CH_2CH_2CH_2$, naphthylmethyl and the like, the aralkyl group may be substituted; aralkoxy group such as benzyloxy, phenethyloxy, naphthylmethyloxy, phenylpropyloxy and the like, the aralkoxy group may be substituted; heterocyclyl groups such as aziridinyl, pyrrolidinyl, morpholinyl, piperidinyl, piperazinyl and the like, the heterocyclyl group may be substituted; heteroaryl group such as pyridyl, thienyl, furyl, pyrrolyl, oxazolyl, thiazolyl, imidazolyl, oxadiazolyl, tetrazolyl, benzopyranyl, benzofuryl and the like, the heteroaryl group may be substituted; heteroaralkyl group such as furanmethyl, pyridinemethyl, oxazolemethyl, oxazolethyl and the like, the heteroaralkyl group may be substituted; heteroaryloxy and heteroaralkoxy, wherein heteroaryl and heteroaralkyl moieties are as defined earlier and may be substituted; acyl group such as acetyl, propionyl, benzoyl and the like, the acyl group may be substituted; acyloxy group such as OOCMe, OOCEt, OOCPh and the like, which may be substituted, acylamino groups such as $NHCOCH_3$, $NHCOC_2H_5$, $NHCOC_3H_7$, $NHCOC_6H_5$ and the like, which may be substituted; monoalkylamino group such as —$NHCH_3$, $NHC_2H_5$, $NHC_3H_7$, $NHC_6H_{13}$, and the like, which may be substituted; dialkylamino group such as $N(CH_3)_2$, $NCH_3(C_2H_5)$, $N(C_2H_5)_2$ and the like, which may be substituted; arylamino group such as $HNC_6H_5$, $NCH_3$ $(C_6H_5)$, $NHC_6H_4CH_3$, $NHC_6H_4$-Hal and the like, which may be substituted; aralkylamino group such as $C_6H_5CH_2NH$, $C_6H_5CH_2CH_2NH$, $C_6H_5CH_2NCH_3$ and the like, which may be substituted; amino group; alkoxycarbonyl such as methoxycarbonyl, ethoxycarbonyl and the like, which may be substituted; aryloxycarbonyl group such as phenoxycarbonyl, naphthyloxycarbonyl and the like, the aryloxycarbonyl group may be substituted; aralkoxycarbonyl group such as benzyloxycarbonyl, phenethyloxycarbonyl, naphthylmethoxycarbonyl and the like, which may be substituted; alkoxyalkyl group such as methoxymethyl, ethoxymethyl, methoxyethyl, ethoxyethyl and the like, the alkoxyalkyl group may be substituted; aryloxyalkyl group such as $C_6H_5OCH_2$, $C_6H_5OCH_2CH_2$, naphthyloxymethyl and the like, which may be substituted; aralkoxyalkyl group such as $C_6H_5CH_2OCH_2$, $C_6H_5CH_2OCH_2CH_2$ and the like, which may be substituted; hydroxy$(C_1-C_6)$alkyl, which may be substituted; thio $(C_1-C_6)$alkyl, which may be substituted; $(C_1-C_6)$alkylthio which may be substituted; alkoxycarbonylamino group such as $NHCOOC_2H_5$, $NHCOOCH_3$ and the like, which may be substituted; aryloxycarbonylamino group such as $NHCOOC_6H_5$, $NCH_3COOC_6H_5$, $NC_2H_5COOC_6H_5$, $NHCOOC_6H_4CH_3$, $NHCOOC_6H_4OCH_3$ and the like, which may be substituted; aralkoxycarbonylamino group such as $NHCOOCH_2C_6H_5$, $NHCOOC_2CH_2C_6H_5$, $N(CH_3)COOCH_2C_6H_5$, $N(C_2H_5)COOCH_2C_6H_5$, $NHCOOCH_2C_6H_4CH_3$, $NHCOOCH_2C_6H_4OCH_3$ and the like, which may be substituted; carboxylic acid or its derivatives such as amides, like $CONH_2$, CONHMe, $CONMe_2$, CONHEt, $CONEt_2$, CONHPh, and the like, the carboxylic acid derivatives may be substituted; sulfonic acid or its derivatives such as $SO_2NH_2$, $SO_2NHMe$, $SO_2NMe_2$, $SO_2NHCF_3$ and the like, the sulfonic acid derivatives may be substituted.

When the groups represented by $R^1$ to $R^4$ are substituted, the substituents may be selected from halogen, hydroxy, nitro, nitro or unsubstituted or substituted groups selected from alkyl, cycloalkyl, alkoxy, cycloalkoxy, aryl, aralkyl, aryloxy, aralkoxy, alkoxyalkyl, aryloxyalkyl, aralkoxyalkyl, heterocyclyl, heteroaryl, heteroaralkyl, acyl, acyloxy, hydroxyalkyl, amino, acylamino, arylamino aminoalkyl, alkoxycarbonyl, alkylamino, alkylthio groups, carboxylic acids or its derivatives or sulfonic acid or its derivatives. These groups are as defined above.

It is preferred that the substituents on $R^1$ to $R^4$ represent halogen atom such as fluorine, chlorine or bromine; alkyl group such as methyl, ethyl, iso-propyl, n-propyl, n-butyl; cycloalkyl group such as cyclopropyl; aryl group such as phenyl; aralkyl group such as benzyl; $(C_1-C_3)$alkoxy, benzyloxy, hydroxy, acyl or acyloxy groups.

Suitable groups represented by X may be selected from oxygen or sulfur.

Suitable groups represented by Ar may be selected from substituted or unsubstituted groups selected from divalent phenylene, naphthylene, pyrrol, pyridyl, quinolinyl, benzofuryl, dihydrobenzofuryl, benzopyranyl, dihydrobenzopyranyl, indolyl, indolinyl, azaindolyl, azaindolyl, pyrazolyl, benzothiazolyl, benzoxazolyl and the like. The substituents on the group represented by Ar amy may be selected from linear or branched optionally halogenated $(C_1-C_6)$alkyl, optionally halogenated $(C_1-C_3)$alkoxy, halogen, acyl, amino, acylamino, thio or carboxylic or sulfonic acids and their derivatives. The substituents are defined as they are for $R^1$—$R^4$.

It is more preferred that Ar represent substituted or unsubstituted divalent, phenylene, naphthylene, benzofuryl, indolyl, indolinyl, quinolinyl, azaindolyl, azaindolinyl, benzothiazolyl or benzoxazolyl groups.

Suitable groups represented by $R^5$ may be selected from hydrogen, hydroxy, $(C_1-C_6)$ alkyl groups such as methyl, ethyl, propyl and the like; $(C_1-C_3)$alkoxy group such as methoxy, ethoxy, propoxy and the like; halogen atom such as fluorine, chlorine, bromine or iodine; aralkyl such as benzyl, phenethyl and the like, which may be unsubstituted or substituted or $R^5$ together with $R^6$ represents a bond. The substituents are selected from halogen, hydroxy or alkyl groups.

Suitable $R^6$ may be hydrogen, hydroxy, $(C_1-C_6)$alkyl groups such as methyl, ethyl, propyl and the like; $(C_1-C_3)$ alkoxy such as methoxy, ethoxy, propoxy and the like; halogen atom such as fluorine, chlorine, bromine or iodine; $(C_2-C_{10})$acyl group such as acetyl, propanoyl butanoyl, pentanoyl, benzoyl and the like; aralkyl such as benzyl, phenethyl and the like, which may be unsubstituted or substituted or $R^6$ together with $R^5$ forms a bond. The substituents are selected from halogen, hydroxy or alkyl groups.

Suitable groups represented by $R^7$ may be selected from hydrogen, linear or branched $(C_1-C_{16})$alkyl, preferably $(C_1-C_{12})$alkyl group such as methyl ethyl, n-propyl, iso-propyl, n-butyl iso-butyl, pentyl, hexyl, octyl and the like, the alkyl group may be substituted; $(C_3-C_7)$cycloalkyl group such as cyclopropyl, cyclobutyl, cyclopentyl, cyclohexyl and the like, the cycloalkyl group may be substituted; aryl group such as phenyl, naphthyl and the like, the aryl group may be substituted; aralkyl group such as benzyl, phenethyl and the like, wherein the alkyl moiety may contain $(C_1-C_6)$ atoms, wherein the aryl moiety may be substituted; heteroaryl group such as pyridyl, thienyl, pyrrolyl, furyl and the like, the heteroaryl group may be substituted; heteroaralkyl group such as furanmethyl, pyridinemethyl, oxazolemethyl, oxazolethyl and the like, the heteroaralkyl group may be substituted; heterocyclyl group such as aziridinyl, pyrrolidinyl piperidinyl and the like, the heterocyclyl group may be substituted; linear or branched $(C_2-C_6)$acyl group such as acetyl, propanoyl, butanoyl, benzoyl, octanoyl, decanoyl and the like, which may be substituted; $(C_1-C_6)$alkoxycarbonyl group such as methoxycarbonyl, ethoxycarbonyl and the like, the alkoxycarbonyl group may be substituted; aryloxycarbonyl such as phenoxycarbonyl, naphthyloxycarbonyl and the like, the aryl group may be substituted; $(C_1-C_6)$alkylaminocarbonyl, the alkyl group may be substituted; arylaminocarbonyl such as PhNHCO, naphthylaminocarbonyl and the like, the aryl moiety may be substituted. The substituents may be selected from halogen, hydroxy, nitro or unsubstituted or substituted groups selected from alkyl, cycloalkyl, alkoxy, cycloalkoxy, aryl, aralkyl, aralkoxyalkyl, heterocyclyl, heteroaryl, heteroaralkyl, acyl, acyloxy, hydroxyalkyl, amino, acylamino, arylamino, aminoalkyl, aryloxy, aralkoxy, alkoxycarbonyl, alkylamino, alkoxyalkyl, aryloxyalkyl, alkylthio, thioalkyl groups, carboxylic acid or its derivatives or sulfonic acid or its derivatives. The substituents are as defined above.

Suitable groups represented by $R^8$ may be selected from hydrogen, linear or branched $(C_1-C_{16})$alkyl, preferably $(C_1-C_{12})$alkyl group such as methyl, ethyl, n-propyl, iso-propyl, n-butyl, iso-butyl, pentyl, hexyl, octyl and the like, the alkyl group may be substituted; $(C_3-C_7)$cycloalkyl such as cyclopropyl, cyclopentyl, cyclohexyl and the like, the cycloalkyl group may be substituted; aryl group such as phenyl, naphthyl and the like, the aryl group may be substituted; heteroaryl group such as pyridyl, thienyl, pyrrolyl, furyl and the like, the heteroaryl group may be substituted; heteroaralkyl group such as furanmethyl, pyridinemethyl, oxazolemethyl, oxazolethyl and the like, the heteroaralkyl group may be substituted; aralkyl group such as benzyl, phenethyl and the like, the aralkyl group may be substituted; heterocyclyl group such a aziridinyl, pyrrolidinyl, piperidinyl and the like, the heterocyclyl group may be substituted. The substituents on $R^8$ may be selected from halogen, hydroxy, nitro or unsubstituted or substituted groups selected from alkyl, cycloalkyl, alkoxy, cycloalkoxy, aryl, aralkyl, aralkoxyalkyl, heterocyclyl, heteroaryl, heteroaralkyl, acyl, acyloxy, hydroxyalkyl, amino acylamino, arylamino, aminoalkyl, aryloxy, aralkoxy, alkoxycarbonyl, alkylamino, alkoxyalkyl, alkylthio, thioalkyl groups, carboxylic acid or its derivatives, or sulfonic acid or its derivatives. The substituents are as defined above.

Suitable groups represented by $R^9$ may be selected from hydrogen, linear or branched $(C_1-C_{16})$alkyl, preferably $(C_1-C_{12})$alkyl group, such as methyl, ethyl, n-propyl, iso-propyl, n-butyl, iso-butyl, pentyl, hexyl, heptyl, octyl and the like; hydroxy$(C_1-C_6)$alkyl; aryl group such as phenyl, naphthyl and the like; aralkyl group such as benzyl, phenethyl the like; heterocyclyl group such as aziridinyl, pyrrolidinyl, piperidinyl and the like; heteroaryl group such as pyridyl, thienyl, pyrrolyl, furyl and the like; heteroaralkyl group such as furanmethyl, pyridinemethyl, oxazolemethyl, oxazolethyl and the like. The substituents may be selected from hydroxy, halogen, nitro, amino, alkyl, alkoxy or aryl.

Suitable chiral amines represented by $NR^9$ may be selected from R(+)-α-ethylphenylamine, naphthylethylamine, S(+) phenylglycinol, cinchonidine, ephedrine, N-octylglucaramine, N-methylglucaramine and the like; chiral amine alcohols such as phenyl glycinol, valine, tert-leucine and the like.

Suitable ring structures formed by $R^8$ and $R^9$ together may be selected from pyrrolidinyl, piperidinyl, morpholinyl, piperazinyl and the like.

Suitable groups represented by $R^{10}$ and $R^{11}$ may be selected from hydrogen, or substituted or unsubstituted linear or branched $(C_1-C_{12})$alkyl group, such as methyl, ethyl, n-propyl, iso-propyl, n-butyl, iso-butyl, t-butyl, n-pentyl, iso-pentyl, hexyl, heptyl, octyl, nonyl, decyl and the like; $(C_1-C_6)$alkoxy such as methoxy, ethoxy, propyloxy, butyloxy, iso-propyloxy and the like, which may be substituted; aryl group such as phenyl, naphthyl and the like, the aryl group may be substituted; aralkyl such as benzyl, phenethyl, C₆H₅CH₂CH₂CH₂, naphthylmethyl and the like. The substituents may be selected from hydroxy, halogen, nitro or amino.

Suitable groups represented by $R^{12}$ may be selected from hydrogen or substituted or unsubstituted linear or branched $(C_1-C_{12})$alkyl group such as methyl, ethyl, n-propyl, iso-propyl, n-butyl, iso-butyl, t-butyl, n-pentyl, iso-pentyl, hexyl, heptyl, octyl, nonyl, decyl and the like; aryl group such as phenyl, naphthyl and the like, the aryl group may be substituted; aralkyl group such as benzyl, phenethyl C₆H₅CH₂CH₂CH₂, naphthylmethyl and the like the substituents may be selected from hydroxy, halogen, nitro or amino.

Suitable n is an integer ranging from 0 to 6.

Suitable m is an integer ranging from 0 to 6.

Pharmaceutically acceptable salts forming part of this invention include salts derived from inorganic bases such as Li, Na, K, Ca, Mg, Fe, Cu, Zn, Mn; salts of organic bases such as N,N'-diacetylethylenediamine, betaine, caffeine, 2-diethylaminoethanol, 2-dimethylaminoethanol, N-ethyl-morpholine, N-ethylpiperidine, glucamine, glucosamine, hydrabamine; isopropylamine, methylglucamine, morpholine, piperazine, piperidine, procaine, purines, theobromine, glycinol, diethylamine, triethylamine, trimethylamine, tripropylamine, trometamine, adamentyl amine, diethanolamine, meglumine, ethylenediamine, N,N'-diphenylethyl-ethlendiamine, N,N'-dibenzylthylenediamine, N-benzyl phenylethylamine, choline, choline hydroxide, dicyclohexylamine, metformin, benzylamine, phenylethylamine, dialkylamine, trialkylamine, thiamine, aminopyrimdine, aminopyridine, purine, spermidine, and the like; chiral bases like alklphenylamine, phenyl glycinol and the like, salts of natural amino acids such as glycine, alanine, valine, leuucine, isoleucine, norleucine, tyrosine, cytosine, cysteine, methionine, proline, hydroxy proline, histidine, ornithine, lysine, arginine, serine, threonine, phenylalanine; unnatural amino acids such as D-isomers or substituted amino acids; guanidine, substituted guanidine wherein the substituents are selected from nitro, amino, alkyl, alkenyl, alkynyl, ammonium or substituted ammonium salts and aluminum salts. Salts may include acid addition salts where appropriate which are, sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, ketoglutarates and the like. Pharmaceutically acceptable solvates may be hydrates or comprising other solvents of crystallization such as alcohols.

Particularly useful compounds according to the present invention includes:

(±) Ethyl 3-[4-{3-(3,4-dihydro-2H-benzo[b][1,4]oxazin-4-yl)propylamino}phenyl]-2-ethoxypropanoate;

(+) Ethyl 3-[4-{3-(3,4-dihydro-2H-benzo[b][1,4]oxazin-4-yl)propylamino}phenyl]-2-ethoxypropanoate;

(−) Ethyl 3-[4-{3-(3,4-dihydro-2H-benzo[b][1,4]oxazin-4-yl)propylamino}phenyl]-2-ethoxypropanoate;

(±) 3-[4-{3-(3,4-Dihydro-2H-benzo[b][1,4]oxazin-4-yl)propylamino}phenyl]-2-ethoxypropanoic acid or its salts;

(+) 3-[4-{3-(3,4-Dihydro-2H-benzo[b][1,4]oxazin-4-yl)propylamino}phenyl]-2-ethoxypropanoic acid or its salts;

(−) 3-[4-{3-(3,4-Dihydro-2H-benzo[b][1,4]oxazin-4-yl)propylamino}phenyl]-2-ethoxypropanoic acid or its salts;

(±) Ethyl 3-[4-N-heptyl-N-{2-(3-oxo-3,4-dihydro-2H-benzo[b][1,4]oxazin-4-yl)ethylamino}phenyl]-2-ethoxypropanoate;

(+) Ethyl 3-[4-N-heptyl-N-{2-(3-oxo-3,4-dihydro-2H-benzo[b][1,4]oxazin-4-yl)ethylamino}phenyl]-2-ethoxypropanoate;

(−) Ethyl 3-[4-N-heptyl-N-{2-(3-oxo-3,4-dihydro-2H-benzo[b][1,4]oxazin-4-yl)ethylamino}phenyl]-2-ethoxypropanoate;

(±) 3-[4-N-Heptyl-N-{2-(3-oxo-3,4-dihydro-2H-benzo[b][1,4]oxazin-4-yl)ethylamino}phenyl]-2-ethoxypropanoic acid or its salts;

(+) 3-[4-N-Heptyl-N-{2-(3-oxo-3,4-dihydro-2H-benzo[b][1,4]oxazin-4-yl)ethylamino}phenyl]-2-ethoxypropanoic acid or its salts;

(−) 3-[4-N-Heptyl-N-{2-(3-oxo-3,4-dihydro-2H-benzo[b][1,4]oxazin-4-yl)ethylamino}phenyl]-2-ethoxypropanoic acid or its salts;

(±) Methyl 2-ethoxy-3-[4-{N-heptyl-N-(2-(3,4-dihydro-2H-benzo[b]oxazin-4-yl)-2-oxoethyl)aminomethyl}phenyl] propionate;

(+) Methyl 2-ethoxy-3-[4-{N-heptyl-N-(2-(3,4-dihydro-2H-benzo[b]oxazin-4-yl)-2-oxoethyl)aminomethyl}phenyl] propanoate;

(−) Methyl 2-ethoxy-3-[4-{N-heptyl-N-(2-(3,4-dihydro-2H-benzo[b]oxazin-4-yl)-2-oxoethyl)aminomethyl}phenyl] propanoate;

(±) 2-Ethoxy-3-[4-{N-heptyl-N-(2-(3,4-dihydro-2H-benzo[b]oxazin-4-yl)-2-oxoethyl)aminomethyl}phenyl]propanoic acid or its salts;

(+) 2-Ethoxy-3-[4-{N-heptyl-N-(2-(3,4-dihydro-2H-benzo[b]oxazin-4-yl)-2-oxoethyl)aminomethyl}phenyl]propanoic acid or its salts;

(−) 2-Ethoxy-3-[4-{N-heptyl-N-(2-(3,4-dihydro-2H-benzo[b]oxazin-4-yl)-2-oxoethyl)aminomethyl}phenyl]propanoic acid or its salts;

(±) Methyl 3-[4-{5-(3,4-dihydro-2H-benzo[b][1,4]oxazin-4-yl)-5-oxopentylamino}phenyl]-2-ethoxypropanoate;

(+) Methyl 3-[4-{5-(3,4-dihydro-2H-benzo[b][1,4]oxazin-4-yl)-5-oxopentylamino}phenyl]-2-ethoxypropanoate (−) Methyl 3-[4-{5-(3,4-dihydro-2H-benzo[b][1,4]oxazin-4-yl)-5-oxopentylamino}phenyl]-2-ethoxypropanoate;

(±) 3-[4-{5-(3,4-Dihydro-2H-benzo[b][1,4]oxazin-4-yl)-5-oxopentylamino}phenyl]-2-ethoxypropanoic acid or its salts;

(+) 3-[4-{5-(3,4-Dihydro-2H-benzo[b][1,4]oxazin-4-yl)-5-oxopentylamino}phenyl]-2-ethoxypropanoic acid or its salts;

(−) 3-[4-{5-(3,4-Dihydro-2H-benzo[b][1,4]oxazin-4-yl)-5-oxopentylamino}phenyl]-2-ethoxypropanoic acid or its salts;

(±) Methyl 3-[3-{3-(3,4-dihydro-2H-benzo[b][1,4]oxazin-4-yl)propylamino}phenyl]-2-ethoxypropanoate;

(+) Methyl 3-[3-{3-(3,4-dihydro-2H-benzo[b][1,4]oxazin-4-yl)propylamino}phenyl]-2-ethoxypropanoate;

(−) Methyl 3-[3-{3-(3,4-dihydro-2H-benzo[b][1,4]oxazin-4-yl)propylamino}phenyl]-2-ethoxypropanoate;

(±) 3-[3-{3-(3,4-Dihydro-2H-benzo[b][1,4]oxazin-4-yl)propylamino}phenyl]-2-ethoxypropanoic acid or its salts;

(+) 3-[3-{3-(3,4-Dihydro-2H-benzo[b][1,4]oxazin-4-yl)propylamino}phenyl]-2-ethoxypropanoic acid or its salts;

(−) 3-[3-{3-(3,4-Dihydro-2H-benzo[b][1,4]oxazin-4-yl)propylamino}phenyl]-2-ethoxypropanoic acid or its salts;

(±) Methyl 3-[4-{3-(7-fluoro-3,4-dihydro-2H-benzo[b][1,4] oxazin-4-yl)propylamino}phenyl]-2-ethoxypropanoate;

(+) Methyl 3-[4-{3-(7-fluoro-3,4-dihydro-2H-benzo[b][1,4] oxazin-4-yl)propylamino}phenyl]-2-ethoxypropanoate;

(−) Methyl 3-[4-{3-(7-fluoro-3,4-dihydro-2H-benzo[b][1,4] oxazin-4-yl)propylamino}phenyl]-2-ethoxypropanoate;

(±) 3-[4-{3-(7-Fluoro-3,4-dihydro-2H-benzo[b][1,4]oxazin-4-yl)propylamino}phenyl]-2-ethoxypropanoic acid or its salts;

(+) 3-[4-{3-(7-Fluoro-3,4-dihydro-2H-benzo[b][1,4]oxazin-4-yl)propylamino}phenyl]-2-ethoxypropanoic acid or its salts;

(−) 3-[4-{3-(7-Fluoro-3,4-dihydro-2H-benzo[b][1,4]oxazin-4-yl)propylamino}phenyl]-2-ethoxypropanoic acid or its salts;

(±) Methyl 2-ethoxy-3-[4-{4-(3-(3,4-dihydro-2H-benzo[b][1,4]oxazin-4-yl)propyloxy)benzyl}aminophenyl]propanoate;

(+) Methyl 2-ethoxy-3-[4-{4-(3-(3,4-dihydro-2H-benzo[b][1,4]oxazin-4-yl)propyloxy)benzyl}aminophenyl]propanoate;

(−) Methyl 2-ethoxy-3-[4-{4-(3-(3,4-dihydro-2H-benzo[b][1,4]oxazin-4-yl)propyloxy)benzyl}aminophenyl]propanoate;

(±) Methyl 2-ethoxy-3-[3-{4-(3-(3,4-dihydro-2H-benzo[b][1,4]oxazin-4-yl)propyloxy)benzyl}aminophenyl]propanoate;

(+) Methyl 2-ethoxy-3-[3-{4-(3-(3,4-dihydro-2H-benzo[b][1,4]oxazin-4-yl)propyloxy)benzyl}aminophenyl]propanoate;

(−) Methyl 2-ethoxy-3-[3-{4-(3-(3,4-dihydro-2H-benzo[b][1,4]oxazin-4-yl)propyloxy)benzyl}aminophenyl]propanoate;

(±) 2-Ethoxy-3-[4-{4-(3-(3,4-dihydro-2H-benzo[b][1,4]oxazin-4-yl)propyloxy)benzyl}aminophenyl]propanoic acid or its salts;

(+) 2-Ethoxy-3-[4-{4-(3-(3,4-dihydro-2H-benzo[b][1,4]oxazin-4-yl)propyloxy)benzyl}aminophenyl]propanoic acid or its salts;

(−) 2-Ethoxy-3-[4-{4-(3-(3,4-dihydro-2H-benzo[b][1,4]oxazin-4-yl)propyloxy)benzyl}aminophenyl]propanoic acid or its salts;

(±) 2-Ethoxy-3-[3-{4-(3-(3,4-dihydro-2H-benzo[b][1,4]oxazin-4-yl)propyloxy)benzyl}aminophenyl]propanoic acid or its salts;

(+) 2-Ethoxy-3-[3-{4-(3-(3,4-dihydro-2H-benzo[b][1,4]oxazin-4-yl)propyloxy)benzyl}aminophenyl]propanoic acid or its salts;

(−) 2-Ethoxy-3-[3-{4-(3-(3,4-dihydro-2H-benzo[b][1,4]oxazin-4-yl)propyloxy)benzyl}aminophenyl]propanoic acid or it salts;

(±) Ethyl 2-ethoxy-3-[4-{3-(3,4-dihydro-2H-benzo[b][1,4]thiazin-4-yl)propylamino}phenyl]propanoate;

(+) Ethyl 2-ethoxy-3-[4-{3-(3,4-dihydro-2H-benzo[b][1,4]thiazin-4-yl)propylamino}phenyl]propanoate;

(−) Ethyl 2-ethoxy-3-[4-{3-(3,4-dihydro-2H-benzo[b][1,4]thiazin-4-yl)propylamino}phenyl]propanoate;

(±) 2-Ethoxy-3-[4-{3-(3,4-dihydro-2H-benzo[b][1,4]thiazin-4-yl)propylamino}phenyl]propanoic acid or its salts;

(+) 2-Ethoxy-3-[4-{3-(3,4-dihydro-2H-benzo[b][1,4]thiazin-4-yl)propylamino}phenyl]propanoic acid or its salts;

(−) 2-Ethoxy-3-[4-{3-(3,4-dihydro-2H-benzo[b][1,4]thiazin-4-yl)propylamino}phenyl]propanoic acid or its salts;

(±) Ethyl 2-ethoxy-3-[4-{2-(3,4-dihydro-2H-benzo[b][1,4]oxazin-4-yl)ethylamino}phenyl]propanoate;

(+) Ethyl 2-ethoxy-3-[4-{2-(3,4-dihydro-2H-benzo[b][1,4]oxazin-4-yl)ethylamino}phenyl]propanoate;

(−) Ethyl 2-ethoxy-3-[4-{2-(3,4-dihydro-2H-benzo[b][1,4]oxazin-4-yl)ethylamino}phenyl]propanoate;

(±) 2-Ethoxy-3-[4-{2-(3,4-dihydro-2H-benzo[b][1,4]oxazin-4-yl)ethylamino}phenyl]propanoic acid or its salts;

(+) 2-Ethoxy-3-[4-{2-(3,4-dihydro-2H-benzo[b][1,4]oxazin-4-yl)ethylamino}phenyl]propanoic acid or its salts;

(−) 2-Ethoxy-3-[4-{2-(3,4-dihydro-2H-benzo[b][1,4]oxazin-4-yl)ethylamino}phenyl]propanoic acid or its salts;

(±) Methyl 2-ethoxy-3-[4-[4-{2-(3,4-dihydro-2H-benzo[b][1,4]oxazin-4-yl)ethoxy}phenylaminomethyl]phenyl]propanoate;

(+) Methyl 2-ethoxy-3-[4-[4-{2-(3,4-dihydro-2H-benzo[b][1,4]oxazin-4-yl)ethoxy}phenylaminomethyl]phenyl]propanoate;

(−) Methyl 2-ethoxy-3-[4-[4-{2-(3,4-dihydro-2H-benzo[b][1,4]oxazin-4-yl)ethoxy}phenylaminomethyl]phenyl]propanoate;

(±) 2-Ethoxy-3-[4-[4-{2-(3,4-dihydro-2H-benzo[b][1,4]oxazin-4-yl)ethoxy}phenylaminomethyl]phenyl]propanoic acid or its salts;

(+) 2-Ethoxy-3-[4-[4-{2-(3,4-dihydro-2H-benzo[b][1,4]oxazin-4-yl)ethoxy}phenylaminomethyl]phenyl]propanoic acid or its salts;

(−) 2-Ethoxy-3-[4-[4-{2-(3,4-dihydro-2H-benzo[b][1,4]oxazin-4-yl)ethoxy}phenylaminomethyl]phenyl]propanoic acid or its salts;

(±) Ethyl 3-[4-{3-(7-fluoro-3,4-dihydro-2H-benzo[b][1,4]oxazin-4-yl)propylamino}phenyl]-2-ethoxypropanoate (+) Ethyl 3-[4-{3-(7-fluoro-3,4-dihydro-2H-benzo[b][1,4]oxazin-4-yl)propylamino}phenyl]-2-ethoxypropanoate (−) Ethyl 3-[4-{3-(7-fluoro-3,4-dihydro-2H-benzo[b][1,4]oxazin-4-yl)propylamino}phenyl]-2-ethoxypropanoate (±) Ethyl 3-[4-{3-(7-fluoro-3,4-dihydro-2H-benzo[b][1,4]oxazin-4-yl)propylamino}phenyl]-2-methoxypropanoate (+) Ethyl 3-[4-{3-(7-fluoro-3,4-dihydro-2H-benzo[b][1,4]oxazin-4-yl)propylamino}phenyl]-2-methoxypropanoate (−) Ethyl 3-[4-{3-(7-fluoro-3,4-dihydro-2H-benzo[b][1,4]oxazin-4-yl)propylamino}phenyl]-2-methoxypropanoate (±) 3-[4-{3-(7-Fluoro-3,4-dihydro-2H-benzo[b][1,4]oxazin-4-yl)propylamino}phenyl]-2-methoxypropanoic acid or its salts (+) 3-[4-{3-(7-Fluoro-3,4-dihydro-2H-benzo[b][1,4]oxazin-4-yl)propylamino}phenyl]-2-methoxypropanoic acid or its salts (−) 3-[4-{3-(7-Fluoro-3,4-dihydro-2H-benzo[b][1,4]oxazin-4-yl)propylamino}phenyl]-2-methoxypropanoic acid or its salts (±) Ethyl 3-[4-{3-(2-methyl-7-fluoro-3,4-dihydro-2H-benzo[b][1,4]oxazin-4-yl)propylamino}phenyl]-2-ethoxypropanoate (+) Ethyl 3-[4-{3-(2-methyl-7-fluoro-3,4-dihydro-2H-benzo[b][1,4]oxazin-4-yl)propylamino}phenyl]-2-ethoxypropanoate (−) Ethyl 3-[4-{3-(2-methyl-7-fluoro-3,4-dihydro-2H-benzo[b][1,4]oxazin-4-yl)propylamino}phenyl]-2-ethoxypropanoate (±) 3-[4-{3-(2-methyl-7-Fluoro-3,4-dihydro-2H-benzo[b][1,4]oxazin-4-yl)propylamino}phenyl]-2-ethoxypropanoic acid or its salts (+) 3-[4-{3-(2-methyl-7-Fluoro-3,4-dihydro-2H-benzo[b][1,4]oxazin-4-yl)propylamino}phenyl]-2-ethoxypropanoic acid or its salts (−) 3-[4-{3-(2-methyl-7-Fluoro-3,4-dihydro-2H-benzo[b][1,4]oxazin-4-yl)propylamino}phenyl]-2-ethoxypropanoic acid or its salts (±) Ethyl 3-[4-{3-(2-methyl-3,4-dihydro-2H-benzo[b][1,4]oxazin-4-yl)propylamino}phenyl]-2-ethoxypropanoate (+) Ethyl 3-[4-{3-(2-methyl-3,4-dihydro-2H-benzo[b][1,4]oxazin-4-yl)propylamino}phenyl]-2-ethoxypropanoate (−) Ethyl 3-[4-{3-(2-methyl-3,4-dihydro-2H-benzo[b][1,4]oxazin-4-yl)propylamino}phenyl]-2-ethoxypropanoate (±) 3-[4-{3-(2-methyl-3,4-dihydro-2H-benzo[b][1,4]ox-azin-4-yl)propylamino}phenyl]-2-ethoxypropanoic acid or its salts (+) 3-[4-{3-(2-methyl-3,4-dihydro-2H-benzo[b][1,4]ox-azin-4-yl)propylamino}phenyl]-2-ethoxypropanoic acid or its salts (−) 3-[4-{3-(2-methyl-3,4-dihydro-2H-benzo[b][1,4]ox-azin-4-yl)propylamino}phenyl]-2-ethoxypropanoic acid or its salts (±) Ethyl 3-[4-{3-(2-methyl-3,4-dihydro-2H-benzo[b][1,4]oxazin-4-yl)propylamino}phenyl]-2-methoxypropanoate (+) Ethyl 3-[4-{3-(2-methyl-3,4-dihydro-2H-benzo[b][1,4]oxazin-4-yl)propylamino}phenyl]-2-methoxypropanoate (−) Ethyl 3-[4-{3-(2-methyl-3,4-dihydro-2H-benzo[b][1,4]oxazin-4-yl)propylamino}phenyl]-2-methoxypropanoate (±) 3-[4-{3-(2-methyl-3,4-dihydro-2H-benzo[b][1,4]ox-azin-4-yl)propylamino}phenyl]-2-methoxypropanoic acid or its salts (+) 3-[4-{3-(2-methyl-3,4-dihydro-2H-benzo[b][1,4]ox-azin-4-yl)propylamino}phenyl]-2-methoxypropanoic acid or its salts (−) 3-[4-{3-(2-methyl-3,4-dihydro-2H-benzo[b][1,4]ox-azin-4-yl)propylamino}phenyl]-2-methoxypropanoic acid or its salts (±) Ethyl 3-[4-{3-(2-propyl-3,4-dihydro-2H-benzo[b][1,4]oxazin-4-yl)propylamino}phenyl]-2-ethoxypropanoate (+) Ethyl 3-[4-{3-(2-propyl-3,4-dihydro-2H-benzo[b][1,4]oxazin-4-yl)propylamino}phenyl]-2-ethoxypropanoate (−) Ethyl 3-[4-{3-(2-propyl-3,4-dihydro-2H-benzo[b][1,4]oxazin-4-yl)propylamino}phenyl]-2-ethoxypropanoate (±) 3-[4-{3-(2-propyl-3,4-dihydro-2H-benzo[b][1,4]oxazin-4-yl)propylamino}phenyl]-2-ethoxypropanoic acid or its salts (+) 3-[4-{3-(2-propyl-3,4-dihydro-2H-benzo[b][1,4]oxazin-4-yl)propylamino}phenyl]-2-ethoxypropanoic acid or its salts (−) 3-[4-{3-(2-propyl-3,4-dihydro-2H-benzo[b][1,4]oxazin-4-yl)propylamino}phenyl]-2-ethoxypropanoic acid or its salts (±) Ethyl (2S)-3-[4-{3-(2-propyl-3,4-dihydro-2H-benzo[b][1,4]oxazin-4-yl)propylamino}phenyl]-2-methoxypropanoate (+) Ethyl (2S)-3-[4-{3-(2-propyl-3,4-dihydro-2H-benzo[b][1,4]oxazin-4-yl)propylamino}phenyl]-2-methoxypropanoate (−) Ethyl (2S)-3-[4-{3-(2-propyl-3,4-dihydro-2H-benzo[b][1,4]oxazin-4-yl)propylamino}phenyl]-2-methoxypropanoate (±) 3-[4-{3-(2-propyl-3,4-dihydro-2H-benzo[b][1,4]oxazin-4-yl)propylamino}phenyl]-2-methoxypropanoic acid and its salts (+) 3-[4-{3-(2-propyl-3,4-dihydro-2H-benzo[b][1,4]oxazin-4-yl)propylamino}phenyl]-2-methoxypropanoic acid and its salts (−) 3-[4-{3-(2-propyl-3,4-dihydro-2H-benzo[b][1,4]oxazin-4-yl)propylamino}phenyl]-2-methoxypropanoic acid and its salts (±) Ethyl 2-isopropoxy-3-[4-{3-(7-fluoro-3,4-dihydro-2H-benzo[b][1,4]oxazin-4-yl)propylamino}phenyl]propanoate (+) Ethyl 2-isopropoxy-3-[4-{3-(7-fluoro-3,4-dihydro-2H-benzo[b][1,4]oxazin-4-yl)propylamino}phenyl]propanoate (−) Ethyl 2-isopropoxy-3-[4-{3-(7-fluoro-3,4-dihydro-2H-benzo[b][1,4]oxazin-4-yl)propylamino}phenyl]propanoate (±) 2-Isopropoxy-3-[4-{3-(7-fluoro-3,4-dihydro-2H-benzo[b][1,4]oxazin-4-yl)propylamino}phenyl]propanoic acid and its salts (+) 2-Isopropoxy-3-[4-{3-(7-fluoro-3,4-dihydro-2H-benzo[b][1,4]oxazin-4-yl)propylamino}phenyl]propanoic acid and its salts (−) 2-Isopropoxy-3-[4-{3-(7-fluoro-3,4-dihydro-2H-benzo[b][1,4]oxazin-4-yl)propylamino}phenyl]propanoic acid and its salts (±) Ethyl 3-[4-{3-(2-methyl-7-fluoro-3,4-dihydro-2H-benzo[b][1,4]oxazin-4-yl)propylamino}phenyl]-2-methoxypropanoate (+) Ethyl 3-[4-{3-(2-methyl-7-fluoro-3,4-dihydro-2H-benzo[b][1,4]oxazin-4-yl)propylamino}phenyl]-2-methoxypropanoate (−) Ethyl 3-[4-{3-(2-methyl-7-fluoro-3,4-dihydro-2H-benzo[b][1,4]oxazin-4-yl)propylamino}phenyl]-2-methoxypropanoate (±) 3-[4-{3-(2-methyl-7-fluoro-3,4-dihydro-2H-benzo[b][1,4]oxazin-4-yl)propylamino}phenyl]-2-methoxypropanoic acid and its salts (+) 3-[4-{3-(2-methyl-7-fluoro-3,4-dihydro-2H-benzo[b][1,4]oxazin-4-yl)propylamino}phenyl]-2-methoxypropanoic acid and its salts (−) 3-[4-{3-(2-methyl-7-fluoro-3,4-dihydro-2H-benzo[b][1,4]oxazin-4-yl)propylamino}phenyl]-2-methoxypropanoic acid and its salts

[2S,N(1R)]-N-(2-hydroxy-1-phenylethyl)-2-ethoxy-3-[4-{3-(3,4-dihydro-2H-benzo[b][1,4]oxazin-4-yl)propylamino}phenyl]propanamide;

[2R,N(1R)]-N-(2-hydroxy-1-phenylethyl)-2-ethoxy-3-[4-{3-(3,4-dihydro-2H-benzo[b][1,4]oxazin-4-yl)propylamino}phenyl]propanamide;

2S,N(1R)]-N-(2-hydroxy-1-phenylethyl)-2-ethoxy-3-[4-{3-(7-fluoro-3,4-dihydro-2H-benzo[b][1,4]oxazin-4-yl)propylamino}phenyl]propanamide

[2R,N(1R)]-N-(2-hydroxy-1-phenylethyl)-2-ethoxy-3-[4-{3-(7-fluoro-3,4-dihydro-H-benzo[b][1,4]oxazin-4-yl)propylamino}phenyl]propanamide

[2S,N(1R)]-N-(2-hydroxy-1-phenylethyl)-2-ethoxy-3-[4-{3-(3,4-dihydro-2H-benzo[b][1,4]oxazin-4-yl)propylamino}phenyl]propanamide hydrochloride salt;

[2R,N(1R)]-N-(2-hydroxy-1-phenylethyl)-2-ethoxy-3-[4-{3-(3,4-dihydro-2H-benzo[b][1,4]oxazin-4-yl)propylamino}phenyl]propanamide hydrochloride salt;

According to another embodiment of the present invention, the compound of general formula (I) where $R^5$ and $R^6$ together represent a bond; Y represent oxygen or sulfur and W represents $N^{12}$; —O-aryl-$(CR^{10}R^{11})_o$—$NR^{12}$—, and all other symbols are as defined above may be prepared by one or more of processes shown in Scheme-I below.

Scheme-I

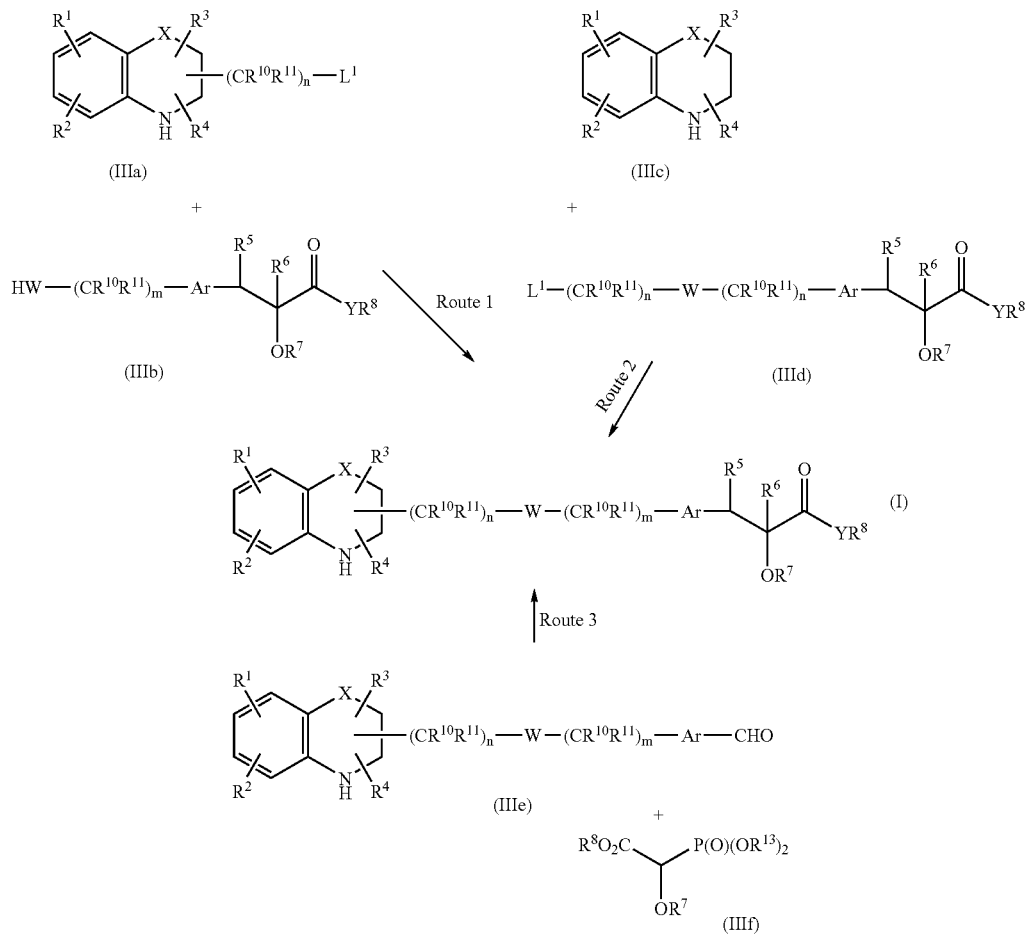

Route (1): The reaction of a compound of the general formula (IIIa) where $L^1$ is a leaving group such as halogen atom, metanesulfonate, trifluoromethanesulfonate, p-toluenesulfonate, p-nitrobenznensulfonate, acetate, sulfate, phosphate, hydroxy and the like, and all other symbols are as defined above with compound of formula (IIIb) where W represents $NR^{12}$, $—O-aryl-(CR^{10}R^{11})_o—NR^{12}—$; and all other symbols are as defined above to yield compound of general formula (I) where all symbols are as defined above may be carried out in the presence of a base such as metal carbonates like sodium carbonate, potassium carbonate, calcium carbonate, cesium carbonate and the like; metal bicarbonates like sodium bicarbonate, potassium bicarbonate, cesium bicarbonate and the like; metal hydrides like NaH or KH; metal hydroxides, like sodium hydroxide, potassium hydroxide, calcium hydroxide, cesium hydroxide and the like; alkoxides such as NaOMe, NaOEt, $K^+BuO^-$ and the like; organic bases such as guanidine, triethyl amine, pyridine, N-methyl morpholine and the like or mixtures thereof. The reaction may be carried out in the presence of solvents such as THF, dioxane, DMF, DMSO, DME, toluene, benzene, acetone, dimethyl acetamide, acetonitrile and the like or mixtures thereof Phase transfer catalyst such as tetraalkylammonium halides or hydroxides may be employed. The reaction temperature may range from 0° C. to 150° C., preferably at a temperature in the range of 10° C. to 120° C. When L1 represents, hydroxy group, the reaction may also be carried out using Mitsunobu conditions using reagents lie DEAD, DIAD and the like. The compound of formula (IIIa) was obtained by reacting compound of the formula (IVc)

where all symbols are as defined earlier, with a compound of formula (IVd)

$$L^1-(CR^{10}R^{11})_n-L^1 \qquad (IV\ d)$$

where $L^1$ and all other symbols are as defined above.

Route (2): The reaction of a compound of general formula (IIIc) where all symbols are as defined above with a compound of general formula (IIId) where $L^1$ is a leaving group such as halogen atom, methanesulfonate, trifluoromethanesulfonate, p-toluenesulfonate, p-nitrobenznensulfonate, acetate, sulfate, phosphate, hydroxy and the like, and all other symbols are as defined above to yield compound of general formula (I) where all symbols are as defined above may be carried out in the presence of a base such as metal carbonates like sodium carbonate, potassium carbonate, calcium carbonate, cesium carbonate and the like; metal bicarbonates like sodium bicarbonate, potassium bicarbonate, cesium bicarbonate and the like; metal hydrides like NaH or KH; metal hydroxides, like sodium hydroxide, potassium hydroxide, calcium hydroxide, cesium hydroxide and the like; alkoxiodes such as NaOMe, NaOEt, $K^+BuO^-$ and the like; organic bases such as guanidine, triethyl amine, pyridine, N-methyl morpholine and the like or mixtures thereof. The reaction may be carried out in the presence of solvents such as THF, dioxane, DMF, DMSO, DME, toluene, benzene, acetone, dimethyl acetamide, acetonitrile and the like or mixtures thereof. Phase transfer catalyst such as tetraalkylammonium halides or hydroxides may be employed. The reaction temperature may range from 0° C. to 150° C., preferably at a temperature in the range of 10° C. to 100° C. When $L^1$ represents, hydroxy group, the reaction may be also be carried out using Mitsunobu conditions using reagents lie DEAD, DIAD and the like.

Route (3): The reaction of a compound of the general formula (IIIe) where all symbols are as defined above with a compound of formula (IIIf) where $R^{13}$ represents $(C_1-C_6)$ alkyl group and all other symbols are as defined earlier to yield compound of general formula (I) where $R^5$ and $R^6$ together represent a bond and all other symbols are as defined above may be carried out in the presence of a base such as metal hydride such as NaH or KH; organolithiums such as $CH_3Li$, BuLi and the like; alkoxides such as NaOMe, NaOEt, $K^+BuO^-$ and the like or mixtures thereof. The reaction may be carried out in the presence of solvents such as diethyl ether, THF, dioxane, DMF, DMSO, DME, dimethyl acetamide and the like or mixtures thereof. HMPA may be used as cosolvent. The reaction temperature may range from −78° C. to 50° C., preferably at a temperature it the range of −10° C. to 30° C. The reaction is more effective under anhydrous conditions. The compound of general formula (IIIf) may be prepared according to the procedure described in the literature (Annalen. Chemie, (1996) 53, 699).

According to another embodiment, of the present invention, the compound of the general formula (I) where $R^5$ represents hydrogen atom, hydroxy, alkoxy, halogen, alkyl, substituted or unsubstituted aralkyl group represents hydrogen, hydroxy, alkoxy, halogen, alkyl group, acyl, substituted or unsubstituted aralkyl; Y represents oxygen and W represents $NR^{12}$, $-O-aryl-(CR^{10}R^{11})_o-NR^{12}-$; and all other symbols are as defined above may be prepared by one or more of processes shown in Scheme-II below.

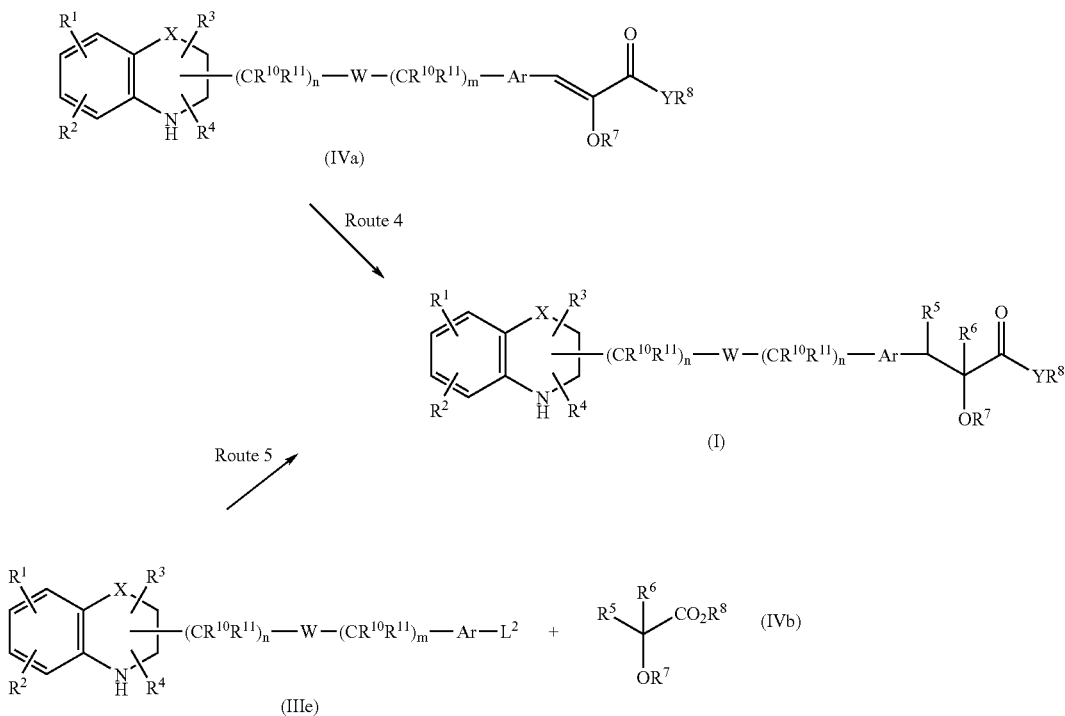

Route (4): The reduction of compound of the formula (IVa) which represents a compound of formula (I) where $R^5$ and $R^6$ represent a bond and Y represents oxygen atom and all other symbols are as defined earlier, obtained as described earlier in Scheme-I, to yield a compound of the general formula (I) where $R^5$ and $R^6$ each represent hydrogen atom and all symbols are as defined earlier, may be carried out in the presence of gaseous hydrogen and a catalyst such as Pd/C, Rh/C, Pt/C, Raney nickel and the like. Mixtures of catalysts may be used. The reaction may also be conducted in the presence of solvents such as dioxane, acetic acid, ethyl acetate, methanol, ethanol, isopropanol and the like. A pressure between atmospheric pressure and 80 psi may be employed. High pressures may be used to reduce the reaction time. The catalyst may be preferably 5-10% Pd/C and the amount of catalyst used may range from 1-50% w/w.

The reaction may also be carried out by employing metal solvent reduction such as magnesium, samarium in alcohol or sodium amalgam in alcohol, preferably methanol. The hydrogenation may be carried out in the presence of metal catalysts containing chiral ligands to obtain a compound of formula (I) in optically active form. The metal catalyst may contain Rhodium, Ruthenium, Indium and the like. The chiral ligands may preferably be chiral phosphines such as (2S,3S)-bis(diphenylphosphino)butane, 1,2-bis(diphenylphosphino)ethane, 1,2-bis(2-methoxyphenylphenylphosphino)ethane, (−)-2,3-isopropylidene-2,3-dihydroxy-1,4-bis(diphenylphosphino) butane and the like. Any suitable chiral catalyst may be employed which world give required optical purity of the product (I).

Route (5): The reaction of a compound of the general formula (IIIe) where $L^1$ is a leaving group such as halogen atom, methanesulfonate, trifluoromethanesulfonate, p-toluenesulfonate, p-nitrobenznensulfonate, acetate, sulfate, phosphate, hydroxy and the like, and all other symbol are as defined above with a compound of formula (IVb) where $R^5$ represents hydrogen and all other symbols ate as defined earlier to yield compound of general formula (I) where $R^5$ and $R^6$ represent a hydrogen atom and all other symbols are as defined above may be carried out in the presence of a base such as metal hydride such as NaH or KH; organolithiums such as $CH_3Li$, $LiN(iPr)_2$, LiHMDS, $LiN(Et)_2$, NaHMDS, KHMDS, BuLi and the like; alkoxides such as NaOMe, NaOEt, t-BuO$^-$K$^+$ and the like mixtures thereof. The reaction nay be carried out in the presence of solvents such as diethyl ether, THF, dioxane, DMF, DMSO, DME, dimethyl acetamide and the like or mixtures thereof. HMPA may be used as cosolvent. The reaction temperature may range from −78° C. to 50° C., preferably at a temperature in the range of −10° C. to 30° C. The reaction is more effective under anhydrous conditions According to another embodiment of the present invention, the compound of the general formula (I) where Y represents oxygen or sulfur and W represents —C(=O)—$(CR^{10}R^{11})_o$—$NR^{12}$— where o is an integer ranging from 0-6 and all other symbols are as defined above may be prepared by a process which comprises: reacting the compound of formula (IIIg)

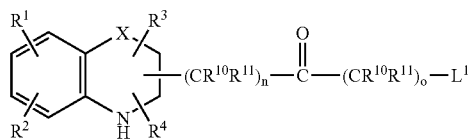

(IIIg)

where $L^1$ is a leaving group such as halogen atom, methanesulfonate, trifluoromethanesulfonate, p-toluenesulfonate, p-nitrobenznensulfonate, acetate, sulfate, phosphate, hydroxy and the like, and all other symbols are as defined above with compound of formula (IIIb)

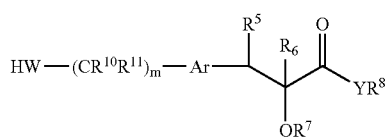

(IIIb)

where W represents $NR^{12}$, $R^{12}$ represents hydrogen and all other symbols are as defined above in the presence of a base such as metal carbonates like sodium carbonate, potassium carbonate, calcium carbonate, cesium carbonate and the like; metal bicarbonates like sodium bicarbonate, potassium bicarbonate, cesium bicarbonate and the like; metal hydrides like NaH or KH; metal hydroxides, like sodium hydroxide, potassium hydroxide, calcium hydroxide and the like; alkoxides such as NaOMe, NaOEt, K$^+$BuO$^-$ and the like; organic bases such as guanidine, triethyl amine, pyridine, N-methyl morpholine and the like or mixtures thereof. The reaction may be carried out in the presence of solvents such as THF, dioxane, DMF, DMSO, DME, toluene, benzene, acetone, dimethyl acetamide, acetonitrile and the like or mixtures thereof. Phase transfer catalyst such as tetraalkylammonium halides or hydroxides may be employed. The reaction temperature may range from 0° C. to 150° C., preferably at a temperature in the range of 10° C. to 120° C. When $L^1$ represents, hydroxy group, the reaction may be also be carried out using Mitsunobu conditions using reagents lie DEAD, DIAD and the like.

According to yet another embodiment of the present invention, the compound of the general formula (I) where Y represents oxygen and W represents —O-aryl-$(CR^{10}R^{11})_o$—$NR^{12}$—; and all other symbols are as defined above may be prepared by a process which comprises: reacting the compound of formula (IIIi)

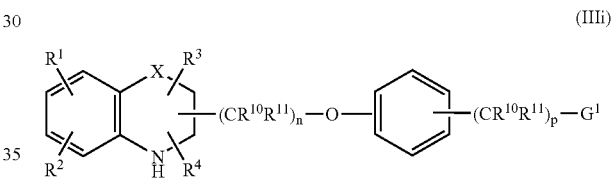

(IIIi)

where n and p are integers ranging from 0-6, $G^1$ represents $NH_2$ or formyl and all other symbols are as defined above with compound of formula (IIIh)

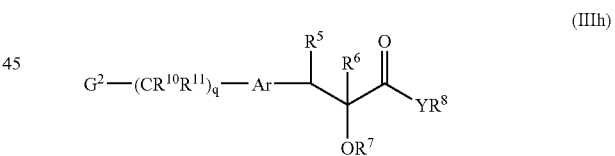

(IIIh)

where q is an integer ranging from 0-6, $G^2$ represent $NH_2$ or formyl and all other symbols are as defined above using solvents such as $CH_2Cl_2$, $CHCl_3$, chlorobenzene, benzene, THF, in the presence of catalyst such as p-toluenesulfonic acid, methanesulfonic acid, TFA, TfOH, $BF_3$—$OEt_2$ and the like. The reaction may also be carried out using activated molecular sieves. The temperature of the reaction may range from 10° C. to 100° C., preferably at a temperature in the range from 10° C. to 60° C. The imine product initially produce may be reducing using Na(CN)BH$_3$—HCl (ref: Hutchins, R. O. et al. J. Org. Chem. 1983, vol. 48, 3433-3428), H2-Pd/C, H$_2$-Pt/C, H$_2$-Ph/C and the like in solvents such as methanol, ethanol and the like.

The compound of formula (I) where $R^8$ represents hydrogen atom may be prepared by hydrolysing, using conventional methods, a compound of formula (I) where $R^8$ represents all groups defined earlier excluding hydrogen. The hydrolysis may be carried out in the presence of a base such as Na$_2$CO$_3$ and a suitable solvent such as methanol, ethanol and the like or mixtures thereof. The reaction may be carried out at a temperature in the range of 20° C.-40° C., preferably at 25° C.-30° C. The reaction time may range from 2 to 12 h, preferably from 4 to 8 h.

The compound of general formula (I) where Y represents oxygen and R$^8$ represents hydrogen or lower alkyl group may be converted to compound of formula (I), where Y represents NR$^9$ by reaction with appropriate amines of the formula NHR$^8$R$^9$, where R$^8$ and R$^9$ are as defined earlier to yield a compound of formula (I) where Y represents NR$^9$ and all other symbols are as defined earlier. Alternatively, the compound of formula (I) where YR$^8$ represents OH may be converted to acid halide, preferably YR$^8$=Cl, by reacting with appropriate reagents such as oxalyl chloride, thionyl chloride and the like, followed by treatment with amines of the formula NHR$^8$R$^9$ where R$^8$ and R$^9$ are as defined earlier. Alternatively, mixed anhydrides may be prepared from compound of formula (I) where YR$^8$ represents OH and all other symbols are as defined earlier by treating with acid halides such acetyl chloride, acetyl bromide, pivaloyl chloride, dichlorobenzoyl chloride and the like. The reaction may be carried out in the presence of suitable base such as pyridine, triethylamine, diisopropyl ethylamine and the like. Solvents such as halogenated hydrocarbons like CHCl$_3$ or CH$_2$Cl$_2$; hydrocarbons such as benzene, toluene, xylene and the like may be used. The reaction may be carried out at a temperature in the range of −40° C. to 40° C., preferably at a temperature in the range of 0° C. to 20° C. The acid halide or mixed anhydride thus prepared may further be treated with appropriate amines of the formula NHR$^8$R$^9$ where R$^8$ and R$^9$ are as defined earlier to yield a compound of formula (I) where Y represents NR$^9$ and all other symbols are as defined earlier.

In still another embodiment of the present invention the novel intermediate of formula (IIIb)

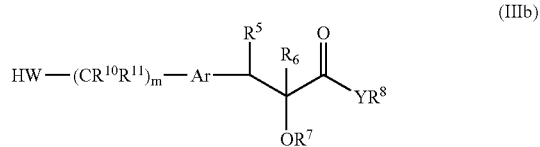

(IIIb)

their derivatives, their analogs, their tautomeric forms, their stereoisomers, their salts, their solvates wherein W represents NR$^{12}$, R$^{12}$ represents hydrogen, R$^{10}$ and R$^{11}$ may be same or different and represent hydrogen or substituted or unsubstituted group selected form alkyl, alkoxy, aryl or aralkyl group; Ar represents substituted or unsubstituted divalent single or fused aromatic or heterocyclic group; R$^5$ represents hydrogen atom, hydroxy, alkoxy, halogen, alkyl, substituted or unsubstituted aralkyl group or forms a bond together with the adjacent group R$^6$; R$^6$ represents hydrogen, hydroxy, alkoxy, halogen, lower alkyl group, acyl, substituted or unsubstituted aralkyl or R$^6$ forms a bond together with R$^5$; R$^7$ may be hydrogen or substituted or unsubstituted groups selected from alkyl, cycloalkyl, aryl, aralkyl, alkoxyalkyl, alkoxycarbonyl, aryloxycarbonyl, alkylaminocarbonyl, arylaminocarbonyl, acyl, heterocyclyl, heteroaryl, heteroaralkyl groups; R$^8$ may be hydrogen or substituted or unsubstituted groups selected from alkyl, cycloalkyl, aryl, aralkyl, heterocyclyl, heteroaryl or heteroaralkyl groups; Y represents oxygen, sulfur or NR$^{13}$, where R$^{13}$ represents hydrogen or substituted or unsubstituted groups selected from alkyl, aryl, hydroxyalkyl, aralkyl heterocyclyl, heteroaryl, or heteroaralkyl groups; R$^8$ and R$^{13}$ together may form a substituted or unsubstituted 5 or 6 membered cyclic structure containing carbon atoms, which may optionally contain one or more heteroatoms selected from oxygen, sulfur or nitrogen, m and n are integers 0-6 is provided.

The novel intermediate of formula (IIIb) where m is 0 and all other symbols are as defined above may be prepared by reducing the compound of formula (IIIj)

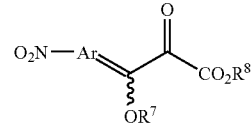

(IIIj)

where R$^7$, R$^8$ and Ar are as defined above in the presence of gaseous hydrogen and a catalyst such as Pd/C, Rh/C, Pt/C, Raney nickel and the like. Mixtures of catalysts may be used. The reaction may also be conducted in the presence of solvents such as dioxane, acetic acid, ethyl acetate and the like. A pressure between atmospheric pressure and 80 psi may be employed. The catalyst may be preferably 5-10% Pd/C and the amount of catalyst used may range from 1-50% w/w. The reaction may also be carried out by employing metal solvent reduction such as magnesium, iron, tin, samarium in alcohol or sodium amalgam in alcohol, preferably methanol. The hydrogenation may be carried out in the presence if metal catalysts containing chiral ligands to obtain compound of formula (I) in optically active form. The metal catalyst may contain Rhodium, Ruthenium, Indium and the like. The chiral ligands may preferably be chiral phosphines such as (2S,3S)-bis(diphenylphosphino)butane, 1,2-bis(diphenylphosphino)ethane, 1,2-bis(2-methoxyphenylphenylphosphino)ethane, (−)-2,3-isopropylidene-2,3-dihydroxy-1,4-bis(diphenylphosphino) butane and the like. (Ref: Principles of Asymmetric Synthesis, Tet. Org. Chem. Series Vol 14, pp311-316, Ed. Baldwin J. E.).

The compound of formula (IIIj) may be prepared by reacting the compound of formula (IIIm)

$$O_2N-Ar-CHO \quad \text{(IIIm)}$$

where Ar is as defined above with compound of formula (IIIf)

(IIIf)

where R$^{13}$ represents (C$_1$-C$_6$)alkyl group and all other symbols are as defined earlier in the presence of a base such as metal hydride such as NaH or KH; organolithiums such as CH$_3$Li, BuLi and the like; alkoxides such as NaOMe, NaOEt, t-BuO$^-$K$^+$ and the like or mixtures thereof. The reaction may be carried out in the presence of solvents such as diethyl ether, THF, dioxane, DMF, DMSO, DME, dimethyl acetamide and the like or mixtures thereof. HMPA may be used as cosolvent. The reaction temperature may range from −78° C. to 50° C., preferably at a temperature in the range of −10° C. to 30° C. The reaction is more effective under anhydrous conditions. The compound of general formula (III b) may be prepared according to the procedure described in the literature (Annalen. Chemie, (1996) 53, 699).

In yet another embodiment of the present invention, the compound of formula (IIIb) where m is 0 and all other symbols are as defined above may be prepared by diazotizing the compound of formula (IIIk) to a compound of formula (IIIl) and reducing the compound of formula (IIIl) to yield compound of formula (IIIb). The reaction shown in scheme-III below:

Scheme-III

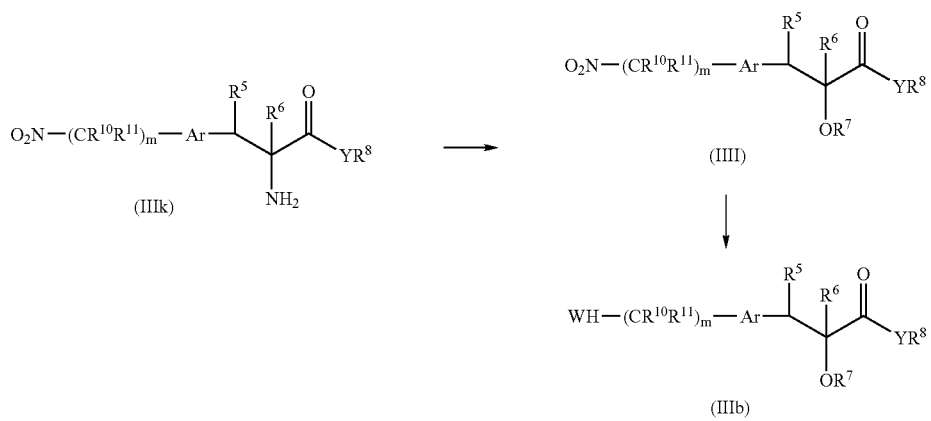

The diazotiaziaon of the compound of the formula (IIIk) to obtain compound of formula (IIII) may be carried out using diazotizing agent such as sodium nitrite, isoamyl nitrate, potassium nitrite, ammonium nitrite and the like under acidic conditions using acids such as sulfuric acid, HCl, acetic acid and the like, in an organic solvent such as alcohols such as methanol, ethanol, propanol and the like; 1,4-dioxane, THF, acetone and the like. Etherifying the resiude using alkyl sulfates such as diethyl sulphate, dimethylsulphate and the like or alkyl halides such as ethyl iodide, methyliodide and the like, in the presence of solvents such as hydrocarbons like toluene, benzene and the like or DMF, DMSO, acetonitrile, THF, methyl isobutyl ketone (MIBK) and the like, in alkali bases such as sodium carbonate, potassium carbonate, sodium methoxide, sodium hydride, potassium hydride and the like.

The reduction of compound of the formula (IIII) to yield a compound of the general formula (IIIb) may be carried out in the presence of gaseous hydrogen and a catalyst such as Pd/C, Rh/C, Pt/C, Raney nickel and the like. Mixtures of catalysts way be used. The reaction may also be conducted in the presence of solvents such as dioxane, acetic acid, ethyl acetate and the like. A pressure between atmospheric pressure and 80 psi may be employed. The catalyst may be preferably 5-10% Pd/C and the amount of catalyst used may rage from 1-50% w/w. The reaction may also be carried out by employing metal solvent reduction such as, magnesium, iron, tin, samarium in alcohol or sodium amalgam in alcohol, preferably methanol. The hydrogenation may be carried out in the presence of metal catalysts containing chiral ligands to obtain a compound of formula (I) in optically active form. The metal catalyst may contain Rhodium, Ruthenium, Indium and the like. The chiral ligands may preferably be chiral phosphines such as (2S,3S)-bis(diphenylphosphino)butane, 1,2-bis(diphenylphosphino)ethane, 1,2-bis(2-methoxyphenylphenylphosphino)ethane, (−)-2,3-isopropylidene-2,3-dihydroxy-1,4-bis(diphenylphosphino) butane and the like. (Ref: Principles of Asymmetric Synthesis, Tet. Org. Chem. Series Vol 14, pp311-316, Ed. Baldwin J. E.).

In yet another embodiment of the present invention, the compound of formula (IIIb) where m is 1-6, and all other symbols are as defined above may be prepared by following the process described in scheme-IV below:

Scheme-IV

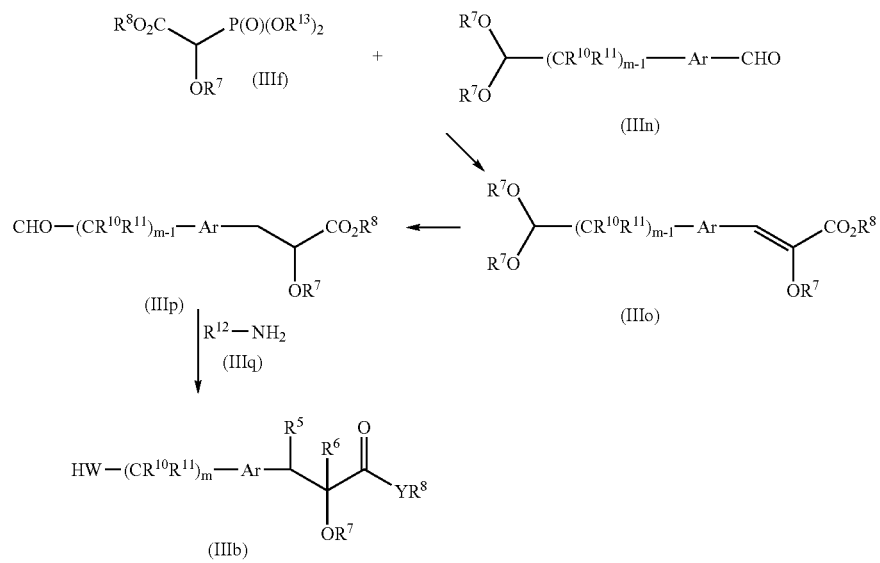

The reaction of a compound of the general formula (IIIf) defined above with a compound of formula (IIIn), to yield compound of formula (IIIo) may be carried out in the presence of a base such as metal hydride like NaH or KH; organolithiums such as CH₃Li, BuLi and the like; alkoxides such as NaOMe, NaOEt, t-BuO⁻K⁺ and the like or mixtures thereof. The reaction may be carried out in the presence of solvents such as diethyl ether, THF, dioxane, DMF, DMSO, DME, dimethyl acetamide and the like or mixtures thereof. HMPA may be used as cosolvent. The reaction temperature may range from −78° C. to 50° C., preferably at a temperature in the range of −10° C. to 30° C.

The reduction of compound of the formula (IIIo) to yield a compound of the formula (IIIp) may be carried out in the presence of gaseous hydrogen and a catalyst such as Pd/C, Rh/C, Pt/C, Raney nickel and the like. Mixtures of catalysts may be used. The reaction may also be conducted in the presence of solvents such as dioxane, acetic acid, ethyl acetate and the like. A pressure between atmospheric pressure and 80 psi may be employed. The catalyst may be preferably 5-10% Pd/C and the amount of catalyst used may range from 1-50% w/w. The reaction may also be carried out by employing metal solvent reduction such as magnesium, iron, tin, samarium in alcohol or sodium in alcohol, preferably methanol. The hydrogenation may be carried out in the presence off catalysts containing chiral ligands to obtain a compound of formula (I) in optically active form. The metal catalyst may contain Rhodium, Ruthenium, Indium and the like. The chiral ligands may preferably be chiral phosphines such as (2S,3S)-bis(diphenylphosphino)butane, 1,2-bis (diphenylphosphino)ethane, 1,2-bis(2-methoxyphenylPhe- nylphosphino)ethane, (−)-2,3-isopropylidene-2,3-dihy- droxy-1,4-bis(diphenylphosphino)butane and the like.

The reaction of a compound of general formula (IIIp) with a compound of formula (IIIq) may be carried out using solvents such as CH₂Cl₂, CHCl₃, chlorobenzene, benzene, THF, in the presence of catalyst such as p-toluenesulfonic acid, methanesulfonic acid, TFA, TfOH, BF₃-OEt₂ and the like. The reaction may also be carried out using activated molecular sieves. The temperature of the reaction may range from 10° C. to 100° C., preferably at a temperature in the range from 10° C. to 60° C. The imine product initially produce may be reducing using Na(CN)BH₃—HCl (ref: Hutchins, R. O. et al. J. Org. Chem. 1983, vol. 48, 3433-3428), H2-Pd/C, H₂-Pt/C, H₂-Ph/C and the like in solvent such as methanol, ethanol and the like.

In yet another embodiment of the present invention, the compound of formula (IIIb) where m is 0 or 1 and all other symbols are as defined above may be prepared by diazotizing the compound of formula (IIIk) to a compound of formula (Va), decomposition of compound of formula (Va) to a compound of formula (IIII) m the presence of alcohol such as R⁷OH and reducing the compound of formula (IIII) to yield compound of formula (IIIb). The reaction sequence is shown in scheme-V below:

Scheme-V

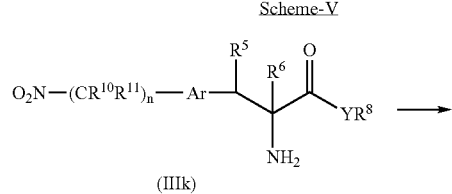

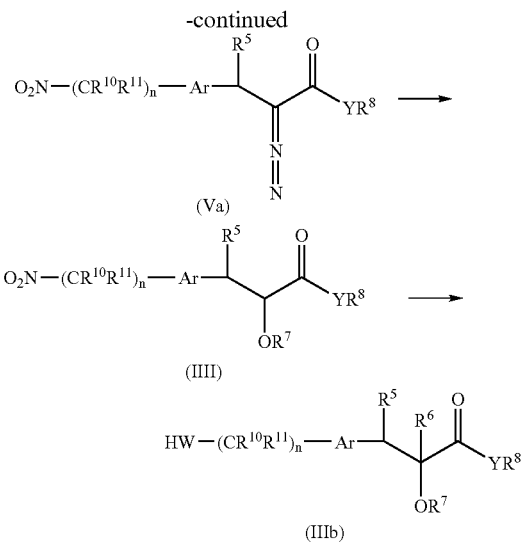

The diazotiaziaon of the compound of the formula (IIIk) where m is 0, R⁶ is hydrogen and all other symbols are as defined above, to obtain compound of formula (Va) may be carried out using diazotizing agent such as sodium nitrite, isoamyl nitrite, potassium nitrite, ammonium nitrite and the like in the presence of catalytic amount of carboxylic acid such as acetic acid, propionic acid and the like, in suitable solvent such as chloroform, chlorobenzene, dichloroethane and the like or a mixture thereof at a temperature in the range of room temperature and reflux temperature of the solvent employed for a period in the range of 0.5 to 16 h.

Decomposing the arylalkyl diazo acetate of the formula (Va) to obtain a compound of formula (IIII) where R⁷ is as defined earlier excluding hydrogen and all other symbols are as defined earlier can be promoted by a suitable catalyst such as Rh(II)acetate, salt/complex of Cu(I) or Rh(II) and the like (*Bio. Org. Med. Chem. Lett.,* 1996, 2121-2126) in the presence of an alcohol of the formula R⁷OH.

The reduction of compound of the formula (IIII) to yield a compound of the general formula (IIIb) where all symbols are as defined earlier may be carried out in the presence of gaseous hydrogen and a catalyst such as Pd/C, Rh/C, Pt/C, Raney nickel and the like. Mixtures of catalysts may be used. The reaction may also be conducted in the presence of solvents such as dioxane, acetic acid, ethyl acetate and the like. A pressure between atmospheric pressure and 80 psi may be employed. The catalyst may be preferably 5-10% Pd/C and the amount of catalyst used may range from 1-50% w/w. The reaction may also be carried out by employing metal solvent reduction such as magnesium, iron, tin, samarium in alcohol or sodium amalgam in alcohol; preferably methanol. The hydrogenation may also be carried out using ammonium formate, cyclohex-1,4-diene type of hydrogen donor under pd/c conditions using solvents such as methanol, ethanol, ethyl acetate and the like.

In yet another embodiment of the present invention, the compound of formula (IIIb) in its enantiomerically pure form, where m is 0, R⁵=R⁶=H and all other symbols are as defined above may be prepared by following the process described in scheme-VI below:

Scheme-VI

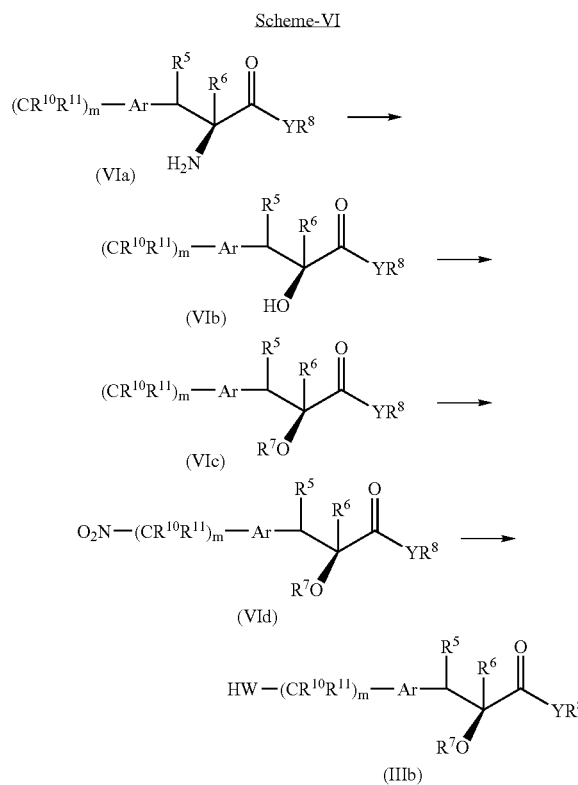

The diazotization of the compound of the formula (VIa) where all symbols are as defined above to obtain compound of formula (VIb) may be carried out by using diazotizing agent such as sodium nitrite, isoamyl nitrite, potassium nitrite, ammonium nitrite and the like under aqueous acidic conditions using acids such as sulfuric acid, HCl, acetic acid and the like, in a organic solvent such as alcohols such as methanol, ethanol, propanol and the like; 1,4-dioxane, THF, acetone and the like.

One pot esterification and etherification of compound of general formula (VIb) to a compound of general formula (VIc) may be carried by initial di deprotonation of (VIb) using a suitable base such as NaH, KH, KOH or like, in a suitable solvent such as toluene, benzene, diethylether, THF, DMF, DME HMPA, and like, followed by treatment with alkyl halide such as ethyl iodide or methyl iodide and like. Other alkylating agents such as $Et_3O^+BF_4^-$; $Me_3O^+BF_4^-$, dialkylsulfate may also be used. Reaction temperature may vary from 0° C. to 100° C.

Nitration of the compound of formula (VIc) to a compound of formula (VId) where n is 0 and all other symbols are as defined above, may be carried out using nitrating agents such as fuming nitric acid, $N_2O_5$, a mixture of conc. Nitric acid and conc. Sulfuric acid or a mixture of nitric acid and acetic anhydride in the presence of a solvent or under neat condition at a temperature in the range of −10° C. to room temperature for a period in the range of 0.5 to 4 h. (Ref Org. Synth. Col. Vol. I, 396)

Reduction of compound of the formula (VId) to a compound of the formula (IIIb), may be carried out in the presence of gaseous hydrogen or hydrogen donors such as ammonium formate, cyclohex-1,4-diene and the like and a catalyst such as Pd/C, Rh/C, Pt/C, Raney nickel and the like. Mixtures of catalysts may be used in the presence of solvents such as methanol, ethanol, dioxane, acetic acid, ethyl acetate and the like. A pressure between atmospheric pressure and 80 psi may be employed. The catalyst may be preferably 5-10% Pd/C and the amount of catalyst used may range from 1-50% w/w. Alternatively, the reaction may also be carried out by employing metal solvent reduction such as magnesium, iron, tin, samarium, indium, sodium amalgam in alcohol, or other suitable solvents preferably methanol.

In yet another embodiment of the present invention, the compound of formula (IIIb) in its enantiomerically pure form, where m is 0, $R^5=R^6=H$ and all other symbols are as defined above may be prepared by following the process described in scheme-VII below:

Scheme VII

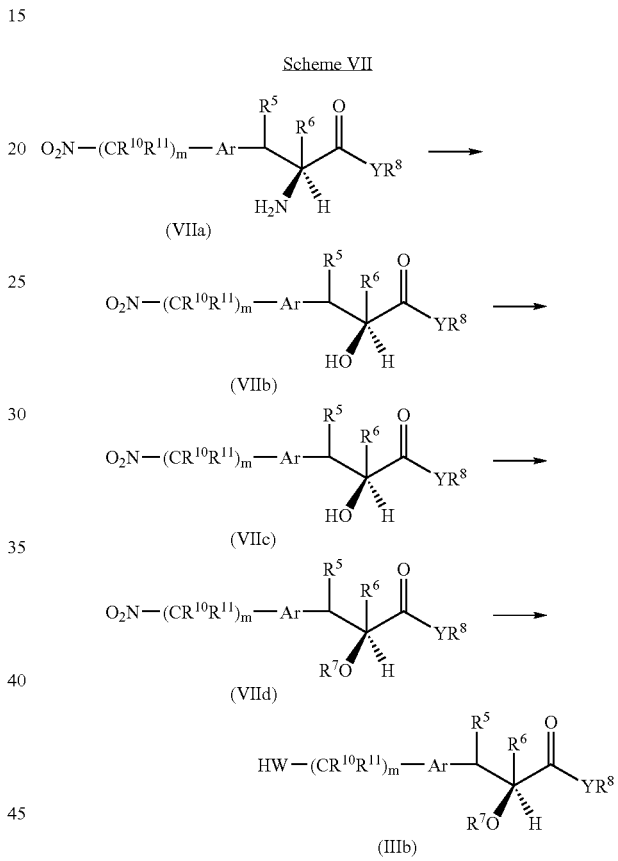

The diazotization of the compound of formula (VIIa) where all symbols are as defined above to obtain a compound of formula (VIIb) may be carried out using diazotizing agents such as sodium nitrite, isoamyl nitrite, potassium nitrite, ammonium nitrite and the like under acid aqueous acidic conditions using acids such as sulfuric acid, hydrochloric acid, acetic acid and the like, in presence of an optional co solvent like alcohols such as methanol, propanol, and the like; or ethers such as 1,4-dioxane, THF, and the like; or ketones such as acetone, methyl ethyl ketone and the like.

Esterification of the compound of formula (VIIb) to a compound of formula (VIIc) may be done using an appropriate alcohol of formula $R^8$—OH where $R^8$ represents lower alkyl groups such as methyl, ethyl, propyl, isopropyl, n-butyl, t-butyl and the like in presence of suitable catalyst such as, conc. sulfuric acid, dry HCl, $BF_3$—$OEt_2$, and the like. The reaction may be carried out at reflux temperature of the alcohol employed. Alternatively reagents like diazomethane or $Et_3O^+BF_4^-$ or $Me_3O^+B_4^-$ and the like may also be used for esterification.

Selective O-alkylation of the compound of formula (VIIc) to the compound of formula (VIId) may be done using alkyl sulfates such as diethyl sulfate, dimethyl sulfate and the like or alkyl halides such as ethyl iodide, methyl iodide, n-propyl iodide, n-propyl bromide, isopropyl iodide and the like, in solvents such as hydrocarbons like toluene, benzene and the like or acetonitrile, tetrahydro furan, dimethyl formamide, dimethyl sulfoxide, and the like, in the presence of molecular sieves and alkali bases such as sodium carbonate, potassium carbonate, cesium carbonate, sodium methoxide, sodium hydride, potassium hydride, sodium or potassium hydroxide and the like. Heavy metal oxides such as $Ag_2O$, PbO, HgO and the like may be of particular use to carry out alkylation when alkyl halides are used as alkylation reagent. Phase transfer catalysts such as tetraalkylammonium hydroxide or tetraalkylammonium halides such as tetrabutylammonium chloride, tetrabutylammonium bromide and the like may also be employed.

Reduction of compound of the formula (VIId) to a compound of formula (IIIb), may be carried out in the presence of gaseous hydrogen or hydrogen donors such as ammonium formate, cyclohex-1,4-diene and the like and a catalyst such as Pd/C, Rh/C, Pt/C, Raney nickel and the like. Mixtures of catalysts may be used in the presence of solvents such as methanol, ethanol, dioxane, acetic acid, ethyl acetate and the like. A pressure between atmospheric pressure and 80 psi may be employed. The catalyst may be preferably 5-10% Pd/C and the amount of catalyst used may range from 1-50% w/w. Alternatively, the reaction may also be carried out by employing metal solvent reduction such as magnesium, iron, tin, samarium, indium, sodium amalgam in alcohol, or other suitable solvents preferably methanol.

In yet another embodiment of the present invention, the compound of formula (IIIb) in its enantiomerically pure form, where m is 0, $R^5=R^6=H$ and all other symbols are as defined above may be prepared by following the process described in scheme-VIII below:

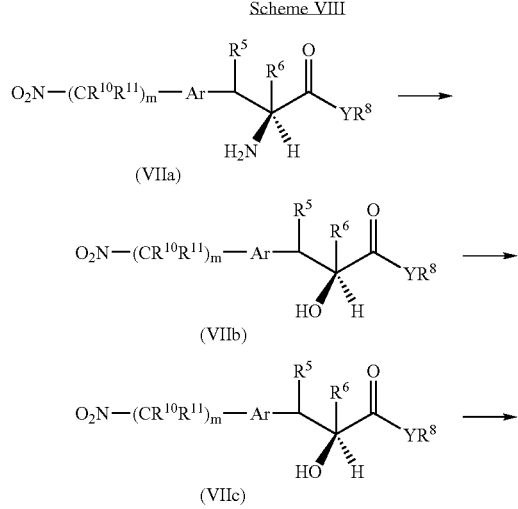

Scheme VIII

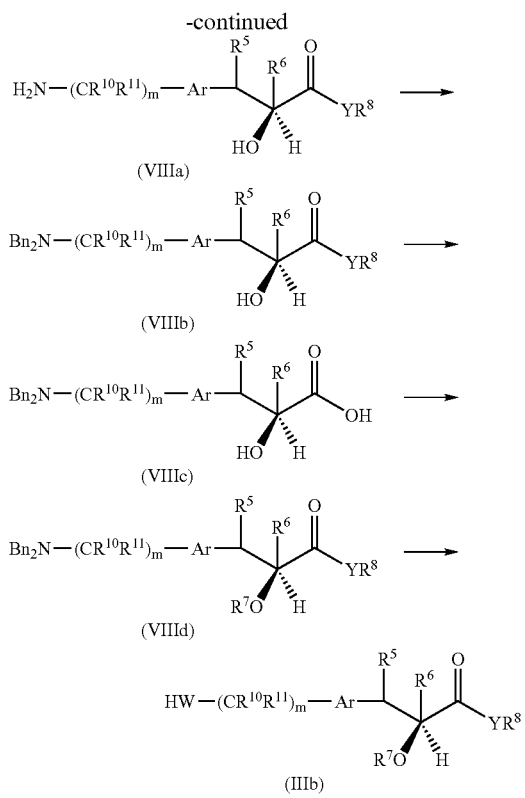

The diazotization of the compound of formula (VIIa) where all symbols are as defined above to obtain a compound of formula (VIIb) may be carried out using diazotizing agents such as sodium nitrate, isoamyl nitrite, potassium nitrite, ammonium nitrite and the like under aqueous acidic conditions using acids such as sulfuric acid, hydrochloric acid, acetic acid and the like, in presence of an optional co solvent like alcohols such as methanol, ethanol, propanol and the like; or ethers such as 1,4-dioxane, THF, and the like; or ketones such as acetone, methyl ethyl ketone and the like.

Esterification of the compound of formula (VIIb) to a compound of formula (VIIc) may be done using an appropriate alcohol of formula $R^8$—OH where $R^8$ represents lower alkyl groups such as methyl, ethyl, propyl, isopropyl, n-butyl, t-butyl and the like in presence of suitable catalyst such as, conc. sulfuric acid, dry HCl, $BF_3$—$OEt_2$, and the like. The reaction may be carried out at reflux temperature of the alcohol employed. Alternatively reagents like diazomethane or $Et_3O^+BF_4^-$ or $Me_3O^+BF_4^-$ and the like may also be used for esterification.

Reduction of compound of the formula (VIIc) to a compound of formula (VIIIa), may be carried out in the presence of gaseous hydrogen or hydrogen donors such as ammonium formate, cyclohex-1,4-diene and the like and a catalyst such as Pd/C, Rh/C, Pt/C, Raney nickel and the like. Mixture of catalysts may be used in the presence of solvents such as methanol, ethanol, dioxane, acetic acid, ethyl acetate and the like. A pressure between atmospheric pressure to 80 psi may be employed. The catalyst may be preferably 5-10% Pd/C and the amount of catalyst used may range from 1-50% w/w. Alternatively, the reaction may also be carried out by employing metal solvent reduction such as magnesium, iron, tin, samarium, indium, sodium amalgam in alcohol, or other suitable solvents preferably methanol.

N,N-dibenzylation of the compound of formula (VIIIa) to the compound of formula (VIIIb) may be done using benzyl halides such as benzyl bromide, benzyl chloride and the like in solvents such as hydrocarbons like toluene, benzene and the like or acetonitrile, tetrahydro furan, dimethyl formamide, dimethyl sulfoxide, and the like, in the presence of alkali bases such as sodium carbonate, potassium carbonate, sodium or potassium hydroxide and the like. Phase transfer catalysts such as tetraalkylammonium hydroxide or tetraalkylammonium halides such as tetrabutylammonium chloride, tetrabutylammonium bromide and the like may also be employed. The reaction may be carried out in the range of room temperature to the reflux temperature of the solvent employed.

Hydrolysis of the compound of the formula (VIIIb) to the compound of formula (VIIIc) using aqueous alkali metal bases such as lithium carbonate, sodium carbonate, potassium carbonate or potassium bicarbonate, lithium hydroxide, sodium hydroxide or potassium hydroxide and the like, in suitable co-solvents such as methanol, ethanol, THF and like or mixtures thereof. The reaction time may range from 0.5 h to 24 h, preferably 0.5 h to 3-4 h and reaction temperature may range from 0° C. to 80° C.

One pot esterification and etherification of the compound of the formula (VIIIc) to the compound of formula (VIIId) where $R^5=R^6$, may be done by treating with bases such as sodium hydride, potassium hydride, sodium hydroxide, potassium hydroxide, sodium carbonate, potassium carbonate and the like, in solvents such as hydrocarbons like toluene, benzene and the like, dialkyl ethers such as diethyl ether, tetrahydro furan and the like or dimethyl formamide, HMPA followed by treatment with alkyl halides such as ethyl iodide, methyl iodide, n-propyl iodide, n-propyl bromide, isopropyl iodide and the like, or alkyl sulfates such as diethyl sulfate, dimethyl sulfate and the like or alkylating agents such as $Et_3O^+BF_4^-$, $Me_3O^+BF_4^-$ and the like. The reaction time may range from 2 h to 20 h and reaction temperature may range from 0° C. to 80° C.

Debenzylation of the compound of the formula (VIIId) to the compound of formula (IIIb) may be carried out in the presence of gaseous hydrogen or hydrogen donors such as ammonium formate, cyclohex-1,4-diene and the like and a catalyst such as Pd/C, Rh/C, Pt/C, Raney nickel and the like. Mixture of catalysts may be used in the presence of solvents such as methanol, ethanol, dioxane, acetic acid, ethyl acetate and the like. A pressure between atmospheric pressure and 80 psi may be employed. The catalyst may be preferably 5-10% Pd/C and the amount of catalyst used may range from 1-50% w/w.

The novel intermediate of formula (IIIb) where W represents $NR^{12}$ and $R^{12}$ represents hydrogen that can be used to prepare the compounds of the present invention and process for preparing the intermediate (IIIb) is described and claimed in our PCT application entitled "Novel β-phenyl-α-oxysubstituted propionic derivatives: process for its preparation and their use in the preparation of pharmaceutically important compounds." filed on the same day as this application.

In still another embodiment of the present invention the novel intermediate of formula (IIId)

(IIId)

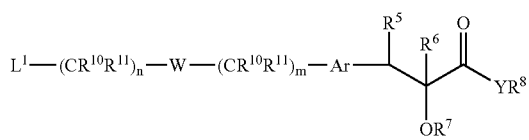

their derivatives, their analogs, their tautomeric forms, their stereoisomers, their polymorphs, their pharmaceutically acceptable salts, their pharmaceutically accept solvates wherein $L^1$ is a leaving group such as halogen atom, methanesulfonate, trifluoromethanesulfonate, p-toluenesulfonate, p-nitrobenznensulfonate, acetate, sulfate, phosphate or hydroxy; W represents $NR^{12}$, $—C(=O)—(CR^{10}R^{11})_o—NR^{12}$, $—O-aryl-(CR^{10}R^{11})_o—NR^{12}$, where $R^{12}$ represents hydrogen or substituted or unsubstituted group selected from alkyl, aryl or aralkyl groups; o is an integer ranging from 0-4; $R^{10}$ and $R^{11}$ may be same or different and represent hydrangea or unsubstituted or unsubstituted group selected form alkyl, alkoxy, aryl or aralkyl group; Ar represents substituted or unsubstituted divalent single or fused aromatic or heterocyclic group; $R^5$ represents hydrogen atom, hydroxy, alkoxy, halogen, alkyl, substituted or unsubstituted aralkyl group or forms a bond together with the adjacent group $R^6$; $R^6$ represents hydrogen, hydroxy, alkoxy, halogen, lower alkyl group, acyl, substituted or unsubstituted aralkyl or $R^6$ forms a bond together with $R^5$; $R^7$ may be hydrogen or substituted or unsubstituted groups selected from alkyl, cycloalkyl, aryl, aralkyl, alkoxyalkyl, alkoxycarbonyl, aryloxycarbonyl, alkylaminocarbonyl, arylaminocarbonyl, acyl, heterocyclyl, heteroaryl, heteroaralkyl groups; $R^8$ may be hydrogen or substituted or unsubstituted groups selected from alkyl, cycloalkyl, aryl, aralkyl heterocyclyl, heteroaryl or heteroaralkyl groups; Y represents oxygen, sulfur or $NR^9$, where $R^9$ represents hydrogen or substituted or unsubstituted groups selected from alkyl, aryl, hydroxyalkyl, aralkyl heterocyclyl, heteroaryl, or heteroaralkyl groups; $R^8$ and $R^9$ together may form a substituted or unsubstituted 5 or 6 membered cyclic structure containing carbon atoms, which may optionally contain one or more heteroatoms selected from oxygen, sulfur or nitrogen; m and n are integers ranging from 0-6 is provided.

In yet another embodiment of the present invention the novel intermediate of formula (IIIg)

(IIIg)

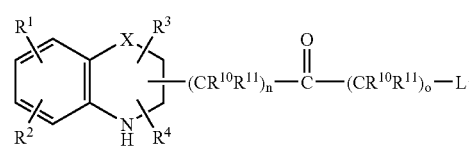

their derivatives, their analogs, their tautomeric forms, their stereoisomers, their polymorphs, their pharmaceutically acceptable salts, their pharmaceutically acceptable solvates wherein $R^1$, $R^2$ and $R^3$, $R^4$ when attached to the carbon atom, may be same or different and represent hydrogen, halogen, hydroxy, nitro, cyano, formyl or substituted or unsubstituted groups selected from alkyl, cycloalkyl, alkoxy, cycloalkoxy, aryl, aryloxy, aralkyl, aralkoxy, heterocyclyl, heteroaryl, heteroaralkyl, heteoaryloxy, heteroaralkoxy, acyl, acyloxy, hydroxyalkyl, amino, acylamino, monoalkylamino, dialkylamino, arylamino, aralkylamino, alkoxycarbonyl, aryloxycarbonyl, aralkoxycarbonyl, alkoxyalkyl, aryloxyalkyl, aralkoxyalkyl, alkylthio, thioalkyl, alkoxycarbonylamino, aryloxycarbonylamino, aralkoxycarbonylamino, carboxylic acid or is derivatives, or sulfonic acid or its derivatives; one or both of $R^3$ and $R^4$ may represent oxo or thioxo group when they are attached to carbon atom; $R^3$ and $R^4$ when attached to nitrogen atom represent hydrogen, hydroxy, formyl or optionally substituted groups selected from alkyl, cycloalkyl, alkoxy, cycloalkoxy, aryl, aralkyl, heterocyclyl, heteroaryl, heteroaralkyl, acyl, acyloxy, hydroxyalkyl, amino, acylamino, monoalkylamino, dialkylamino, arylamino, aralkylamino, aminoalkyl, aryloxy, aralkoxy, heteroaryloxy, heteroaralkoxy, alkoxycarbonyl, aryloxycarbonyl, aralkoxycarbonyl, alkoxyalkyl, aryloxyalkyl, aralkoxyalkyl, alkylthio, thioalkyl groups, carboxylic acid derivatives, or sulfonic acid derivatives; X represents a heteroatom selected from oxygen or sulfur, $R^{10}$ and $R^{11}$ may be same or different and represent hydrogen or substituted or unsubstituted group selected form alkyl, alkoxy, aryl or aralkyl group; $L^1$ is a leaving group such as halogen atom, methanesulfonate, trifluoromethanesulfonate, p-toluenesulfonate, p-nitrobenznensulfonate, acetate, sulfate, phosphate or hydroxy; n and o are integer ranging from 0-6 is provided.

In yet another embodiment of the present invention the novel intermediate of formula (IIIi)

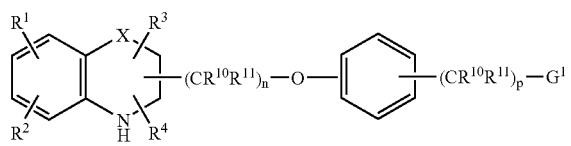

(IIIi)

their derivatives, their analogs, their tautomeric forms, their stereoisomers, their polymorphs, their pharmaceutically acceptable salts, their pharmaceutically acceptable solvates wherein $R^1$, $R^2$ and $R^3$, $R^4$ when attached to the carbon atom, may be same or different and represent hydrogen, halogen, hydroxy, nitro, cyano, formyl or substituted or unsubstituted groups selected from alkyl, cycloalkyl, alkoxy, cycloalkoxy, aryl, aryloxy, aralkyl, aralkoxy, heterocyclyl, heteroaryl, heteroaralkyl, heteroaryloxy, heteroaralkoxy, acyl, acyloxy, hydroxyalkyl, amino, acylamino, monoalkylamino, dialkylamino, arylamino, aralkylamino, alkoxycarbonyl, aryloxycarbonyl, aralkoxycarbonyl, alkoxyalkyl, aryloxyalkyl, aralkoxyalkyl, alkylthio, thioalkyl, alkoxycarbonylamino, aryloxycarbonylamino, aralkoxycarbonylamino, carboxylic acid or its derivatives, or sulfonic acid or its derivatives; one or both of $R^3$ and $R^4$ may represent oxo or thioxo group when they are attached to carbon atom; $R^3$ and $R^4$ when attached to nitrogen atom represent hydrogen, hydroxy, formyl or optionally substituted groups selected from alkyl, cycloalkyl, alkoxy, cycloalkoxy, aryl, aralkyl, heterocyclyl, heteroaryl, heteroaralkyl, acyl, acyloxy, hydroxyalkyl, amino, acylamino, monoalkylamino, dialkylamino, arylamino, aralkylamino, aminoalkyl, aryloxy, aralkoxy, heteroaryloxy, heteroaralkoxy, alkoxycarbonyl, aryloxycarbonyl, aralkoxycarbonyl, alkoxyalkyl, aryloxyalkyl, aralkoxyalkyl, alkylthio, thioalkyl groups, carboxylic acid derivatives, or sulfonic acid derivatives; X represents a heteroatom selected from oxygen or sulfur, $R^{10}$ and $R^{11}$ may be same or different and represent hydrogen or substituted or unsubstituted group selected form alkyl, alkoxy, aryl or aralkyl group; $G^1$ is CHO or $NH_2$ is provided, n and p are integer ranging from 0-6.

It is appreciated that in any of the above mentioned reactions, any reactive group in the substrate molecule may be protected according to conventional chemical practice. Suitable protecting groups in any of the above mentioned reactions are tertiarybutyl dimethyl silylchloride, methoxymethyl chloride etc, to protect hydroxyl group, N-Boc, N-Cbz, N-Fmoc etc, for protection of amino group, acetal protection for aldehyde, ketal protection for ketone and the like. The methods of formation and removal of such protecting groups are those conventional methods appropriate to the molecule being protected.

The pharmaceutically acceptable salts are prepared by reacting the compound of formula (I) with 1 to 4 equivalents of a base such as sodium hydroxide, sodium methoxide, sodium hydride, potassium hydroxide, potassium t-butoxide, calcium hydroxide, magnesium hydroxide and the like, in solvents like ether, THF, methanol t-butanol, dioxane, isopropanol, ethanol, toluene etc. Mixtures of solvents may be used. Organic bases like lysine, arginine, diethanolamine, choline, guanidine, adamentyl amine and their derivatives etc. may also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid, salicylic acid, hydroxynaphthoic acid, ascorbic acid, palmitic acid, succinic acid, benzoic acid, bezenesulfonic acid, tartaric acid and the like in solvents like ethyl acetate, ether, alcohols, acetone, THF, dioxane acid the like. Mixtures of solvents may also be used.

The stereoisomers of the compounds forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, resolving the diastereomeric salts formed with chiral acids such as mandelic acid, camphorsulfonic acid, tartaric acid, lactic acid, and the like wherever applicable or chiral bases such as brucine, cinchona alkaloids and their derivatives and the like. Commonly used methods are complied by Jaques et al in "Enantiomers, Racemates and Resolution" (Wiley Interscience, 1981). More specifically the compound of formula (I) where $YR^8$ represents OH may be converted to a 1:1 mixture of diastereomeric amides by treating with chiral amines, amino acids, amino alcohols derived from aminoacids; conventional reaction conditions may be employed to convert acid into an amide; the diastereomers may be separated either by fractional crystallization or chromatography and the stereoisomers of compound of formula (I) may be prepared by hydrolyzing the pure diastereomeric amide.

Pharmaceutically acceptable solvates of the compounds of formula (I) forming part of this invention may be prepared by conventional methods such as dissolving the compound of formula (I) in solvents such as water, methanol, ethanol and the like, preferably water and recrystallizing by using different crystallization techniques.

Various polymorphs of a compound of general formula (I) forming part of this invention may be prepared by crystallization of compound of formula (I) under different conditions. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffraction or such other techniques.

The present invention provides a pharmaceutical composition, containing the compounds of the general formula (I) as defined above, their derivatives, their analogs, their tautomeric forms, their stereoisomers, their polymorphs, their pharmaceutically acceptable salts or their pharmaceutically acceptable solvates in combination with the usual pharmaceutically employed carriers, diluents and the like, useful for the treatment and/or prophylaxis of diseases such as hypertension, coronary heart disease, atherosclerosis, stroke, peripheral vascular diseases and related disorders. These compounds are useful for the treatment of hyperlipidemia, hyperglycemia, familial hypercholesterolemia, hypertriglyceridemia, lowering of atherogenic lipoproteins, VLDL and LDL. The compounds of the present invention can be used for the treatment of certain renal diseases including glomerulonephritis, glomerulosclerosis, nephrotic syndrome, hypertensive nephrosclerosis, nephropathy. The compounds of general formula (I) are also useful for the treatment/prophylaxis of insulin resistance (type II diabetes), leptin resistance, impaired glucose tolerance, dyslipidemia, disorders related to syndrome X such as hypertension, obesity, insulin resistance, coronary heart disease, and other cardiovascular disorders. These compounds may also be useful as aldose reductase inhibitors, for improving cognitive functions in dementia, treating diabetic complications, disorders related to endothelial cell activation, psoriasis, polycystic ovarian syndrome (PCOS), inflammatory bowel diseases, osteoporosis, myotonic dystrophy, pancreatitis, retinopathy, arteriosclerosis, xanthoma, inflamation and for the treatment of cancer. The compounds of the present invention are useful in the treatment and/or prophylaxis of the above said diseases in combination/concomittant with one or more HMG CoA reductase inhibitors; cholesterol absorption inhibitors; antiobesity drugs; lipoprotein disorder treatment drugs; hypoglycemic agents: insulin; biguanides; sulfonylureas; thiazolidinediones; dual PPARα and γ or a mixture thereof. The compounds of the present invention combination with HMG CoA reductase inhibitors, cholesterol absorption inhibitors, antiobesity drugs, hypoglycemic agents can be administered together or within such a period to act synergistically.

The present invention also provides a pharmaceutical composition, containing the compounds of the general formula (I) as defined above, their derivatives, their analogs, their tautomeric forms, their stereoisomers, their polymorphs, their pharmaceutically acceptable salts or their pharmaceutically acceptable solvates and one or more HMG CoA reductase inhibitors; cholesterol absorption inhibitors; antiobesity drugs; lipoprotein disorder treatment drugs; hypoglycemic agents: insulin; biguanides; sulfonylureas; thiazolidinediones; dual PPARα and γ or a mixture thereof in combination with the usual pharmaceutically employed carriers, diluents and the like.

The pharmaceutical composition may be in the forms normally employed, such as tablets, capsules, powders, syrups solutions, suspensions and the like, may contain flavorants, sweeteners etc. in suitable solid or liquid carries or diluents, or in suitable sterile media to form injectable solutions or suspensions. Such compositions typically contain from 1 to 20%, prefetably 1 to 10% by weight of active compound, the remainder of the composition being pharmaceutically acceptable carriers, diluents or solvents.

Suitable pharmaceutically acceptable carriers include solid fillers or diluents and sterile aqueous or organic solutions. The active ingredient will be present in such pharmaceutical compositions in the amounts sufficient to provide the desired dosage in the range as described above. Thus, for oral administration, the compound of formula (I) can be combined with a suitable solid or liquid carrier or diluent to form capsules, tablets, powders, syrups, solutions, suspensions and the like. The pharmaceutical compositions, may, if desired, contain additional components such as flavourants, sweeteners, excipients and the like. For parenteral administration, the polymorphic form can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable acid addition salts or salts with base of the compounds. Aqueous solutions with the active ingredient dissolved in polyhydroxylated castor oil may also be used for injectable solutions. The injectable solutions prepared in this manner can then be administered intravenously, intraperitoneally, subcutaneously, or intramuscularly, with intramuscular administration being preferred in humans.

For nasal administration, the preparation may contain the polymorphic forms of the present invention dissolved or suspended in a liquid carrier, in particular an aqueous carrier, for aerosol application. The carrier may contain additives such as solubilizing agents, such as propylene glycol, surfactants, absorption enhancers such as lecithin (phosphatidylcholine) or cyclodextrin or preservatives such as parabenes.

Tablets, dragees or capsules having talc and/or a carbohydrate carried binder or the like are particularly suitable for any oral application. Preferably, carriers for tablets, dragees or capsules include lactose, corn starch and/or potato starch. A syrup or elixir can be used in cases where a sweetened vehicle can be employed.

A typical tablet production method is exemplified below:

| Tablet Production Example | |
|---|---|
| a) 1) Active ingredient | 30 g |
| 2) Lactose | 95 g |
| 3) Corn starch | 30 g |
| 4) Carboxymethyl cellulose | 44 g |
| 5) Magnesium stearate | 1 g |
| | 200 g |
| | for 1000 tablets |

The ingredients 1 to 3 are uniformly blended with water and granulated after drying under reduced pressure. The ingredients 4 and 5 are mixed well with the granules and compressed by a tabletting machine to prepare 1000 tablets each containing 30 mg of active ingredient.

| a) 1) Active ingredient | 30 g |
|---|---|
| 2) Calcium phosphate | 90 g |
| 3) Lactose | 40 g |
| 4) Corn starch | 35 g |
| 5) Polyvinyl pyrrolidone | 3.5 g |
| 5) Magnesium stearate | 1.5 g |
| | 200 g |
| | for 1000 tablets |

The ingredients 1 to 4 are uniformly moistened with an aqueous solution of 5 and granulated after drying under reduced pressure. Ingredient 6 is added and granules are compressed by a tabletting machine to prepare 1000 tablets containing 30 mg of ingredient 1.

The compound of formula (I) defined above are clinically administered to mammals, including man, via either oral, nasal, pulmonary, transdermal or parental, rectal, depot, subcutaneous, intravenous, intraurethral, intramuscular, intranasal, ophthalmic solution or ointment. Administration by the oral route is preferred, being more convenient and avoiding the possible pain and irritation of injection. However, in circumstances where the patient cannot swallow the medication, or absorption following oral administration is impaired, as by disease or other abnormality, it is essential that the drug be administered parenterally. By either route, the dosage is in the range of about 0.01 to about 100 mg/kg body weight of the subject per day or preferably about 0.01 to about 30 mg/kg body weight per day administered singly or as divided dose. However, the optimum dosage for the individual subject being treated will be determined by the person responsible for treatment, generally smaller doses being administered initially and thereafter increments made to determine the most suitable dose.

The invention is explained in detail in the examples given below which are provided by way of illustration only and therefore should not be construed to limit the scope of the invention.

Preparation 1

Ethyl 2-ethoxy-3-(4-aminophenyl)propanoate

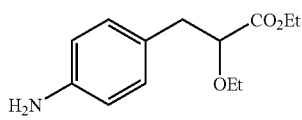

Step (i)

Wittig salt from triethyl 2-ethoxyphosphonoacetate (26.5 g, 1.5 eq, 99.3 mmol) and NaH (50% in oil) (5.3 g, 2 eq, 132.4 mmol) was prepared in THF (350 ml) at 0° C. To this solid 4-nitrobenzaldehyde (10 g, 1 eq, 66.2 mmol) was added in portions at 0° C. and the resulting solution was stirred at RT for 16 h. The reaction mixture was diluted with ethyl acetate and washed with aqueous $NH_4Cl$. The crude contains ethyl 4-nitro-2-ethoxycinnamate in both Z and E stereoisomers (11 g).

Step (ii)

Ethyl 4-nitro-2-ethoxycinnamate obtained in step (i) was hydrogenated using Pd (10%)/C—$H_2$ (60 psi) (11 g) in ethyl acetate (150 ml) at RT and chromatographed using ethyl acetate/hexane to yield the title compound as viscous oil (9.41 g, yield 60%).

$^1$H NMR (200 MHz, $CDCl_3$) δ: 1.16 (t, J=7.0 Hz, 3H), 1.22 (t, J=7.0 Hz, 3H), 2.90 (d, J=6.3 Hz, 2H), 3.30 (bs, 2H, $NH_2$), 3.35 (m, 1H), 3.55 (m, 1H), 3.94 (t, J=6.3 Hz, 1H), 4.15 (q, J=7.0 Hz, 2H), 6.62 (d, J=8.3 Hz, 2H), 7.03 (d, J=8.0 Hz, 2H).

IR (neat) $cm^{-1}$: 3372, 1738.

Mass m/z (CI): 238 (M+1), 192 ($M-OC_2H_5$).

Preparation 2

3-(3,4-Dihydro-2H-benzo[b][1,4]oxazin-4-yl)propyl bromide

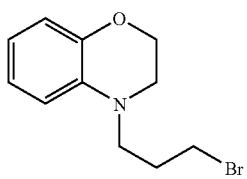

A mixture of 3,4-dihydro-2H-benzo[b][1,4]oxazine (3.0 g, 1 eq, 22.2 mmol), 1,3-dibromopropane (22.5 ml, 10 eq, 222 mmol) and anhydrous sodium carbonate (7.05 g, 3 eq, 66.6 mmol) in dry DMF (200 ml) was heated at 70° C. for 16 h. The reaction mixture was diluted with ethyl acetate and washed with water and brine. The residue was chromatographed using ethyl acetate and hexane to yield the title compounds as liquid mass (2.6 g, 47%).

$^1$H NMR (200 MHz, $CDCl_3$) δ: 2.10-2.30 (m, 2H), 3.37 (t, J=4.4 Hz, 2H) 3.40-3.56 (m, 4H), 4.25 (t, J=4.3 Hz, 2H), 6.60-6.90 (m aromatics, 4H).

Mass m/z (CI): 255 (M($^{79}$Br)), 256 (M($^{79}$Br)+1), 257 (M($Br^{81}$)), 258 (M($Br^{81}$)+1).

Preparation 3

Ethyl 2-ethoxy-3-[4-{N-heptyl-N-(2'-bromoethyl)}aminophenyl]propanoate

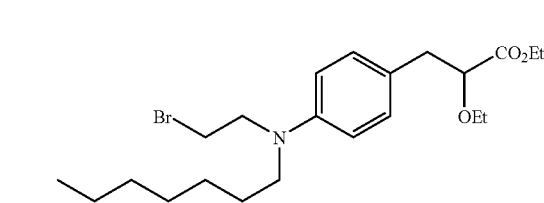

Step (i)

A mixture of ethyl 2-ethoxy-3-(4-aminophenyl)propanoate (5 g, 1 eq, 21 mmol) obtained in preparation 1, heptylbromide (18.8 g, 5 eq, 105 mmol), and anhydrous $K_2CO_3$ (14.5 g, 5 eq, 105 mmol), was heated at 70° C. in DMF (100 ml), for 16 h. The reaction mixture was diluted with ethyl acetate, washed with water and brine. The residue was chromatographed using a mixture of ethyl acetate and hexane as diluent to afford monoheptylated product as thick liquid (3.85 gm, yield 55%).

$^1$H NMR (200 MHz, $CDCl_3$) δ: 0.88 (bt, J=6.3 Hz, 3H), 1.05-1.42 (m 15H), 1.42-1.68 (m, 2H), 2.90 (d, J=6.6 Hz, 2H), 3.08 (t, J=6.8 Hz, 2H), 3.22-2.42 (m, 1H), 3.44-3.64 (m, 1H), 3.94 (t, J=6.8 Hz, 1H), 4.1 (q, J=7.0 Hz, 2H), 6.55 (d, J=8.3 Hz, 2H), 7.04 (d, J=8.31 Hz, 2H).

IR (neat) $cm^{-1}$: 3396, 1747.

Mass m/z (CI): 335 (M+1), 290 ($M-OC_2H_5$).

Step (ii)

The mono heptylated product (3 g, 1 eq, 8.98 mmol) obtained in step (i) was treated with excess dibromoethane (10 eq) in presence of anhydrous $K_2CO_3$ (3.72 g, 3 eq, 27 mmol), in DMF (40 ml), and heated at 70° C. for 16 h. The reaction mixture was diluted with ethyl acetate, washed with water and brine. The residue was chromatographed using a mixture of ethyl acetate and hexane as diluent to yield ethyl 2-ethoxy-3-[4-{N-heptyl-N-(2'-bromoethyl)}aminophenyl]propanoate as thick liquid (1.98 g, yield 50%).

$^1$H NMR (200 MHz, $CDCl_3$) δ: 0.88 (bt, J=6.3 Hz, 3H), 1.05-1.42 (m, 14H), 1.42-1.68 (m, 2H), 2.90 (d, J=6.6 Hz, 2H), 3.28 (t, J=7.3 Hz, 2H), 3.30-3.45 (m, 3H), 3.50-3.70 (m, 3H), 3.96 (t, J=6.8 Hz, 1H), 4.17 (q, J=7.0 Hz, 2H), 6.57 (d, J=8.3 Hz, 2H), 7.09 (d, J=8.3 Hz, 2H).

IR (neat) $cm^{-1}$: 1747.

Mass m/z (CI): 442 (M($^{79}$Br)+1), 444 (M($Br^{81}$)+1).

Preparation 4

2-(3,4-Dihydro-2H-benzo[b][1,4]oxazin-4-yl)carboxymethylchloride

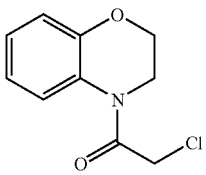

3,4-Dihydro-2H-benzo[b][1,4]oxazine (1.52 g, 1 eq, 11.3 mmol), triethyl amine (4.73 ml, 3 eq, 33.9 mmol) and catalytic amount of DMAP was taken in dry DCM (50 ml). To this mixture 2-chloroacetyl chloride (1.8 ml, 2 eq, 22.6 mmol) was added at 0° C. and the reaction mixture was stirred at 0° C. for 4 h. The reaction mixture was diluted with DCM and washed with dil. aqueous HCl, followed by NaHCO$_3$ and brine. The organic layer was dried over anhydrous Na$_2$SO$_4$ and concentrated on rotavapor. The crude compound was chromatographed using ethyl acetate and hexane to yield the title compounds as waxy solid (1.54 g, yield 65%)

$^1$H NMR (200 MHz, CDCl$_3$) δ: 3.98 (t, J=4.4 Hz, 2H), 4.25-4.40 (m, 4H), 6.90-7.20 (aromatics, 4H).

IR (neat) cm$^{-1}$: 1655.

Mass m/z (CI): 212 (M($^{35}$Cl)$^+$1), 214 (M(Cl$^{37}$)+1).

Preparation 5

Methyl 3-[4-formylphenyl]-2-ethoxypropanoate

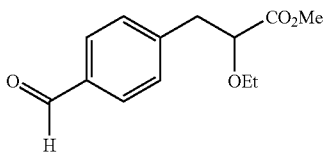

Step (i)

Wittig salt from triethyl 2-ethoxphosphonoacetate (25.6 g, 2.0 eq, 96 mmol) and NaH (3.84 g, 2 eq, 96 mmol) was prepared in THF (240 ml) at 0° C. To this terepthalaldehyde monodiethylacetal (10 g, 1 eq, 48 mmol) was added dropwise at 0° C. The resulting solution was stirred at RT for 24 h. The reaction mixture was diluted with ethyl acetate and washed with aqueous NH$_4$Cl. The residue was chromatographed (ethyl acetate and hexane) to obtain ethyl 4'-(diethoxymethyl)-2-ethoxycinnamate in both Z and E stereoisomers (13.9 g, 90% yield).

Step (ii)

A dry methanolic (20 ml) solution of ethyl 4'-(diethoxymethyl)-2-ethoxycinnamate (5 g, 1 eq, 15.5 mmol), obtained in step (i) was added to dry methanol (6 ml) containing activated magnesium turning (7.44 g, 20 eq, 310 mmol) and was allowed to stir. Eventually the reaction mixture becomes vigorous requiring reflux condenser. Once the magnesium gets consumed to yield Mg(OMe)$_2$ (takes 3-4 h), it was stirred at RT for 16 h. The reaction mixture was acidified carefully with conc HCl stirred for 2 h at RT. Finally ethyl acetate was added and the organic layer was thoroughly washed with water and brine and dried over anhydrous Na$_2$SO$_4$. The residue was chromatographed (EtOAc/hexane) to afford the title compound as viscous oil (2.92 g, yield 80%).

$^1$H NMR (200 MHz, CDCl$_3$) δ: 1.14 (t, J=6.8 Hz, 3H), 3.00-3.20 (m, 2H), 3.22-3.41 (m, 1H), 3.48-3.67 (m, 1H) 3.73 (s, 3H), 4.06 (dd, J=7.8, 5.4 Hz, 1H), 6.40 (d, J=8.3 Hz, 2H), 7.81 (d, J=8.3 Hz, 2H), 9.99 (s, 1H).

IR (neat) cm$^-$: 1751, 1701.

Mass m/z (CI): 237 [M+1].

Preparation 6

Methyl 2-ethoxy-3-[4-(N-heptylaminomethyl)phenyl]propanoate

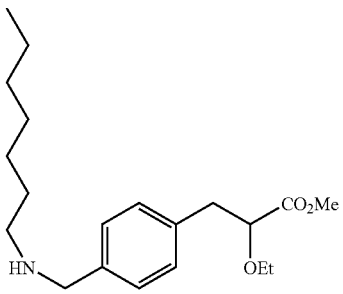

Step (i)

Methyl 3-[4formylphenyl]-2-ethoxypropanoate (2 g, 1 eq, 8.51 mmol) obtained in preparation 5, heptylamine (978 mg, 1 eq, 8.51 mmol) and cat. amount of p-TsOH.H$_2$O were taken in DCM (40 ml), along with few pieces of activated molecular sieves (4 A). The reaction mixture was filtered through celite after 24 h, at RT and the filtrate was diluted with DCM and was washed with aqueous sodium bicarbonate and dried over anhydrous sodium sulfate to yield crude methyl 2-ethoxy-3-[4-(N-heptyliminomethyl)phenyl]propanoate

Step (ii)

The crude methyl 2-ethoxy-3-[4-(N-heptylimiomethyl)phenyl]propanoate obtained in step (i) above (2.95 g), was dissolved in methanol (40 ml), and treated with conc. HCl (850 μl, 1 eq, 8.51 mmol) and sodium cyanoborohydride (535 mg, 1 eq, 8.51 mmol) at 0° C. The progress of the reaction was monitored by TLC. After 2-3 h, the reaction mixture was diluted with ethyl acetate, washed with aqueous sodium bicarbonate and dried over anhydrous sodium sulfate. The residue was chromatographed using methanol and chloroform to afford the title compound (1.71 g, yield 60%) as viscous liquid.

$^1$H NMR (200 MHz, CDCl$_3$) δ: 0.86 (bt, J=6.3 Hz, 3H), 1.14 (t, J=6.8 Hz, 3H), 1.20-1.40 (m, 9H), 1.50-1.70 (m, 2H), 2.60 (t, J=7.4 Hz, 2H), 2.98 (d, J=6.3 Hz 2H), 3.22-3.41 (m, 1H), 3.48-3.67 (m, 1H), 3.71 (s, 3H), 3.89 (s, 2H), 4.02 (t, J=6.3 Hz, 1H), 7.23 (d, J=7.8 Hz, 2H), 7.30 (d, J=7.8 Hz, 2H).

IR (neat) cm$^{-1}$: 3500 (br), 1748.

Mass m/z (CI): 336 [M+1].

Preparation 7

Methyl 2-ethoxy-3-(4-aminophenyl)propanoate

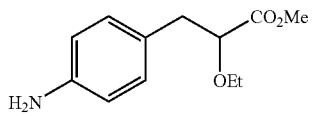

Ethyl 4-nitro2-ethoxycinnamate (10 g, 1 eq, 37.7 mmol) obtained in step (i) of preparation 1, was treated with activated magnesium turnings (18 g, 20 eq, 754 mmol) in dry methanol (400 ml). The reaction mixture was refluxed for 2-3 h, and allowed to stir at room temperature for 16 h. The reaction mixture was diluted with ethyl acetate and quenched with cold aqueous ammonium chloride. The organic layer was washed with water and brine. The residue was chromatographed using ethyl acetate and hexane to afford the title compound as liquid (6 g, yield 72%).

$^1$H NMR (200 MHz, CDCl$_3$) δ: 1.64 (t, J=, 6.8 Hz, 3H), 2.90 (d, J=6.3 Hz, 2H), 3.22-3.42 (m, 1H), 3.42-3.65 (m, 2H), 3.70 (s, 3H), 3.96 (t, J=6.8 Hz, 1H), 6.61 (d, J=8.3 Hz, 2H), 7.00 (d, J=8.3 Hz, 2H).

IR (neat) cm$^{-1}$: 3350 (br), 1735.

Mass m/z (CI): 224 [M+1].

Preparation 8

5-(3,4-Dihydro-2H-benzo[b][1,4]oxazin-4-yl)-5-oxopentyl bromide

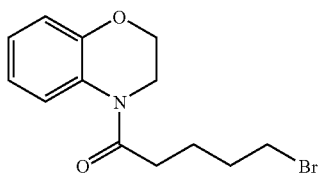

Step (i)

To a mixture of 5-bromo pentanoic acid (4.63 g, 1 eq, 25.6 mmol) and oxalyl chloride (11.2 ml, 5 eq, 128 mmol) in hexane (5 ml), DMF (10 μl) was added and the reaction mixture was heated at 70° C. for 3 h. The excess oxalyl chloride and hexane were removed by distillation and the residue was distilled under high vacuum to yield 5-bromo pentanoyl chloride as light yellow liquid (2.1 g, yield 41%).

Step (ii)

To a solution of 3,4-dihydro-2H-benzo[b]oxazine (500 mg, 1 eq, 3.7 mmol), triethylamine (1.54. ml, 3 eq, 11.1 mmol) and catalytic amount of DMAP in dry DCM (20 ml) was added 5-bromo pentanoyl chloride (870 μl, 2 eq, 7.40 mmol) at 0° C. The reaction mixture was stirred at 0° C. for 4 h and then diluted with excess ethyl acetate. The ethyl acetate layer was washed with dil. HCl, water and then with brine. The residue was chromatographed with ethyl acetate and hexane to yield the title compound liquid (535 mg, yield 53%) as viscous liquid.

$^1$H NMR (200 MHz, CDCl$_3$) δ: 1.70-2.00 (m, 4H), 2.63 (bt, J=5.9 Hz, 2H), 3.39 (t, J=5.8 Hz, major rotamer 1.2H), 3.53 (t, J=6.3 Hz, minor rotamer 0.8H), 3.94 (t, J=4.4 Hz, 2H), 4.29 (t, J=4.9 Hz, 2H), 6.80-7.20 (aromatics, 4H).

IR (neat) cm$^{-1}$: 2936, 1660.

Mass m/z (CI): 298 [M($^{79}$Br)+1], 300 [M($^{81}$Br)+1].

Preparation 9

Methyl 2-ethoxy-3-(3-aminophenyl)propanoate

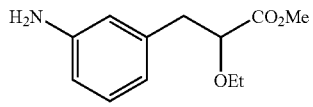

Step (i)

Wittig salt from triethyl 2-ethoxyphosphonoacetate (34.3 ml, 2 eq, 132 mmol) and NaH (50% in oil) (6.28 g, 2 eq, 132 mmol) was prepared in THF (350 ml) at 0° C. To this solid 3-nitrobenzaldehyde (10 g, 1 eq, 66 mmol) was added in portions at 0° C. The resulting solution was stirred at RT for 16 h. The reaction mixture was diluted with ethyl acetate and washed with aqueous NH$_4$Cl. The crude contains ethyl 4-nitro-2-ethoxycinnamate in both Z and E stereoisomers (15 g, yield 86%).

Step (ii)

The crude compound (15 g, 1 eq, 56.6 mmol) obtained it step (i) was dissolved in methanol (250 ml). To this ammonium formate (35.6 g, 10 eq, 566 mmol) and 10% Pd/C (40 g) was added and the reaction was stirred at RT for 16 h. The catalyst was filtered and the methanol was condensed on rotavapour. The reaction was diluted with ethyl acetate and washed with water and brine. The residue was chromatographed to yield methyl 2-ethoxy meta amino cinnamate as (E) and (Z) isomers (10 g, yield 75%).

Step (iii)

Methyl 2-ethoxy meta amino cinnamate (10 g, 1 eq, 42.5 mmol) obtained in step (ii) was treated with magnesium (20.4 g, 20 eq, 850 mmol) and dry methanol (500 ml). The reaction mixture was refluxed for 2-3 h, and allowed to stir at room temperature for 16 h. The reaction mixture was diluted with ethyl acetate and quenched with cold aqueous ammonium chloride. The organic layer was washed with water and brine. The residue was chromatographed using ethyl acetate and hexane to afford the title compound as viscous liquid (8.06 g, yield 80%).

$^1$H NMR (200 MHz, CDCl$_3$) δ: 1.15 (t, J=6.8 Hz, 3H), 2.96 (d, J=6.9 Hz, 2H), 3.22-3.42 (m, 1H), 3.42-3.65 (m, 2H), 3.70 (s, 3H), 4.01 (t, J=6.4 Hz, 1H) 6.50-6.62 (aromatics, 3H), 7.06 (t, J=7.8 Hz, 1H).

IR (neat) cm$^{-1}$: 3360, 1738.

Mass m/z (CI): 224 (M+1).

Preparation 10

3-(7-Fluoro-3,4-dihydro-2H-benzo[b][1,4]oxazin-4-yl)propylbromide

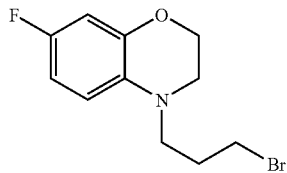

Step (i)

To a solution of 2-nitro-5-fluorophenol (5 g, 1 eq, 31.6 mmol) and ethyl 2-bromoacetate (3.8 ml, 1.1 eq, 34.8 mmol) in dry acetone (160 ml) was added anhydrous potassium carbonate (8.7 g, 2 eq, 63.2 mmol) and stirred at RT for 16 h. The reaction mixture was filtered through celite and then condensed on rotavapour. The residue, was diluted with ethyl acetate and washed with water and brine to yield crude compound (6 g, yield 78%), which was used in step (ii).

Step (ii)

The crude compound obtained in step (i) (6 g, 1 eq, 28.8 mmol) was taken in dry methanol (150 ml). To this iron powder (8.06 g, 5 eq, 144 mmol) and glacial acetic acid (25 ml, 15 eq, 432 mmol) was added and heated at 110° C. for 4 h. The solvents were removed from the reaction mixture and diluted with ethyl acetate. The ethyl acetate layer was washed with aqueous ammonium chloride, water and brine. The residue was chromatographed to yield 3-oxo-7-fluoro-3,4-dihydro-2H-benzo[b][1,4]oxazine as solid (2.2 g, mp: 204-206° C., yield 46%).

$^1$H NMR (200 MHz, CDCl$_3$+DMSO-d$_6$) δ: 4.52 (s, 2H), 6.60-6.70 (m, 2H), 6.88 (dd, J=8.3 and 5.8 Hz, 1H), 10.63 (bs, 1H).

IR (KBr) cm$^{-1}$: 1677, 1622.

Mass m/z (CI): 168 (M+1).

Step (iii)

3-Oxo-7-fluoro-3,4-dihydro-2H-benzo[b][1,4]oxazine (2.2 g, 1 eq, 13.1 mmol) obtained in step (ii) in dry THF (10 ml) was added drop wise to a refluxing THF (60 ml) containing LAH (1.5 g, 3 eq, 39.5 mmol). It was further refluxed for 3 h and quenched with ethyl acetate. To this water (1.5 ml), 15% sodium hydroxide (1.5 ml) and water (4.5 ml) were added sequentially. Once Al(OH)$_3$.H$_2$O precipitated out, it was filtered though celite. The filtrate was condensed on rotavapour and chromatographed (ethyl acetate and hexane) to yield 7-fluoro-3,4-dihydro-2H-benzo[b][1,4]oxazine (1.3 g, yield 65%) as yellow oil.

$^1$H NMR (200 MHz, CDCl$_3$) δ: 2.80 (bs, 1H), 3.38 (t, J=4.4 Hz, 2H), 4.24 (t, J=4.4 Hz, 2H), 6.48-6.56 (aromatics, 3H).

IR (neat) cm$^{-1}$: 3395 (br), 2957, 1606.

Mass m/z (CI): 154 (M+1).

Step (iv)

A mixture of 7-fluoro-3,4-dihydro-2H-benzo[b][1,4]oxazine (1.3 g, 1 eq, 8.49 mmol) obtained in step (iii) above, 1,3-dibromo propane (8.6 ml, 10 eq, 84.9 mmol) and anhydrous sodium carbonate (2.7 g, 3 eq, 25.4 mmol) in dry DMF (85 ml) was heated at 70° C. for 16 h. The reaction was diluted with ethyl acetate and washed with water and brine. The residue was chromatographed using ethyl acetate and hexane to afford the title compound (1.1 g, yield 47%) as viscous oil.

$^1$H NMR (200 MHz, CDCl$_3$) δ: 2.10-2.28 (m, 2H), 3.30 (t, J=4.4 Hz, 2H), 3.38 (t, J=6.7 Hz, 2H), 3.49 (t, J=6.2 Hz, 2H), 4.24 (t, J=4.4 Hz, 2H), 6.50-6.70 (aromatics, 3H).

Mass m/z (CI): 274 [M($^{79}$Br)+1], 276 [M($^{81}$Br)+1].

Preparation 11

N-{(3,4-Dihydro-2H-benzo[b]oxazin-4-yl)propyl}benzylamine

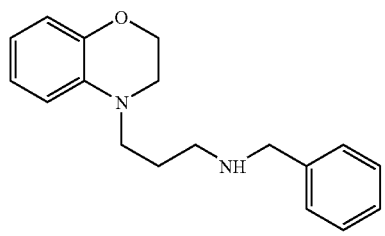

Cesium hydroxide monohydrate (288 mg, 1.1 eq, 1.72 mmol), and grinded molecular sieves 4A (500 mg) was stirred at RT in dry DMF (7 ml) for 15 min. To this benzylamine (510 μl, 3 eq, 4.68 mmol), was added, followed by stirring for another 30 min. Finally 3-(3,4-dihydro-2H-benzo[b][1,4]oxazine-4-yl)propyl bromide (400 mg, 1 eq, 1.50 mmol) obtained in preparation 2, in DMF (3 ml) was added. After stirring for 16 h at RT, the reaction mixture was diluted with ethyl acetate and washed with water and brine. The organic layer was condensed and chromatographed using chloroform/methanol to obtain the title compound as viscous liquid (307 mg, yield 70%).

$^1$H NMR (200 MHz, CDCl$_3$) δ: 1.77 (q, J=6.8 Hz, 2H), 2.00 (bs, 1H), 2.67 (t, J=7.3 Hz, 2H), 3.20-3.28 (m, 4H), 3.76 (s, 2H), 4.16 (t, J=4.4 Hz, 2H), 6.50-6.82 (aromatics, 4H), 7.18-7.38 (aromatics, 5H).

IR (neat) cm$^{-1}$: 3311 (br), 2931, 1669.

Mass m/z (CI): 283 (M+1).

Preparation 12

Methyl 2-ethoxy-3-{4-(4-hydroxybenzyl)aminophenyl}propanoate

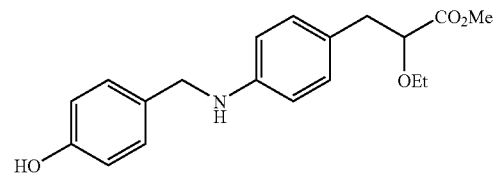

Methyl 2-ethoxy-3-(4-aminophenyl)propanoate (500 mg, 1 eq, 2.24 mmol) obtained in preparation 7, 4-hydroxybenzaldehyde (273 mg, 1 eq, 2.24 mmol), and catalytic amount of p-TsOH were taken in DCM (5 ml) along with few pieces of molecular sieves (4A). The reaction mixture was stirred at RT for 24 h, diluted with excess amount of ethyl acetate and washed with aqueous sodium bicarbonate. The EtOAc layer was dried over anhydrous sodium sulfate and then condensed on rotary evaporator. The crude was dissolved in methanol (10 ml) and treated with Na(CN)BH$_3$ (166 mg, 1.2 eq, 2.64 mmol) in presence of conc. HCl (220 mL) at, 0° C. and stirred for 2 h. The reaction mixture was diluted with excess amount of ethyl acetate, washed with water and brine. The EtOAc layer was dried over anhydrous sodium sulfate and then condensed on rotary evaporator. The residue was chromatographed using EtOAc/hexane to obtain the title compound as solid mass (405 mg, yield 55%, mp: 109-110° C.).

$^1$H NMR (200 MHz, CDCl$_3$) δ: 1.17 (t, J=6.9 Hz, 3H), 2.89 (d, J=6.4 Hz, 2H), 3.22-3.42 (m, 1H), 3.50-3.65 (m, 1H), 3.70 (bs, 5H, CO$_2$Me, —OH, —NH—), 3.98 (t, J=6.8 Hz, 1H), 4.20 (s, 2H), 6.56 (d, J=8.3 Hz, 2H), 6.78 (d, J=8.3 Hz, 2H), 7.03 (d, J=8.3 Hz, 2H), 7.21 (d, J=8.3 Hz, 2H).

IR (KBr) cm$^{-1}$: 3369, 1680.

Mass m/z (CI): 330 [M+1].

Preparation 13

Methyl 2-ethoxy-3-{3-(4-hydroxybenzyl)aminophenyl}propanoate

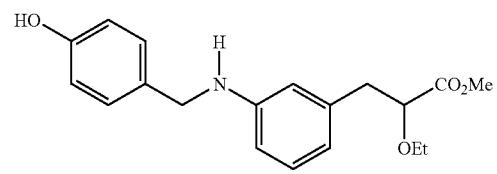

Methyl 2ethoxy-3-(3-aminophenyl)propanoate (1.0 mg, 1 eq., 4.4 mmol), obtained in preparation 9, 4-hydroxybenzaldehyde (547 mg, 1 eq, 4.4 mmol), and cat. amount of p-TsOH was taken in CH$_2$Cl$_2$ (25 ml) along with few pieces of activated molecular sieves (4A). The reaction was mixture was stirred at RT for 24 h, which was then diluted with excess of ethyl acetate and washed with aqueous sodium bicarbonate. The EtOAc layer was dried over anhydrous sodium sulfate and then condensed on rotary evaporator. The crude was dissolved in MeOH (20 ml), and treated with Na(CN)BH$_3$ (415 mg, 1.5 eq, 6.6 mmol) in presence of conc. HCl (528 mL) at 0° C. After 2 h of stirring, the reaction mixture was again diluted with excess amount of ethyl acetate and washed with water and brine. The EtOAc layer was dried over anhydrous sodium sulfate and then condensed on rotary evaporator. The residue was chromatographed using EtOAc/Hexanes to afford the title compound (450 mg, 30% yield) as viscous liquid.

$^1$H NMR (200 MHz, CDCl$_3$) δ: 1.19 (t, J=7.0 Hz, 3H), 1.29 (s, 1H, N—H), 2.96 (d, J=6.3 Hz, 2H), 3.30-3.50 (m, 1H), 3.50-3.70 (m, 1H) 3.73 (bs, 3H), 4.07 (t, J=6.6 Hz 1H), 4.21 (s, 2H), 6.50-6.70 (m, 3H), 6.81 (d, J=8.3 Hz, 2H) 7.11 (t, J=7.8, 1H), 7.22 (d, J=8.3 Hz, 2H) 7.39 (s, 1H, —OH).

IR (neat) cm$^-$: 3391, 1738, 1607.

Mass m/z (CI): 330 [M+1].

Preparation 14

3-(3,4-Dihydro-2H-benzo[b][1,4]thiazin-4yl)propylbromide

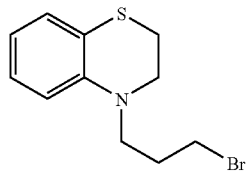

A mixture of 3,4-dihydro-2H-benzo[b][1,4]thiazine (2.0 g, 1.0 eq, 13.24 mmol), 1,3-dibromopropane (14 ml, 10 eq, 132.4 mmol) and anhydrous Na$_2$CO$_3$ (4.21 g, 3.0 eq, 39.7 mmol) in dry DMF (130 ml) was heated at 70° C. for 16 h. The reaction mixture was diluted with ethyl acetate (200 ml) and washed with water and brine. The organic layer was dried (Na$_2$SO$_4$), condensed, and the residue was chromatographed using ethyl acetate and hexanes to obtain the title compound as yellow oil (2.13 g, 59% yield).

$^1$H NMR (200 MHz, CDCl$_3$) δ: 2.11-2.25 (m, 2H), 3.02 (t, J=4.4 Hz, 2H), 3.20-3.28 (m, 4H), 3.62 (t, J=4.4 Hz, 2H), 6.60-6.72 (aromatics, 2H), 6.90-7.20 (aromatics, 2H).

Mass m/z (CI): 271 [M ($^{79}$Br)], 272 [M ($^{79}$Br)+1], 273 [M ($^{81}$Br)], 271 [M ($^{81}$Br)+1].

Preparation 15

2-(3,4-Dihydro-2H-benzo[b][1,4]oxazin-4-yl)ethylbromide

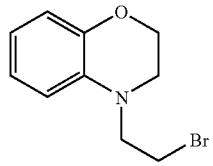

A mixture of 3,4-dihydro-2H-benzo[b][1,4]oxazine (1.5 g, 1.0 eq, 11.12 mmol), 1,3-dibromoethane (10 ml, 10 eq, 111.2 mmol) and anhydrous K$_2$CO$_3$ (4.6 g, 3.0 eq, 33.36 mmol) in dry DMF (110 ml) was heated at 70° C. for 16 h. The reaction mixture was diluted with ethyl acetate (200 ml), washed with water and brine. The organic layer was dried (Na$_2$SO$_4$), condensed, and the residue was chromatographed using ethyl acetate and hexane to obtain the title compound as yellow oil (940 g, 34%).

$^1$H NMR (200 MHz, CDCl$_3$) δ: 3.45 (t, J=4.4 Hz, 2H), 3.50-3.72 (m, 4H), 4.24 (t, J=4.4 Hz, 2H), 6.65 (t, J=7.8 Hz, 2H), 6.78-6.90 (aromatics, 2H).

Mass m/z (CI): 241 [M ($^{79}$Br)], 242 [M ($^{79}$Br)+1], 243 [M ($^{81}$Br)], 244 [M ($^{81}$Br)+1].

Preparation 16

4-{2-(3,4-Dihydro-2H-benzo[b][1,4]oxazin-4-yl)ethoxy}aniline

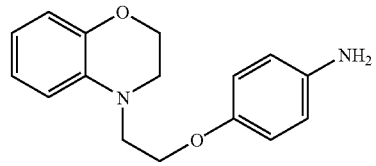

Step (i)

A mixture of 2-(3,4-dihydro-2H-benzo[b][1,4]oxazin-4-yl)ethyl bromide (500 mg, 1.0 eq, 2.07 mmol) obtained it preparation 15, 4-nitrophenol (288 mg, 1 eq, 2.07 mmol) and anhydrous K$_2$CO$_3$ (857 mg, 3.0 eq, 6.21 mmol) in dry acetone (12 ml) was stirred at RT for 16 h. The reaction mixture was diluted with ethyl acetate (200 ml), washed with water and brine. The organic layer was dried (Na$_2$SO$_4$), condensed. The crude mass was used for the step (ii).

Step (ii)

A methanolic solution (10 ml) of the crude product (600 mg, 1 eq, 2.0 mmol), obtained in step (i) was hydrogenated at RT under atmospheric pressure using ammonium formate (2.6 g, 20 eq., 40 mmol) and 10% Pd/C as catalyst (500 mg). After 6 h of stirring TLC indicated absence of starting material. The reaction mixture was filtered through celite and condensed. The residue was chromatographed using ethyl acetate and hexane to obtain the title compound as viscous liquid (355 mg, 66%).

$^1$H NMR (200 MHz, CDCl$_3$) δ: 3.40 (bs, —NH$_2$), 3.51 (t, J=4.4 Hz, 2H), 3.65 (t, J=5.8 Hz, 2H), 4.10 (t, J=5.6 Hz, 2H), 4.23 (t, J=4.4 Hz, 2H), 6.50-6.90 (aromatics, 4H).

Mass m/z (CI): 270 [M], 271 [M+1].

Preparation 17

3(2-methyl-7-Fluoro-3,4-dihydro-2H-benzo[b][1,4]oxazin-4-yl)propylbromide

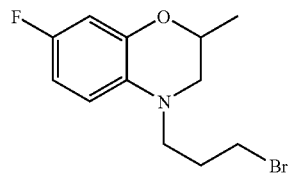

Step (i)

To a solution of 2-nitro-5-fluorophenol (1.0 g, 1 eq, 6.36 mmol) and ethyl 2-bromopropionate (0.91 ml, 1.1 eq, 6.99 mmol) in dry acetone (32 ml) was added anhydrous potassium carbonate (2.63 g, 3 eq, 19.08 mmol) and the reaction mixture was refluxed for 16 h. The reaction mixture was filtered through celite and then condensed on rotavapour. The residue was diluted with ethyl acetate and washed with water and brine to yield ethyl 2-(2-nitro-5-fluorophenoxy)propanoate as crude compound (1.6 g, yield 98%), which was used in step (ii).

Step (ii)

The crude compound obtained in step (i) (1.6 g, 1 eq, 6.22 mmol) was taken in dry methanol (150 ml). To this iron powder (5.23 g, 15 eq, 93.37 mmol) and glacial acetic acid (5.6 ml, 15 eq, 93.37 mmol) was added and heated at 110° C. for 4 h. The solvents were removed from the reaction mixture and diluted with ethyl acetate. The ethyl acetate layer was washed with aqueous ammonium chloride, water and brine. The residue was chromatographed to yield 2-methyl-3-oxo-7-fluoro-3,4-dihydro-2H-benzo[b][1,4]oxazine as solid (1.0 g, yield 88%).

Mp: 166-168° C.

$^1$H NMR (200 MHz, CDCl$_3$) δ: 1.59 (d, J=6.9 Hz, 3H); 4.67 (q, J=6.9 Hz, 1H), 6.60-6.80 (aromatics, 3H), 8.61 (bs, 1H).

IR (KBr) cm$^{-1}$: 1677, 1610.

Mass m/z (CI): 182 (M+1).

Step (iii)

2-Methyl-3-oxo-7-fluoro-3,4-dihydro-2H-benzo[b][1,4]oxazine (4.8 g, 1 eq, 26.5 mmol) obtained in step (ii) in dry THF (60 ml) was added drop wise to a refluxing THF (200 ml) containing LAH (6.05 g, 6 eq, 159.1 mmol). It was further refluxed for 3 h and quenched with ethyl acetate, and hydrolyzed with saturated aq. sodium sulfate. Once Al(OH)$_3$.H$_2$O precipitated out, it was filtered through celite. The filtrate was condensed on rotavapour and chromatographed (ethyl acetate and hexane) to yield 2-methyl-7-fluoro-3,4-dihydro-2H-[b][1,4]oxazine (4.3 g, yield 97%) as yellow oil. The crude product was used fir the next reaction.

$^1$H NMR (200 MHz, CDCl$_3$) δ: 1.36 (d, J=6.5 Hz, 3H); 3.05 (dd, J=11.3, 8.0 Hz, 1H); 3.32 (d, J=11.8 Hz, 1H); 3.60 (bs, 1H, N—H); 4.18-4.30 (m, 1H), 6.40-6.60 (aromatics, 3H).

IR (KBr) cm$^{-1}$: 3387, 2977, 2933, 1605, 1510.

Mass m/z (CI): 168 (M+1).

Step (iv)

A mixture of 2-methyl-7-fluoro-3,4-dihydro-2H-benzo[b][1,4]oxazine (4.3 g, 1 eq, 25.74 mmol) obtained in step (iii) above, 1,3-dibromo propane (26.1 ml, 10 eq, 257 mmol) and anhydrous sodium carbonate (8.2 g, 3 eq, 77.2 mmol) in dry DMF (260 ml) was heated at 70° C. for 16 h. The reaction mixture was diluted with ethyl acetate and washed with water and brine. The residue was chromatographed using ethyl acetate and hexane to afford the title compound (3.5 g, yield 48%) as viscous oil.

$^1$H NMR (200 MHz, CDCl$_3$) δ: 1.35 (d, J=6.7 Hz, 3H); 2.02-2.22 (m, 2H; 3.01 (dd, J=11.3, 8.3 Hz, 1H); 3.32 (dd, J=11.6, 2.3 Hz, 1H); 3.22-3.58 (m, 4H); 4.18-4.35 (m, 1H), 6.42-6.62 (aromatics, 3H).

Mass m/z (CI): 288 [M($^{79}$Br)+1], 290 [M($^{81}$Br)+1].

Preparation 18

3-(2-methyl-3,4-dihydro-2H-benzo[b][1,4]oxazine-4-yl)propylbromide

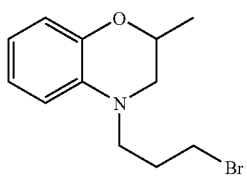

Step (i)

Starting from 2-nitrophenol (10 g, 1 eq, 71.9 mmol) and ethyl 2-bromopropionate (10.2 ml, 1.1 eq, 79.09 mmol) the procedure of Step (i), preparation 17 was followed to obtain ethyl 2-(2-nitrophenoxy)propanoate in crude form (16 g) which was used for step (ii).

Step (ii)

The crude compound obtained in step (i) (16 g, 1 eq, 62.2 mmol) was converted to 2-methyl-3-oxo-3,4-dihydro-2H-benzo[b][1,4]oxazine as solid (10.0 g, yield 98%) following the procedure of step (ii), preparation 17.

Mp: 164-166° C.

$^1$H NMR (200 MHz, CDCl$_3$) δ: 1.59 (d, J=6.7 Hz, 3H); 4.67 (q, J=6.7 Hz, 1H), 6.80-7.00 (aromatics, 4H), 9.45 (bs, 1H).

IR (KBr) cm$^{-1}$: 3500, 3198, 2917, 1675, 1608, 1501.

Mass m/z (CI): 164 (M+1).

Step (iii)

2-Methyl-3-oxo-3,4-dihydro-2H-benzo[b][1,4]oxazine (5.0 g, 1 eq, 30.6 mmol) obtained in step (ii) was reduced to 2-methyl-3,4-dihydro-2H-benzo[b][1,4]oxazine (4.3 g, yield 90%) as yellow oil following the procedure of step (iii), preparation 17.

$^1$H NMR (200 MHz, CDCl$_3$) δ: 1.37 (d, J=6.1 Hz, 3H); 3.10 (dd, J=11.3, 8.1 Hz, 1H); 3.34 (d, J=11.6, 2.5 Hz, 1H); 3.60 (bs, 1H, N—H); 4.18-4.30 (m, 1H), 6.50-6.80 (aromatics, 4H).

IR (KBr) cm$^{-1}$: 3389, 2977, 2976, 1608, 1503.

Mass m/z (CI): 150 (M+1).

Step (iv)

From 2-Methyl-3,4-dihydro-2H-benzo[b][1,4]oxazine (4.5 g, 1 eq, 30.2 mmol) obtained in step (iii) above, and 1,3-dibromo propane (30 ml, 10 eq, 300 mmol) and following the procedure of step (iv), preparation 17 title compound (3.5 g, yield 48%) was obtained as viscous oil.

$^1$H NMR (200 MHz, CDCl$_3$) δ: 1.29 (d, J=6.4 Hz, 3H); 2.05-2.25 (m, 2H); 3.07 (dd, J=11.3, 8.3 Hz, 1H); 3.24 (dd, J=11.6, 2.3 Hz, 1H); 3.30-3.58 (m, 4H); 4.18-4.35 (m, 1H), 6.50-6.82 (aromatics, 4H).

Mass m/z (CI): 270 [M($^{79}$Br)+1], 272 [M($^{81}$Br)+1].

Preparation 19

3-(2propyl-3,4-dihydro-2H-benzo[b][1,4]oxazin-4-yl)propylbromide

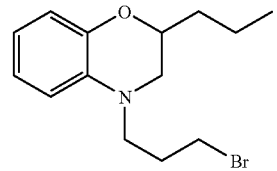

Step (i)

Starting from 2-nitrophenol (1.0 g, 1 eq, 7.19 mmol) and ethyl 2-bromopentanoate (2.97 ml, 3.0 eq, 21.54 mmol) the procedure of step (i), preparation 17 was followed to obtain ethyl 2-(2-nitrophenoxy)pentanoate (2.0 g) as crude which was used for step (ii).

Step (ii)

The crude compound obtained in step (i) (1.7 g, 1 eq, 6.36 mmol) was converted to 2-propyl-3-oxo-3,4-dihydro-2H-benzo[b][1,4]oxazine as solid (1.2 g, yield 87% over 2 steps) following the procedure of step (ii), preparation 17.

Mp: 172-174° C.

$^1$H NMR (200 MHz, CDCl$_3$) δ: 0.98 (d, J=7.0 Hz, 3H); 1.40-1.70 (m, 2H); 1.70-1.98 (m, 2H); 4.59 (t, J=6.4 Hz, 1H); 6.84-700 (aromatics, 4H), 9.00 (bs, 1H).

IR (KBr) cm$^{-1}$: 3198, 2917, 1677, 1611, 1502.

Mass m/z (CI): 192 (M+1).

Step (iii)

2-Propyl-3-oxo-3,4-dihydro-2H-benzo[b][1,4]oxazine (2.0 g, 1 eq, 10.4 mmol) obtained in step (ii) was reduced to 2-propyl-3,4-dihydro-2H-benzo[b][1,4]oxazine (1.65 g, yield 90%) as crude following the procedure of step (iii), preparation 17 and proceeded for the next reaction.

Mass m/z (CI): 178 (M+1).

Step (iv)

From 2-propyl-3,4-dihydro-2H-benzo[b][1,4]oxazine (1.65 g, 1 eq, 9.3 mmol) obtained in step (iii) above, and 1,3-dibromo propane (9.4 ml, 10 eq, 93 mmol) and following the procedure of step (iv), preparation 17 title compound (915 mg, yield 33%) was obtained as viscous oil.

$^1$H NMR (200 MHz, CDCl$_3$) δ: 0.97 (t, J=7.0 Hz, 3H); 1.40-1.80 (m, 4H); 2.00-2.25 (m, 2H); 3.10 (dd, J=11.6, 8.0 Hz, 1H); 3.27 (dd, J=11.6, 2.4 Hz, 1H); 3.35-3.58 (m, 4H); 4.00-4.18 (m, 1H), 6.50-6.90 (aromatics, 4H).

Mass m/z (CI): 298 [M($^{79}$Br)+1], 300 [M($^{81}$Br)+1].

Preparation 20

(S)-Ethyl 2-ethoxy-3-(4-aminophenyl)propionate

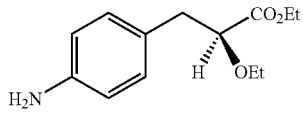

Step (i)

To a solution of (S)-(4-nitrophenyl) alanine (10 g, 47.6 mmol) in a mixture of water (50 mL), H$_2$SO$_4$ (1M, 60 mL) and acetone (150 mL) at −5° C., was added under stirring, a solution of sodium nitrite (9.85 g, 142.8 mmol) in water (40 mL) drop wise over a period of 30 min. The reaction mixture was stirred at −5 to 0° C. for another 1.5 h, followed by stirring at room temperature for 16 h. Acetone was removed and then the reaction mixture was diluted with 500 mL ethyl acetate. Organic layer was washed with brine, dried over anhydrous Na$_2$SO$_4$, and concentrated. The crude mass was purified by crystallization from isopropyl acetate (9.0 g, 96%).

Mp: 134-136° C.

[α]$_D$: −25° (c 1.0, MeOH)

$^1$H NMR (CDCl$_3$) δ: 3.04 (dd, J=14, 7.8 Hz, 1H), 3.24 (dd, J=14, 4, Hz, 1H), 4.39 (dd, J=7.3, 4.1 Hz, 1H), 7.42 (d, J=8.7 Hz,2H), 8.16 (d, J=8.7 Hz, 2H).

IR (neat) cm$^{-1}$: 3485, 3180, 2927, 1715, 1515, 1343.

Mass m/z (CI): 212 (M+1).

Step (ii)

(S)-2-Hydroxy-3-(4-nitrophenyl)propionic acid (9.0 g, 42.6 mmol) obtained from step (i) above, was dissolved in dry EtOH (300 mL). To this solution was added conc. H$_2$SO$_4$ (326 mL, 5.9 mmol), and refluxed for 5 to 6 h. The reaction mixture was neutralized with aqueous sodium bicarbonate. Ethanol was condensed on rotavapor, and the residue was dissolved on ethyl acetate. Organic layer was washed with aqueous sodium bicarbonate, water, brine, and then dried over anhydrous Na$_2$SO$_4$, and concentrated. Desired product was obtained from the crude mass by crystallizing from diisopropylether (8.0 g, 78.5%).

Mp: 74-76° C.

[α]$_D$: −13° (c 1.0, MeOH)

$^1$H NMR (CDCl$_3$) δ: 1.30 (t, J=7 Hz 3H), 3.06 (dd, J=14, 7, Hz, 1H), 3.25 (dd, J=14, 4.3, Hz, 1H), 4.25 (q, J=7 Hz, 2H), 4.25 (dd, J=7, 4.3 Hz, 1H), 7.42 (d, J=8.7 Hz, 2H), 8.16 (d, J=8.7 Hz, 2H).

IR (neat) cm$^{-1}$: 3432, 2924, 1736, 1518, 1347.

Mass m/z (CI): 240 (M+1).

Step (iii)

To a mixture of (S)-Ethyl 2-Hydroxy-3-(4-nitrophenyl) propionate (4.77 g, 19.95 mmol), obtained in step ii above, molecular sieves (4 A) (5.0 g) and powdered Ag$_2$O (13.8 g, 59.8 mmol) in dry acetonitrile (100 mL), was added ethyl iodide (6.4 mL, 79.8 mmol) at room temperature. The reaction mixture was heated at 60° C. for 16 h. The reaction mixture was filtered through celite, and concentrated. The crude mass was chromatographed using ethyl acetate and hexanes to obtain the desired product as viscous liquid (3.5 g, 67% isolated yield). Unreacted starting material was recovered (900 mg which could be reused.

[α]$_D$: −26° (c 1.0, MeOH)

$^1$H NMR (CDCl$_3$) δ: 1.15 (t, J=7 Hz, 3H) 1.26 (t, J=7.1 Hz, 3H); 3.10 (d, J=3.8 Hz 1H); 3.13 (s, 1H); 3.16-3.35 (m, 1H); 3.45-3.65 (m, 1H); 4.03 (dd, J=7,5, 5.4 Hz, 1H); 4.21 (q, J=7.2 Hz, 2H); 7.43 (d, J=8.6 Hz, 2H); 8.15 (d, J=8.6 Hz, 2H).

IR (neat) cm$^{-1}$: 2980, 1747, 1604, 1521, 1347.

Mass m/z (CI): 268 (M+1).

Step (iv)

(S)-Ethyl 2-ethoxy-3-(4-nitrophenyl)propionate (6.0, 25.3 mmol), obtained in step (iii) above, was dissolved in dry methanol (100 mL). To this solution was added 10% Pd/C (2.0 g), and was hydrogenated using hydrogen gas (20 psi) for 3-4 h. The reaction mixture was filtered through celite, and the filtrate was concentrated to provide a syrupy mass. The product was obtained in quantitative yield.

[α]$_D$: −14.2° (c 1.0, MeOH).

Chiral HPLC: >98% ee.

$^1$H NMR (CDCl$_3$) δ: 1.16 (t, J=7.0 Hz, 3H), 1.22 (t, J=7.0 Hz, 3H), 2.90 (d, J=6.3 Hz, 2H), 3.30 (bs, 2H, NH$_2$), 3.24-3.42(m, 1H), 3.50-3.70 (m, 1H), 3.94 (t, J=6.3 Hz, 1H), 4.15 (q, J=7.0 Hz, 2H), 6.62 (d, J=8.3 Hz, 2H), 7.03 (d, J=8.0 Hz, 2H).

IR (neat) cm$^{-1}$: 3372, 1738.

Mass m/z (CI): 238 (M+1), 192 (M−OC$_2$H$_5$).

Preparation 21

(S)-Ethyl 2-methoxy-3-(4-aminophenyl)propionate

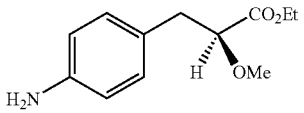

Step (i)

To a mixture of (S)-Ethyl 2-Hydroxy-3-(4-nitrophenyl) propionate (12.5 g, 52.3 mmol), obtained in step (ii) of preparation 20, and powdered Ag$_2$O (36.3 g, 157 mmol) in dry acetonitrile (260 mL) was added methyl iodide (13 mL, 209.2 mmol) at room temperature. Activated molecular sieves (4 A) (12.5 g) were added and then the reaction mixture was stirred at room temperature for 16 h. The reaction mixture was filtered through celite, and concentrated. The crude mass was chromatographed using ethyl acetate and hexanes to obtain the desired product as viscous liquid (10.0 g, 75%).

[α]$_D$: −30.1° (c 1.0, MeOH)

$^1$H NMR (CDCl$_3$) δ: 1.24 (t, J=7.1 Hz, 3H); 3.09 (d, J=5.4 Hz, 1H); 3.12 (d, J=2.7 Hz, 1H); 3.35 (s, 3H); 3.96 (dd, J=7.5, 5.1 Hz, 1H) 4.19 (q, J=7.1 Hz, 2H); 7.39 (d, J=8.6 Hz, 2H); 8.13 (d, J=8.6 Hz, 2H).

IR (neat) cm$^{-1}$: 2995, 1747, 1604, 1521, 1343.

Mass m/z (CI): 254 (M+1).

Step (ii)

(S)-Ethyl 2-methoxy-3-(4-nitrophenyl)propionate (8.0, 31.6 mmol) obtained in step (i) above, was dissolved in dry methanol (200 mL). To this solution was added 10% Pd/C (2.5 g), and hydrogenated using hydrogen gas (20 psi) for 3-4 h. The reaction mixture was filtered through celite, and concentrated to a syrupy mass. After column chromatography using ethyl acetate/hexanes the desired product was isolated as thick liquid (7.0 g, quantitative).

[α]$_D$: −14.1° (c 1.0, MeOH).

Chiral HPLC: >98% ee.

$^1$H NMR (CDCl$_3$) δ: 1.23 (t, J=7.2 Hz, 3H), 2.91 (d, J=6.1 Hz, 2H), 3.30 (bs, 2H, NH$_2$), 3.34 (s, 3H), 3.88 (t, J=6.2 Hz, 1H), 4.17 (q, J=7.2 Hz, 2H), 6.62 (d, J=8.3 Hz, 2H), 7.01 (d, J=8.1 Hz, 2H).

IR (neat) cm$^{-1}$: 3372, 2985, 2932, 1739, 1627, 1519.

Mass m/z (CI): 223 (M), 234 (M+1), 192 (M−OMe).

Preparation 22

Ethyl 2-isopropoxy-3-(4-aminophenyl)propionate

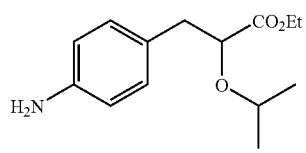

Step (i):

4-nitrophenylalanine (5 g, 1 eq, mmol) was added in portions to a solution of dry ethanol (mL) and thionylchloride (mL) at −5° C. It was stirred at that temperature for another one hour, followed by stirring at RT for 16 h. The reaction mixture was condensed on rotavapour, azeotroped with toluene, and then dried over high vaccum pump to obtain 4-nitrophenylalanine ethyl ester hydrochloride as white solid (quantitative yield).

Step (ii):

4-nitrophenylalanine ethyl ester hydrochloride (2 g, 1.0 eq, 7.28 mmol) obtained in step (i) was dissolved in ethyl acetate (150 mL). To that Na$_2$CO$_3$ (386 mg, 0.5 eq, 3.64 mmol) was added and was stirred for 15 min. The reaction mixture was washed with aq. NaHCO$_3$. The organic layer was dried (Na$_2$SO$_4$), and condensed to obtain 4-nitrophenylalanine ethyl ester as thick oil (1.55 g, 89%).

Step (iii):

4-nitrophenylalanine ethyl ester (1.55 g, 1.0 eq, 6.51 mmol), obtained in step(ii) above was dissolved in chloroform (33 mL). To that glacial acetic acid (20 µL, 0.05 eq, 0.33 mmol), and isoamylnitrite (958 µL, 1.1 eq, 7.16 mmol) were added and the reaction mixture was heated at reflux for 30 min. The reaction mixture was diluted with chloroform, and was washed with aq. NaHCO$_3$. The organic layer was dried (Na$_2$SO$_4$) and condensed (caution!) to a yellowish liquid.

Step (iv):

The liquid (1.54 g, 1.0 eq, 6.18 mmol) thus obtained in step (iii), was dissolved in dry isopropanol (31 mL), and to that catalytic amount of Rh$_2$(OAc)$_4$.2H$_2$O (38 mg, 0.02 eq, 0.12 mmol) was added and the reaction mixture was stirred at room temperature for 16 h. Isopropanol was condensed, and the reaction mixture was diluted with ethyl acetate. The organic layer was washed with water and brine, dried (Na$_2$SO$_4$), and concentrated. Column chromatography, using ethyl acetate and hexanes, provided the desired compound ethyl 2-isopropoxy-3-(4-nitrophenyl)propionate (1.25 g, 61% overall).

$^1$H NMR (200 MHz, CDCl$_3$) δ: 0.92 (d, J=5.8 Hz, 3H), 1.16 (d, J=5.8 Hz, 3H), 1.27 (t, J=7.4 Hz, 3H), 3.00-3.10 (m, 2H), 3.52 (quintet, 1H); 4.08 (dd, J=8.7 and 4.8 Hz, 1H), 4.21 (q, J=7.4 Hz, 2H), 7.43 (d, J=8.7 Hz, 2H), 8.16 (d, J=8.7 Hz, 2H).

IR (neat) cm$^{-1}$: 2975, 1747, 1602, 1522, 1347.

Mass m/z (CI): 282 [M+1]

Step (v):

Ethyl 2-isopropoxy-3-(4-nitropohenyl)propionate (1.52 g, 5.4 mmol) obtained in step (v) was hydrogenated under 10 psi pressure of molecular hydrogen using 10% Pd/C (700 mg) as catalyst in ethyl acetate (200 mL) at room temperature for 3-4 h. The desired product was isolated after filtering the reaction mixture and concentrating the filtrate under reduced pressure. Column chromatography of the crude mass using ethyl acetate acid hexanes provided the desired compound ethyl 2-isopropoxy-3-(4-aminophenyl)propionate (1.16 g, 86% overall).

$^1$H NMR (200 MHz, CDCl$_3$) δ: 0.97 (d, J=5.8 Hz, 3H), 1.15 (d, J=5.8 Hz, 3H), 1.23 (t, J=7.0 Hz, 3H), 2.80-2.95 (m, 2H), 3.49 (quintet, 1H); 3.98 (dd, J=8.1 and 5.7 Hz, 1H), 4.16 (q, J=7.0 Hz, 2H), 6.61 (d, J=8.3 Hz, 2H), 7.03 (d, J=8.3 Hz, 2H).

IR (neat) cm$^{-1}$: 3455, 3371, 2975, 2929, 1737, 1626, 1519.

Mass m/z (CI): 252 [M+1]

EXAMPLE 1

Ethyl 3-[4-{3-(3,4-dihydro-2H-benzo[b][1,4]oxazin-4-yl)propylamino}phenyl]-2-ethoxypropanoate

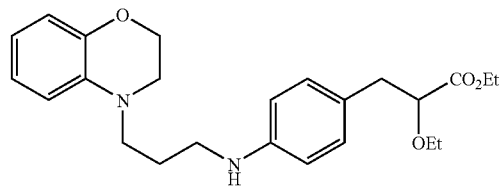

Ethyl 2-ethoxy-3-(4-aminophenyl)propanoate (2 g, 1 eq, 8.4 mmol) obtained in preparation 1,3-(3,4-dihydro-2H-benzo[b][1,4]oxazin-4-yl)propyl bromide (2.36 g, 1.1 eq, 9.3 mmol), obtained in preparation 2, and anhydrous K$_2$CO$_3$ (3.5 g, 3 eq, 25 mmol), were heated at 70° C. in DMF (40 ml) for 24 h. The reaction mixture was diluted with ethyl acetate, washed with water and brine. The residue was chromatographed using a mixture of ethyl acetate and hexane as eluent to afford the title compound as a viscous liquid (1.04 g, yield 30%).

$^1$H NMR (200 MHz, CDCl$_3$) 1.17 (t, J=7.0 Hz, 3H), 1.23 (t, J=7.0 Hz, 3H), 1.92 (q, J=7.0 Hz, 2H), 2.90 (d, J=6.8 Hz, 2H), 3.20 (t, J=7.0 Hz, 2H), 3.22-3.41 (m, 5H), 3.45-3.62 (m, 1H), 3.95 (t, J=6.4 Hz, 1H), 4.05-4.37 (m, 4H), 6.65 (d, J=8.3 Hz, 2H), 6.61-6.85 (m, 4H), 7.05 (d, J=8.3 Hz, 2H).

IR (neat) cm$^{-1}$: 3396 (br), 1740.

Mass m/z (CI): 413 (M+1).

EXAMPLE 2

3-[4-{3-(3,4-Dihydro-2H-benzo[b][1,4]oxazin-4-yl)propylamino}phenyl]-2-ethoxypropanoic acid

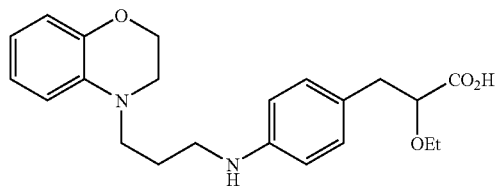

Ethyl 3-[4-{3-(3,4-dihydro-2H-benzo[b][1,4]oxazin-4-yl)propylamino}phenyl]-2-ethoxypropanoate (700 mg, 0.98 mmol) obtained in example 1, was hydrolyzed using lithium hydroxide monohydrate (123 mg, 2.9 mmol), in methanol-water at RT till all the starting material was consumed (4 to 5 h). The reaction mixture was diluted with water, acidified with dil. HCl to adjust the pH to ~4-5 and then extracted with ethyl acetate. The ethyl acetate layer was dried over Na$_2$SO$_4$ and concentrated on rotavapour. The residue was chromatographed using methanol and chloroform to yield the title compound as viscous liquid (256 mg, yield 68%).

$^1$H NMR (200 MHz, CDCl$_3$) δ: 1.19 (t, J=7.4 Hz, 3H), 1.94 (q, J=7.4 Hz, 2H), 2.90 (dd, J=14.0 and 7.0 Hz, 1H), 3.05 (dd, J=14.0 and 4.9 Hz, 1H), 3.21 (t, J=6.8 Hz, 2H), 3.25-3.40 (m, 5H), 3.40-3.62 (m, 1H), 4.00-4.17 (m, 1H), 4.18-4.22 (m, 2H), 6.59 (d, J=8.3 Hz, 2H), 6.65-6.85 (m, 4H), 7.06 (d, J=8.3 Hz, 2H).

IR (neat) cm$^{-1}$: 3500, 1725.

Mass m/z (CI): 385 (M+1)

EXAMPLE 3

3-[4-{3-(3,4-Dihydro-2H-benzo[b][1,4]oxazin-4-yl)propylamino}phenyl]-2-ethoxypropanoic acid arginine salt

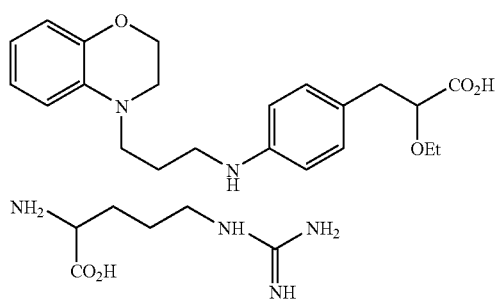

To a solution of 3-[4-{3-(3,4-dihydro-2H-benzo[b][1,4]oxazin-4-yl)propylamino}phenyl]-2-ethoxypropanoic acid (200 mg, 1 eq, 0.52 mmol) obtained in example 2, in dry methanol:dichloroethane (10:1) (5 ml), L-arginine (90.5 mg, 1 eq, 0.52 mmol) was added and allowed to stir for 3-4 h. The solvent was reduced on rotavapour followed by benzene azeotrope. The residue was dried under high vacuum pump to yield the title compound as a free flowing solid (yield 100%), mp: 92-94° C.

DSC: endotherm (weak and broad): 66.6° C.

XRD: Amorphous.

EXAMPLE 4

Ethyl 3-[4-N-heptyl-N-{2-(3-oxo-3,4-dihydro-2H-benzo[b][1,4]oxazin-4-yl)ethylamino}phenyl]-2-ethoxypropanoate

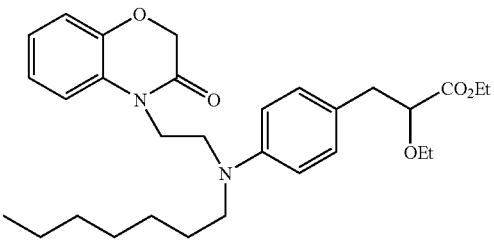

3-Oxo-3,4-dihydro-2H-benzo[b][1,4]oxazine (1.85 mg, 1.24 mmol), ethyl 2-ethoxy-3-[4-{N-heptyl-N-(2'-bromoethyl)}aminophenyl]propanoate (500 mg, 1 eq, 1.13 mmol) obtained in preparation 3, and anhydrous K$_2$CO$_3$ (468 mg, 3 eq, 3.39 mmol), were heated at 70° C. in DMF (6 ml) for 16 h. The reaction mixture was diluted with ethyl acetate, washed with water and brine. The residue was chromatographed using a mixture of ethyl acetate and hexanes as diluent to afford the title compound as thick liquid (363 mg, yield 63%).

$^1$H NMR (200 MHz, CDCl$_3$) δ: 0.88 (bt, J=6.3 Hz, 3H), 1.05-1.42 (m, 14H), 1.42-1.68 (m, 2H), 2.92 (d, J=6.8 Hz, 2H), 3.25 (t, J=7.3 Hz, 2H), 3.30-3.45 (m, 1H), 3.50-3.70 (m, 3H), 3.97 (t, J=6.6 Hz, 1H), 4.08 (t, J=7.3 Hz, 2H), 4.17 (q, J=7.0 Hz, 2H), 4.57 (s, 2H), 6.57 (d, J=8.3 Hz, 2H), 6.99 (s, 4H), 7.10 (d, J=8.0 Hz, 2H).

IR (neat) cm$^{-1}$: 1747.

Mass m/z (CI): 511 (M+1).

EXAMPLE 5

3-[4-N-Heptyl-N-{2-(3-oxo-3,4-dihydro-2H-benzo[b][1,4]oxazin-4-yl)ethylamino}phenyl]-2-ethoxypropanoic acid

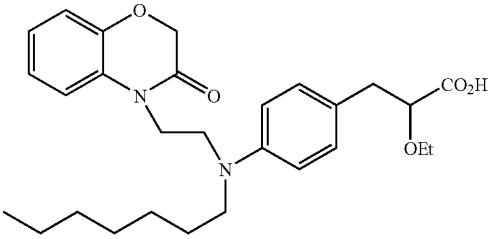

3-[4-N-Heptyl-N-{2-3-oxo-3,4-dihydro-2H-benzo[b][1,4]oxazin-4-yl)ethylamino}phenyl]-2-ethoxypropanoate (350 mg, 1 eq, 0.68 mmol) obtained in example 4, was hydrolyzed using lithium hydroxide monohydrate (86 mg, 3 eq, 2.04 mmol) in methanol water at RT till all the starting material was consumed (4 to 5 h). The reaction mixture was diluted with water, acidified with dil. HCl to pH 2-3 and then extracted with ethyl acetate. The ethyl acetate layer was dried over Na$_2$SO$_4$ and concentrated on rotavapour. The residue was chromatographed using methanol and chloroform to yield the title compound as a gummy mass (197 mg, yield 60%).

$^1$H NMR (200 MHz, CDCl$_3$) δ: 0.88 (bt, J=6.3 Hz, 3H), 1.05-1.42 (m, 11H), 1.42-1.68 (m, 2H), 2.82-3.10 (m, 2H), 3.25 (t, J=7.3 Hz, 2H), 3.40-3.70 (m, 4H), 3.98-4.15 (m, 3H), 4.56 (s, 2H), 6.67 (d, J=8.3 Hz, 2H), 6.98 (s, 4H), 7.10 (d, J=8.0 Hz, 2H).

IR (neat) cm$^{-1}$: 3500 (br), 1687.

Mass m/z (CI): 483 (M+1).

EXAMPLE 6

3-[4-N-Heptyl-N-{2-(3-oxo-3,4-dihydro-2H-benzo[b][1,4]oxazin-4-yl)ethylamino}phenyl]-2-ethoxypropanoic acid arginine salt

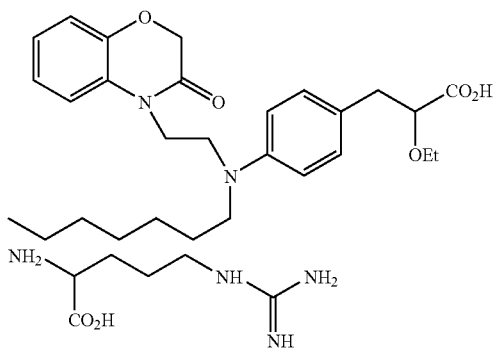

3-[4-N-Heptyl-N-{2-(3-oxo-3,4-dihydro-2H-benzo[b][1,4]oxazin-4-yl)ethylamino}phenyl]-2-ethoxypropanoic acid (150 mg, 1 eq, 0.31 mmol) obtained in example 5, and L-arginine (54 mg 1 eq, 0.31 mmol) were taken in dry method (2 ml), and stirred at RT for 2-3 h. The solvent was removed on rotavapour followed by benzene azeotrope. The residue was dried under high vacuum pump to yield the title compound as a free flowing solid (yield 100%), mp: 118-120° C.

EXAMPLE 7

Methyl 2-ethoxy-3-[4-{N-heptyl-N-(2-(3,4-dihydro-2H-benzo[b]oxazin-4-yl)-2-oxoethyl)aminomethyl}phenyl]propanoate

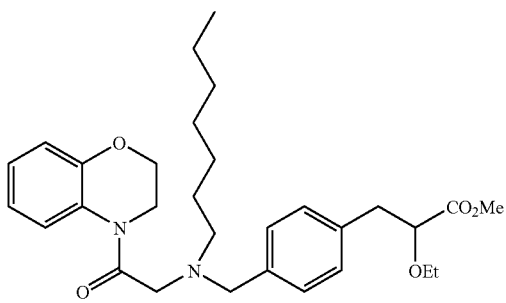

2-(3,4-Dihydro-2H-benzo[b]oxazin-4-yl)carboxymethyl chloride (208 mg, 1 eq, 0.98 mmol) obtained in preparation 4, and methyl 2-ethoxy-3-[4-(N-heptylaminomethyl)phenyl]propanoate (300 mg, 1 eq, 0.89 mmol) obtained in preparation 6, in acetonitrile (5 ml), was treated with anhydrous sodium carbonate (285 mg, 3 eq, 2.68 mmol). The reaction mixture was stirred at 80° C. for 4 h. TLC indicated absence of starting materials. The reaction mixture was diluted with ethyl acetate, washed with water and brine. The organic layer was dried over anhydrous sodium sulfate and concentrated on rotary evaporator. The residue was chromatographed using ethyl acetate and hexane to afford the title compound (250 mg, yield 55%) as viscous liquid.

$^1$H NMR (200 MHz, CDCl$_3$) δ: 0.86 (bt, J=6.3 Hz, 3H), 1.14 (t, J=6.8 Hz, 3H), 1.20-1.40 (m, 8H), 1.50-1.70 (m, 2H), 2.57 (t, J=7.0 Hz, 2H), 2.99 (d, J=6 Hz, 2H), 3.22-4.40 (m, 11H), 3.67 (s, 3H), 6.80-7.26 (aromatics, 8H).

IR (neat) cm$^{-1}$: 1752, 1683.

Mass m/z (CI): 511 [M+1].

EXAMPLE 8

2-Ethoxy-3-[4-{N-heptyl-N-(2-(3,4-dihydro-2H-benzo[b]oxazin-4-yl)-2-oxoethyl)aminomethyl}phenyl]propanoic acid

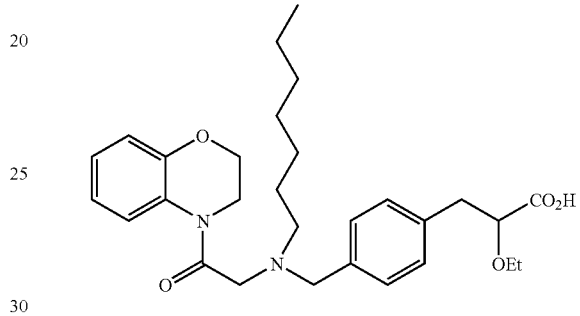

Methyl 2-ethoxy-3-[4-{N-heptyl-N-(2-(3,4-dihydro-2H-benzo[b]oxazin-4-yl)-2-oxoethyl)aminomethyl}phenyl]propanoate (240 mg, 1 eq, 0.47 mmol) obtained in example 7, was hydrolyzed using lithium hydroxide monohydrate (99 mg, 5 eq, 2.35 mmol) in methanol-water at RT (takes 4-5 h). The reaction mixture was acidified with aqueous HCl and the organic layer was extracted with ethyl acetate. The ethyl acetate layer was dried over anhydrous sodium sulfate and concentrated on rotary evaporator. The residue was chromatographed (ethyl acetate and hexane→methanol/chloroform) to afford the title compound (130 mg, yield 56%) as viscous liquid.

$^1$H NMR (200 MHz, CDCl$_3$) δ: 0.86 (bt, J=6.3 Hz, 3H), 1.10-1.40 (m, 11H), 1.40-1.60 (m, 2H), 2.79 (t, J=7.5 Hz, 2H), 2.90-4.22 (m, 13H), 6.80-7.26 (aromatics, 8H).

Mass m/z (CI): 497 [M+1].

EXAMPLE 9

2-Ethoxy-3-[4-{N-heptyl-N-(2-(3,4-dihydro-2H-benzo[b]oxazin-4-yl)-2-oxoethyl)aminomethyl}phenyl]propanoic acid arginine salt

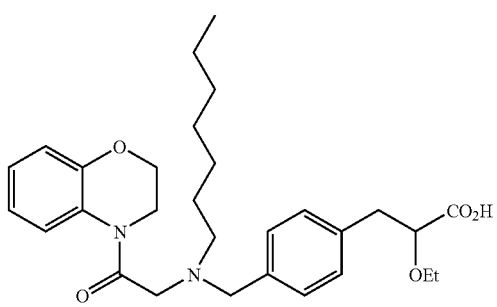

-continued

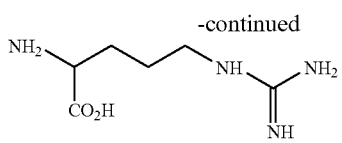

2-Ethoxy-3-[4-{N-heptyl-N-(2-(3,4-dihydro-2H-benzo[b]oxazin-4-2-oxoethyl)aminomethyl}phenyl]propanoic acid (90 mg, 0.18 mmol) obtained in example 8, and L-arginine (32 mg, 0.18 mmol) were taken in dry methanol (2 ml), and stirred at RT for 2-3 h. The solvent was removed oil rotavapour followed by benzene azeotrope. The residue was dried under high vacuum pump to yield the title compound as a free flowing solid (yield 1000%), mp: 118-120° C.

EXAMPLE 10

Methyl 3-[4-{5-(3,4-dihydro-2H-benzo[b][1,4]oxazin-4-yl)-5-oxopentylamino}phenyl]-2-ethoxypropanoate

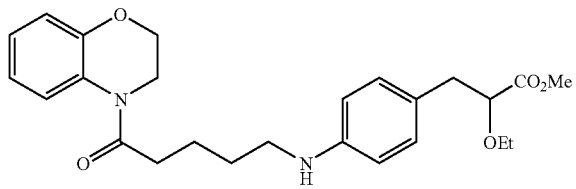

A solution of methyl 2-ethoxy-3-(4-aminophenyl)propanoate (337 mg, 1 eq, 1.51 mmol) obtained in preparation 7, 5-(3,4-dihydro-2H-benzo[b][1,4]oxazin-4-yl)-5-oxopentyl bromide (450 mg, 1 eq, 1.51 mmol) obtained in preparation 8, in DMF (6 ml) was treated with anhydrous potassium carbonate (627 mg, 3 eq, 4.54 mmol) and the reaction mixture was stirred at 70° C. for 6 h. The reaction mixture was diluted with ethyl acetate, washed with water and brine. The organic layer was dried over anhydrous sodium sulfate add concentrated on rotary evaporator. The residue was chromatographed using ethyl acetate and hexane to afford the title compound as a viscous liquid (179 mg, yield 27%).

$^1$H NMR (200 MHz, CDCl$_3$) δ: 1.16 (t, J=7.0 Hz, 3H), 1.50-1.70 (m, 2H), 1.70-1.90 (m, 2H), 2.64 (t, J=7.0 Hz, 2H), 2.89 (d, J=6.9 Hz, 2H), 3.08 (t, J=6.7 Hz, 2H), 3.22-3.42 (m, 1H), 3.42-3.62 (m, 2H), 3.68 (s, 3H), 3.88-4.00 (m, 3H), 4.26 (t, J=4.8, 2H), 6.50 (d, J=7.8 Hz, 2H, aromatics), 6.82-7.10 (aromatics, 4H), 7.04 (d, J=7.8 Hz, 2H, aromatics).

IR (KBr) cm$^{-1}$: 3408, 1739, 1683.

Mass m/z (CI): 441 [M+1].

EXAMPLE 11

3-[4-{5-(3,4-Dihydro-2H-benzo[b][1,4]oxazin-4-yl)-5-oxopentylamino}phenyl]-2-ethoxypropanoic acid

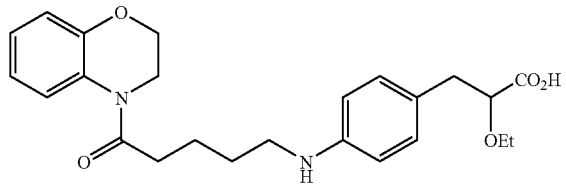

Methyl 3-[4-{5-(3,4-dihydro-2H-benzo[b][1,4]oxazin-4-yl)-5-oxopentylamino}phenyl]-2-ethoxypropanoate (211 mg, 1 eq, 0.48 mmol) obtained in example 10, was hydrolyzed using lithium hydroxide monohydrate (60 mg, 3 eq, 1.44 mmol) in methanol-water at RT (takes 4-5 h). The reaction mixture was diluted with water, acidified (pH 3-4) with aqueous HCl and then extracted with ethyl acetate. The ethyl acetate layer was dried over anhydrous sodium sulfate and concentrated on rotary evaporator. The residue was chromatographed (ethyl acetate and hexane→methanol/chloroform) to afford the title compound (139 mg, yield 68%) as viscous liquid.

$^1$H NMR (200 MHz, CDCl$_3$) δ: 1.14 (t, J=7.0 Hz, 3H), 1.50-1.90 (m, 2H), 2.62 (t, J=6.8 Hz, 2H), 2.80-3.15 (m, 4H), 3.22-3.42 (m, 1H), 3.42-3.62 (m, 1H), 3.82-4.00 (m, 3H), 4.25 (t, J=4.9, 2H), 6.40-7.30 (br shoulder, N—H, CO$_2$H), 6.55 (d, J=7.8 Hz, 2H, aromatics), 6.82-7.10 (aromatics, 4H), 7.04 (d, J=7.8 Hz, 2H, aromatics).

IR (KBr) cm$^{-1}$: 3408, 1719, 1680.

Mass m/z (CI): 427 [M+1].

EXAMPLE 12

3-[4-{5-(3,4-Dihydro-2H-benzo[b][1,4]oxazin-4-yl)-5-oxopentylamino}phenyl]-2-ethoxypropanoic acid arginine salt

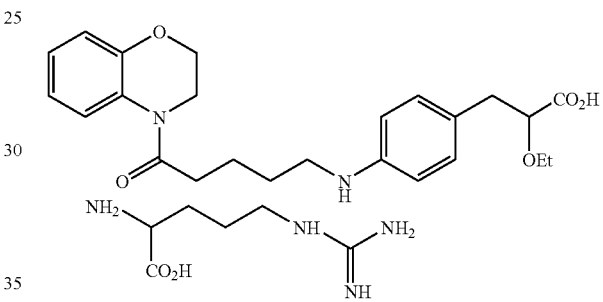

3-[4-{5-(3,4-Dihydro-2H-benzo[b][1,4]oxazin-4-yl)-5-oxopentylamino}phenyl]-2-ethoxypropanoic acid (120 mg, 1 eq, 0.28 mmol) obtained in example 11, and L-arginine (49 mg, 1 eq. 0.28 mmol) were taken in dry methanol (3 ml), and stirred at RT for 2-3 h. The solvent was removed on rotavapour followed by benzene azeotrope. The residue was dried under high vacuum pump to yield the title compound as a free filing solid (yield 100%), mp: 137-139° C.

EXAMPLE 13

Methyl 3-[3-{3-(3,4-dihydro-2H-benzo[b][1,4]oxazin-4-yl)propylamino}phenyl]-2-ethoxypropanoate

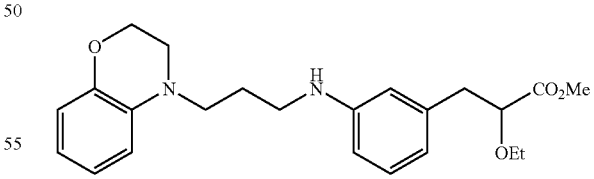

Methyl 2-ethoxy-3-(3-aminophenyl)propanoate (200 mg, 1 eq, 0.89 mmol) obtained in preparation 9, 3-(3,4-dihydro-2H-benzo[b][1,4]oxazin-4-yl)propylbromide (253 mg, 1.1 eq, 0.98 mmol) and anhydrous Na$_2$CO$_3$ (285 mg, 3 eq, 2.68 mmol) were heated at 70° C. in DMF (5 ml), for 24 h. The reaction mixture was diluted with ethyl acetate, washed with water and brine. The residue was chromatographed using ethyl acetate and hexane to afford the title compound (304 mg, yield 86%) as viscous liquid.

¹NMR (200 MHz, CDCl₃) δ: 1.17 (t, J=7 Hz, 3H), 1.98 (q, J=7 Hz, 2H), 2.92 (d, J=6.8 Hz, 2H), 3.19 (t, J=7 Hz, 2H), 3.22-3.41 (m, 5H), 3.45-3.62 (m, 1H), 3.70 (s, 3H), 4.02 (t, J=6.4 Hz, 1H), 4.22 (t, J=4.3 Hz, 2H), 6.40-6.82 (m, aromatics, 6H), 6.75 (d, J=7.8 Hz, 1H), 7.08 (t, J=7.8 Hz, 1H).

IR (neat) cm⁻¹: 3380 (br), 1743, 1680.

Mass m/z (CI): 399 (M+1).

EXAMPLE 14

3-[3-{3-(3,4-Dihydro-2H-benzo[b][1,4]oxazin-4-yl)propylamino}phenyl]-2-ethoxypropanoic acid

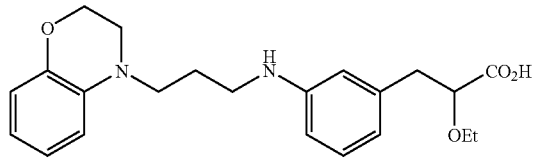

Methyl 3-[3-{3-(3,4-dihydro-2H-benzo[b][1,4]oxazin-4-yl)propylamino}phenyl]-2-ethoxypropanoate (350 mg, 1 eq, 0.87 mmol) obtained in example 13, was hydrolyzed using lithium hydroxide monohydrate (110 mg, 3 eq, 2.64 mmol), in methanol-water at RT till all the starting material is consumed (4 to 5 h). The reaction mixture was diluted with water, acidified (pH ~4-5) with dil HCl and then extracted with ethyl acetate. The ethyl acetate layer was dried over anhydrous sodium sulfate and concentrated on rotary evaporator. The residue was chromatographed using methanol and chloroform to afford the title compound (203 mg, yield 61%) as viscous oil.

¹H NMR (200 MHz, CDCl₃) δ: 1.19 (t, J=7.4 Hz, 3H), 1.94 (q, J=7.4 Hz, 2H), 2.85-3.60 (m, 10H), 4.00-4.17 (m, 1H), 4.23 (t, J=4.4 Hz, 2H), 4.95 (bs, NH, CO₂H), 6.42-7.20 (aromatics, 8H).

IR (neat) cm⁻¹: 3500 (br), 1727.

Mass m/z (CI): 385 (M+1).

EXAMPLE 15

3-[3-{3-(3,4-Dihydro-2H-benzo[b][1,4]oxazin-4-yl)propylamino}phenyl]-2-ethoxypropanoic acid arginine salt

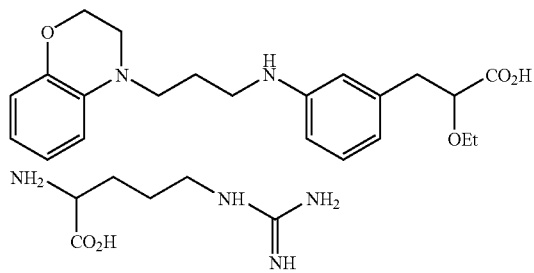

3-[3-{3-(3,4-Dihydro-2H-benzo[b][1,4]oxazin-4-yl)propylamino}phenyl]-2-ethoxypropanoic acid (90 mg, 1 eq, 0.23 mmol) obtained in example 14, and L-arginine (40.8 mg, 1 eq, 0.23 mmol) were taken in dry methanol (5 ml), and stirred at RT for 2-3 h. The solvent was removed on rotavapour followed by benzene azeotrope. The residue was dried under high vacuum pump to yield the title compound as a free flowing solid (yield 100%), mp: 178-180° C.

EXAMPLE 16

Methyl 3-[4-{3-(7-fluoro-3,4-dihydro-2H-benzo[b][1,4]oxazin-4-yl)propylamino}phenyl]-2-ethoxypropanoate

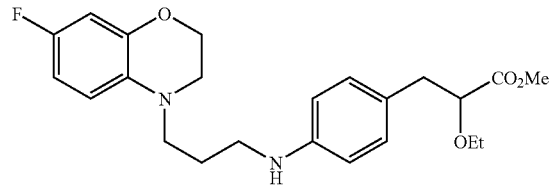

Methyl 2-ethoxy-3-(4-aminophenyl)propanoate (405.8 mg, 1 eq, 1.82 mmol) obtained in preparation 7, 3-(7-fluoro-3,4-dihydro-2H-benzo[b][1,4]oxazin-4-yl)propylbromide (500 mg, 1 eq, 1.82 mmol) obtained in preparation 10, and anhydrous Na₂CO₃ (572 mg, 3 eq, 5.4 mmol), were heated at 70° C. in acetonitrile for 24 h. The reaction mixture was diluted with ethyl acetate, washed with water and brine. The residue was chromatographed using ethyl acetate and hexane to afford the title compound (333 mg, yield 44%) a viscous liquid.

¹H NMR (200 MHz, CDCl₃) δ: 1.17 (t, J=7 Hz, 3H) 1.88 (q, J=7 Hz, 2H), 2.91 (d, J=6.8 Hz, 2H), 3.10-3.42 (m, 7H), 3.45-3.65 (m, 1H), 3.69 (s, 3H), 3.98 (t, J=6.3 Hz, 1H), 4.22 (t, J=3.9 Hz, 2H), 6.04-6.70 (m, aromatics, 5H), 7.04 (d, J=8.3 Hz, 2H).

IR (neat) cm⁻¹: 3382 (br), 1746, 1616.

Mass m/z (CI): 417 (M+1).

EXAMPLE 17

3-[4-{3-(7-Fluoro-3,4-dihydro-2H-benzo[b][1,4]oxazin-4-yl)propylamino}phenyl]-2-ethoxypropanoic acid

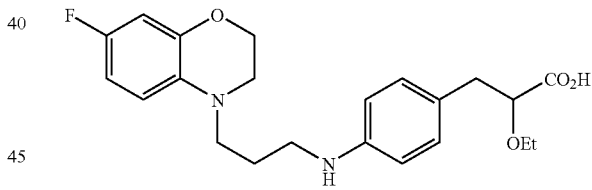

Methyl 3-[4-{3-(7-fluoro-3,4-dihydro-2H-benzo[b][1,4]oxazin-4-yl)propylamino}phenyl]-2-ethoxypropanoate (180 mg, 1 eq, 0.43 mmol) obtained in example 16, was hydrolyzed using lithium hydroxide monohydrate (55 mg, 3 eq, 1.2 mmol), in methanol-water at RT till all the starting material is consumed (4 to 5 h). The reaction mixture was diluted with water, acidified (pH ~4-5) with dil. HCl and then extracted with ethyl acetate. The ethyl acetate layer was dried over anhydrous sodium sulfate and concentrated on rotary evaporator. The residue was chromatographed using ethyl acetate and hexanes→methanol and chloroform to afford the title compound (121 mg, yield 70%) as viscous liquid.

¹H NMR (200 MHz, CDCl₃) δ: 1.19 (t, J=7.4 Hz, 3H), 1.94 (quintet, J=7.4 Hz, 2H), 2.85-3.10 (m, 2H), 3.10-3.20 (m, 6H), 3.40-3.70 (m, 2H), 3.90-4.10 (m, 1H), 4.10-4.30 (m, 2H), 6.20 (bs, CO₂H), 6.42-6.70 (m, aromatics, 5H), 7.07 (d, J=8.3 Hz, 2H).

IR (KBr) cm⁻¹: 3394, 1725, 1619.

Mass m/z (CI): 403 (M−1).

EXAMPLE 18

3-[4-{3-(7-Fluoro-3,4-dihydro-2H-benzo[b][1,4]oxazin-4-yl)propylamino}phenyl]-2-ethoxypropanoic acid arginine salt

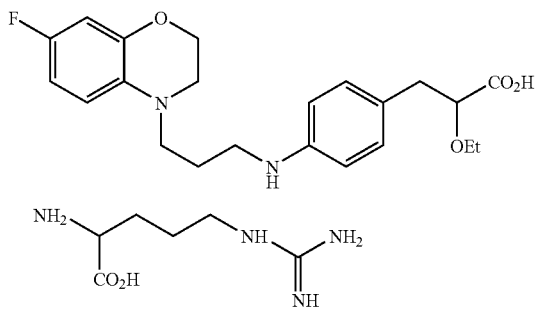

3-[4-{3-(7-Fluoro-3,4-dihydro-2H-benzo[b][1,4]oxazin-4-yl)propylamino}phenyl]-2-ethoxypropanoic acid (120 mg, 1 eq, 0.298 mmol) obtained in example 17, and L-arginine (52 mg, 1 eq, 0.298 mmol) were taken in dry methanol (2 ml), and stirred at RT for 2-3 h. The solvent was removed on rotavapour followed by benzene azeotrope. The residue was dried under high vacuum pump to yield the title compound as a free flowing solid (yield 100%), mp: 158-160° C.

EXAMPLE 19

Methyl 2-ethoxy-3-[4-{4-(3-(3,4-dihydro-2H-benzo[b][1,4]oxazin-4-yl)proploxy)benzyl}aminophenyl]propanoate

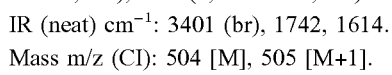

A mixture of methyl 2-ethoxy-3-{4-(4-hydroxybenzyl)aminophenyl}propanoate (600 mg, 1 eq, 1.82 mmol) obtained in preparation 12, 3-(3,4-dihydro-2H-benzo[b][1,4]oxazin-4-yl)propylbromide (467 mg, 1 eq, 1.82 mmol), and anhydrous $K_2CO_3$ (755 mg, 3 eq, 5.46 mmol) in DMF (10 ml) was stirred at RT for 16 h. The reaction was diluted with ethyl acetate, washed with water and brine. The organic layer was dried over anhydrous sodium sulfate and was concentrated on rotary evaporator. The residue was chromatographed using EtOAc/hexanes to afford the title compound (520 mg, 56% yield) as thick liquid.

$^1$H NMR (CDCl$_3$, 200 MHz) δ: 1.19 (t, J=7.0 Hz, 3H), 2.00-2.20 (m, 2H), 2.90 (d, J=6.3 Hz, 2H), 3.30-3.60 (m, 6H), 3.70 (bs, 3H), 3.80-4.10 (m, 3H+NH), 4.10-4.25 (m, 4H), 6.57 (d, J=8.3 Hz, 2H), 6.60-6.90 (m, 6H), 7.04 (d, J=8.3 Hz, 2H), 7.28 (d, J=8.3 Hz, 2H).

IR (neat) cm$^{-1}$: 3401 (br), 1742, 1614.

Mass m/z (CI): 504 [M], 505 [M+1].

EXAMPLE 20

Methyl 2-ethoxy-3-[3-{4-(3-(3,4-dihydro-2H-benzo[b][1,4]oxazin-4-yl)propyloxy)benzyl}aminophenyl]propanoate

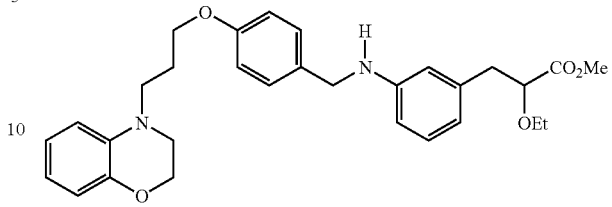

The title compound was prepared (340 mg, yield 90%) as viscous liquid from a mixture of methyl 2-ethoxy-3-{3-(4-hydroxybenzyl)aminophenyl}propanoate (250 mg, 1 eq, 0.75 mmol) obtained in preparation 13, and 3-(3,4-dihydro-2H-benzo[b][1,4]oxazin-4-yl)propylbromide (192 mg, 1 eq, 0.75 mmol) obtained in preparation 2, by following the similar procedure as described for example 19.

$^1$H NMR (200 MHz, CDCl$_3$) δ: 1.19 (t, J=7.0 Hz, 3H), 1.95-2.18 (m, 2H), 2.90 (d, J=6.3 Hz, 2H), 3.22-3.60 (m, 6H), 3.70 (bs, 3H), 3.90-4.10 (m, 3H), 4.10-4.25 (m, 4H), 6.42-6.90 (aromatics, 8H), 7.05 (t, J=7.8, 1H), 7.20-7.30 (m, aromatics, 3H).

IR (neat) cm$^{-1}$: 3407 (br), 1742, 1607.

Mass m/z (CI): 504 [M], 505 [M+1].

EXAMPLE 21

2-Ethoxy-3-[4-{4-(3-(3,4-dihydro-2H-benzo[b][1,4]oxazin-4-yl)propyloxy)benzyl}aminophenyl]propanoic acid

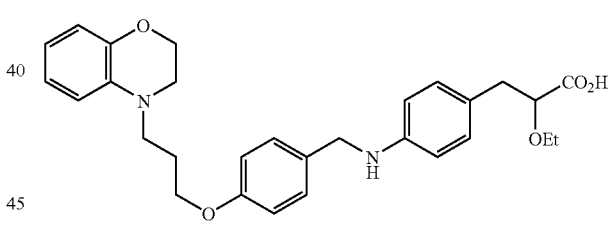

Methyl 2-ethoxy-3-[4-{4-(3-3,4-dihydro-2H-benzo[b][1,4]oxazin-4-yl)propyloxy)benzyl}aminophenyl]propanoate (510 mg, 1 eq, 1.01 mmol) obtained in example 19, was hydrolyzed using lithium hydroxide monohydrate (127 mg, 3 eq, 3.03 mmol) in methanol-water at RT till all the starting material was consumed (4 to 5 h). The reaction mixture was diluted with water, acidified (pH ~3-4) with dil HCl and then extracted with EtOAc. The residue was chromatographed using ethyl acetate/hexanes to yield the title compound as sticky liquid (250 mg, 51%).

$^1$H NMR (200 MHz, CDCl$_3$) δ: 1.18 (t, J=6.9 Hz, 3H), 1.26 (t, J=7.3 Hz, 1H, N—H), 1.98-2.18 (m, 2H), 2.90 (dd, J=14.1, 7.4 Hz, 1H), 3.04 (dd, J=14.1, 4.4 Hz, 1H), 3.35 (t, J=4.2 Hz, 2H), 3.40-3.64 (m, 4H), 3.95-4.10 (m, 3H); 4.10-4.25 (m, 4H), 6.57 (d, J=8.3 Hz, 2H), 6.60-6.82 (m, 4H), 6.88 (d, J=8.3 Hz, 2H), 7.05 (d, J=8.3 Hz, 2H), 7.28 (d, J=8.3 Hz, 2H).

IR (neat) cm$^{-1}$: 3407, 1723, 1610.

Mass m/z (CI): 490 [M], 491 [M+1].

EXAMPLE 22

2-Ethoxy-3-[3-{4-(3-(3,4-dihydro-2H-benzo[b][1,4]oxazin-4-yl)propyloxy)benzyl}aminophenyl]propanoic acid

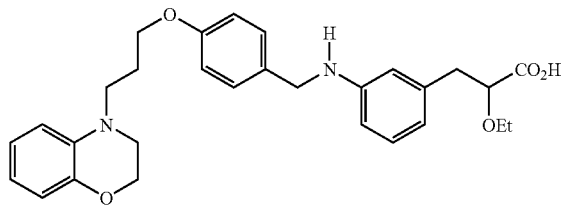

The title compound was prepared (220 mg, yield 53%) as viscous liquid from methyl 2-ethoxy-3-[3-{4-(3-(3,4-dihydro-2H -benzo[b][1,4]oxazin-4-yl)propyloxy)benzyl}aminophenyl]propanoate (420 mg, 0.83 mmol) obtained in example 20, by following the similar procedure as described for example 21.

$^1$H NMR (200 MHz, CDCl$_3$) δ: 1.15 (t, J=6.9 Hz, 3H), 1.26 (t, J=7.3 Hz, 1H, N—H), 1.98-2.18 (m, 2H), 2.90 (dd, J=14.1, 7.8 Hz, 1H), 3.05 (dd, J=13.7, 3.9 Hz, 1H), 3.30-3.60 (m, 6H), 3.70 (bs, 3H), 4.00-4.10 (m, 3H), 4.10-4.25 (m, 4H), 6.42-6.90 (m, aromatics, 8H), 7.09 (t, J=7.8, 1H), 7.20-7.30 (m, aromatics, 3H).

IR(neat) cm$^{-1}$: 3407 (br), 1725, 1606.

Mass m/z (CI): 491 [M+1].

EXAMPLE 23

2-Ethoxy-3-[4-{4-(3-(3,4-dihydro-2H-benzo[b][1,4]oxazin-4-yl)propyloxy)benzyl}aminophehyl]propanoic acid arginine salt

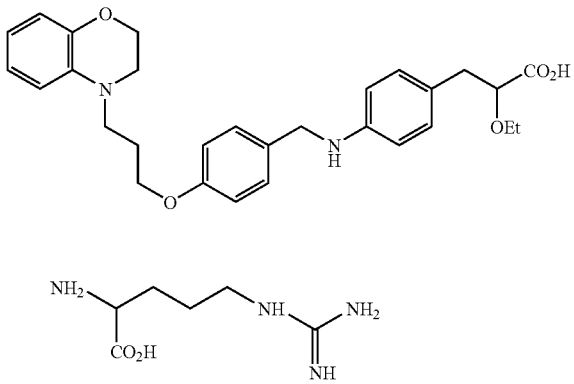

2-Ethoxy-3-[4-{4-(3-(3,4-dihydro-2H-benzo[b][1,4]oxazin-4-yl)propyloxy)benzyl}aminophenyl]propanoic acid (250 mg, 1 eq, 0.5 mmol) obtained in example 21, and L-arginine (88.7 mg, 1 eq, 0.51 mmol) was stirred in dry methanol (3 ml) for 3-4 h at RT. The solvent was condensed on rotavapour, followed by benzene azeotrope. The residue was dried under high vacuum pump to yield the title compound as a solid (yield 100%), mp: 141-142° C.

EXAMPLE 24

2-Ethoxy-3-[3-{4-(3-(3,4-dihydro-2H-benzo[b][1,4]oxazin-4-yl)propyloxy)benzyl}aminophenyl]propanoic acid arginine salt

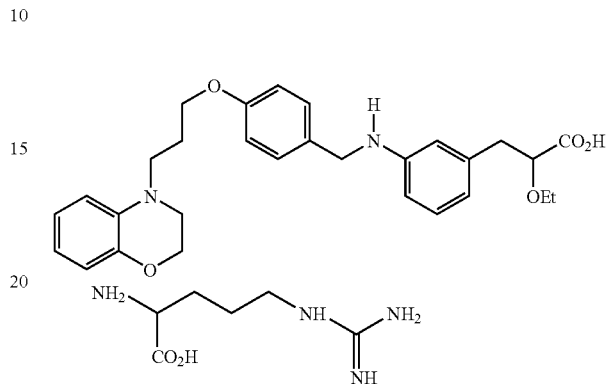

2-Ethoxy-3-[3-{4-(3-(3,4-dihydro-2H-benzo[b][1,4]oxazin-4-yl)propyloxy)benzyl}aminophenyl]propanoic acid (140 mg, 1 eq, 0.28 mmol) obtained in example 22, and L-arginine (50 mg, 1 eq, 0.28 mmol) was stirred in dry methanol (3 ml) for 3-4 h at RT. The solvent was condensed on rotavapour and followed by benzene azeotrope. The residue was dried under high vacuum pump to yield the title compound as a solid (yield 100%), mp: 152-154° C.

EXAMPLE 25

Ethyl 2-ethoxy-3-[4-{3-(3,4-dihydro-2H-benzo[b][1,4]thiazin-4-yl)propylamino}phenyl]propanoate

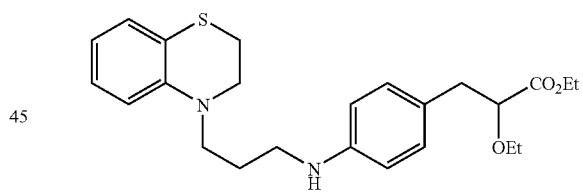

A mixture of 3-(3,4-dihydro-2H-benzo[b][1,4]thiazin-4-yl)propylbromide (1.76 g, 1.1 eq, 6.5 mmol), obtained in preparation 14, ethyl 2-ethoxy-3-(4-aminophenyl)propanoate (1.4 g, 1.0 eq, 5.9 mmol), obtained in preparation 1, and anhydrous K$_2$CO$_3$ (2.45 g, 3.0 eq, 17.7 mmol) in dry DMF (30 ml) was stirred at RT for 2 days. The reaction was diluted with ethyl acetate (100 ml) and washed with water and brine. The organic layer was dried. (Na$_2$SO$_4$), condensed, and the residue was chromatographed using ethyl acetate and hexane to obtain the title compound as viscous liquid (500 mg, 20% yield).

$^1$H NMR (200 MHz, CDCl$_3$) δ: 1.17 (t, J=6.8 Hz, 3H), 1.23 (t, J=6.6 Hz, 3H), 1.27 (bs, 1H, N—H), 1.94 (quintet, 6.8 Hz, 2H) 2.90 (d, J=6.9 Hz, 2H), 3.03 (t, J=4.8 Hz, 2H), 3.20 (t, J=6.9 Hz, 2H), 3.20-3.45 (m, 3H), 3.45-3.64 (m, 3H), 3.95 (t, J=6.4 Hz, 1H), 4.16 (q, J=6.9 Hz, 2H), 6.50-6.72 (aromatics, 4H), 6.90-7.10 (aromatics, 4H).

IR (neat) cm$^{-1}$: 3398, 2926, 1742, 1616.

Mass m/z (CI): 428 [M], 429 [M+1].

EXAMPLE 26

2-Ethoxy-3-[4-{3-(3,4-dihydro-2H-benzo[b][1,4]thiazin-4-yl)propylamino}phenyl]propanoic acid

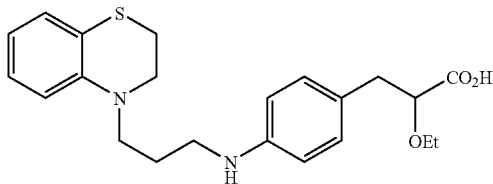

Ethyl 2-ethoxy-3-[4-{3-(3,4-dihydro-2H-benzo[b][1,4]thiazin-4-yl)propylamino}phenyl]propanoate (250 mg, 1.0 eq, 0.58 mmol), obtained in example 25, was hydrolyzed by treating with LiOH.H$_2$O (74 mg, 3 eq, 1.75 mmol) in MeOH-THF-water solvent mixture at RT for 3-4 h. The reaction mixture was condensed, diluted with water and acidified (pH at 4) with aq. HCl. Finally the crude acid was extracted with ethyl acetate. The ethyl acetate layer was dried (Na$_2$SO$_4$), condensed, and chromatographed using MeOH and CHCl$_3$ as eluent to obtain the title compound as thick liquid (152 mg, 68% yield).

$^1$H NMR (200 MHz, CDCl$_3$) δ: 1.17 (t, J=6.9 Hz, 3H), 1.26 (bs, 1H, N—H); 1.93 (quintet, 6.9 Hz, 2H), 2.85-3.10 (m, 4H), 3.02 (t, J=5.1 Hz, 2H), 3.19 (t, J=6.9 Hz, 2H); 3.20-3.65 (m, 4H), 4.02 (dd, J=6.9, 4.4 Hz, 1H), 4.70 (bs, 1H, CO$_2$H), 6.50-6.72 (aromatics, 4H), 6.90-7.10 (aromatics, 4H).

IR (neat) cm$^{-1}$: 3411, 2929, 1726, 1616.

Mass m/z (CI): 400 [M], 401 [M+1].

EXAMPLE 27

2-Ethoxy-3-[4-{3-3,4-dihydro-2H-benzo[b][1,4]thiazin-4-yl)propylamino}phenyl]propanoic acid arginine salt

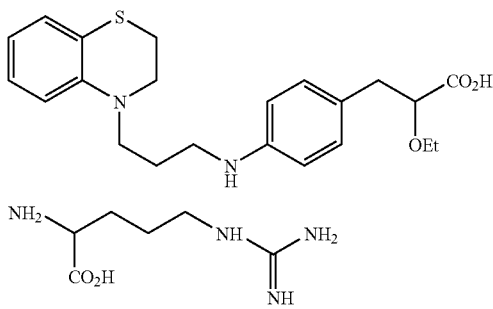

A mixture of 2-ethoxy-3-[4-{3-3,4-dihydro-2H-benzo[b][1,4]thiazin-4-yl)propylamino}phenyl]propanoic acid (110 mg, 1 eq, 0.27 mmol), obtained in example 26, and L-arginine (47.9 mg, 1 eq, 0.27 mmol) was taken in dry MeOH (2.0 ml) was stirred at RT for 2 h to get a clear solution. The solvent was condensed, the residue was azeotroped with dry benzene and dried over vacuum pump to obtain the title compound as a solid mass (100% yield), mp: 142-144° C.

EXAMPLE 28

Ethyl 2-ethoxy-3-[4-{2-(3,4-dihydro-2H-benzo[b][1,4]oxazin-4-yl)ethylamino}phenyl]propanoate

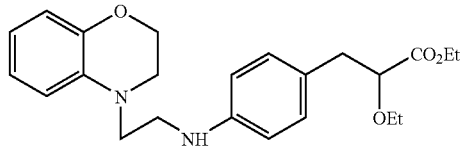

A mixture of 2-(3,4-dihydro-2H-benzo[b][1,4]oxazin-4-yl)ethylbromide (940 mg, 1 eq, 3.8 mmol), obtained in preparation 15, ethyl 2-ethoxy-3-(4-aminophenyl)propanoate (1.0 g, 1.1 eq, 4.2 mmol), obtained in preparation 1, anhydrous K$_2$CO$_3$ (1.6 g, 3 eq, 10.8 mmol) and tetrabutylammonium bromide (265 mg, 0.2 eq, 0.8 mmol) in dry toluene (20 ml) was heated at 90° C. for 24 h. The reaction mixture was diluted with ethyl acetate and the organic layer was washed with water, brine, then dried (Na$_2$SO$_4$), and condensed. The residue was chromatographed with ethyl acetate and hexanes as eluents to obtain the desired product as thick liquid (960 mg, 60%).

$^1$H NMR (200 Mz, CDCl$_3$) δ: 1.17 (t, J=6.9 Hz, 3H), 1.23 (t, J=6.6 Hz, 3H), 1.27 (bs, 1H, N—H), 2.90 (d, J=6.4 Hz, 2H), 3.20-3.65 (m, 8H), 3.95 (t, J=6.4 Hz, 1H), 4.05-4.25 (m, 4H), 6.56 (d, J=8.3 Hz, 2H), 6.60-6.85 (aromatics, 4H), 7.06 (d, J=8.3 Hz, 2H).

IR (neat) cm$^{-1}$: 3395, 2977, 1740, 1616.

Mass m/z (CI): 398 [M], 399 [M+1].

EXAMPLE 29

2-Ethoxy-3-[4-{2-(3,4-dihydro-2H-benzo[b][1,4]oxazin-4-yl)ethylamino}phenyl]propanoic acid

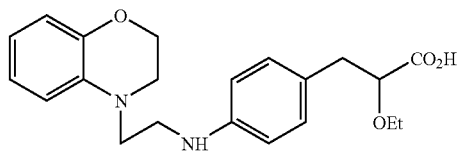

Ethyl 2-ethoxy-3-[4-{2-(3,4-dihydro-2H-benzo[b][1,4]oxazin-4-yl)ethylamino}phenyl]propanoate (960 mg, 1.0 eq, 2.41 mmol), obtained in example 28, was hydrolyzed by treating with LiOH.H$_2$O (350 mg, 3 eq, 7.2 mmol) in MeOH-THF-water solvent mixture at RT for 3-4 h. The reaction mixture was condensed, diluted with water and acidified (pH at 4-5) with aq. HCl. Finally the crude acid was extracted with ethyl acetate. The ethyl acetate layer was dried (Na$_2$SO$_4$), condensed, and chromatographed using MeOH and CHCl$_3$ as eluents to obtain the desired compound as thick liquid (370 mg, 42%).

$^1$H NMR (200 MHz, CDCl$_3$) δ: 1.17 (t, J=6.8 Hz, 3H), 1.21 (bs, 1H, N—H), 2.90 (dd, J=14, 8 Hz, 1H), 3.03 (dd, J=14, 4.3 Hz, 1H), 3.20-3.65 (m, 8H), 4.02 (dd, J=6.49, 4.4 Hz, 1H), 4.21 (t, J=4.4 Hz, 2H), 5.00 (bs, CO$_2$H), 6.58 (d, J=8.3 Hz, 2H), 6.60-6.85 (aromatics, 4H), 7.06 (d, J=8.3 Hz, 2H).

IR (neat) cm$^{-1}$: 3383 (br), 2927, 1727, 1607.

Mass m/z (CI): 371 [M+1].

EXAMPLE 30

2-Ethoxy-3-[4-{2-(3,4-dihydro-2H-benzo[b][1,4]oxazin-4-yl)ethylamino}phenyl]propanoic acid arginine salt

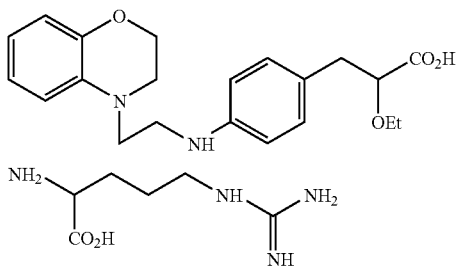

The title compound was prepared as a free flowing solid (mp: 142-144° C.) from 2-ethoxy-3-[4-{2-(3,4-dihydro-2H-benzo[b][1,4]oxazin-4-yl)ethylamino}phenyl]propanoic acid, obtained in example 29 and L-arginine, by following the similar procedure as described for example 27.

EXAMPLE 31

Methyl 2-ethoxy-3-[4-[4-{2-(3,4-dihydro-2H-benzo[b][1,4]oxazin-4-yl)ethoxy}phenylaminomethyl]phenyl]propanoate

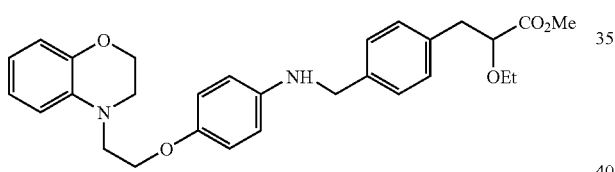

A mite of 4-{2-(3,4-dihydro-2H-benzo[b][1,4]oxazin-4-yl)ethoxy}aniline (305 mg, 1 eq, 1.13 mmol) obtained in preparation 16, methyl 2-ethoxy-3-(4-formylphenyl)propanoate (267 mg, 1 eq, 1.13 mmol), obtained in preparation 5, activated molecular sieves (4 A), and p-TsOH (21 mg, 0.1 eq, 0.11 mmol) in dry DCM (4 ml) were stirred at RT for 16 h. The reaction mixture was diluted with ethylacetate (100 ml), washed with aq. sodium bicarbonate, dried ($Na_2SO_4$), and condensed. The crude mass was dissolved in dry methanol (6 ml) and conc HCl (125 μL) was added at 0° C., followed by $NaB(CN)H_3$ (118 mg, 1.5 eq, 1.87 mmol) in portions. The reaction mixture was stirred at 0° C. for 3 h, after that it was diluted with ethyl acetate (100 ml). The organic layer was washed with aq. sodium bicarbonate, dried ($Na_2SO_4$), and condensed. The residue was chromatographed using ethyl acetate and hexanes to obtain the title compound as thick oil (525 mg, 85%).

$^1$H (200 MHz, $CDCl_3$) δ:1.16 (t, J=6.9 Hz, 3H), 1.25 (bs, —NH—), 3.00 (d, J=6.8, 2H), 3.22-3.42 (m, 1H), 3.49 (t, J=4.4 Hz, 2H), 3.55-3.75 (m, 3H), 3.71 (s, 3H), 3.99-4.12 (m, 3H), 4.15-4.24 (m, 4H), 6.50-6.90 (aromatics, 8H), 7.19 (d, J=7.8, 2H), 7.28 (d, J=8.0, 2H).

IR (neat) cm$^{-1}$: 3405 (br), 2927, 146, 1606.

Mass m/z (CI): 490 [M], 491 [M+1].

EXAMPLE 32

2-Ethoxy-3-[4-[4-{2-(3,4-dihydro-2H-benzo[b][1,4]oxazin-4-yl)ethoxy}phenylaminomethyl]phenyl]propanoic acid

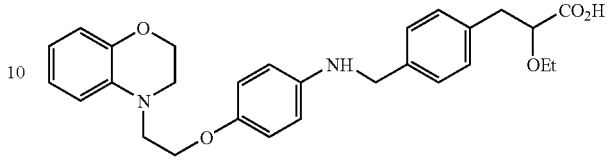

Methyl 2-ethloxy-3-[4-[4-{2-(3,4-dihydro-2H-benzo[b][1,4]oxazin-4-yl)ethoxy}phenylaminomethyl]phenyl]propanoate (520 mg, 1.0 eq, 1.06 mmol), obtained in example 31, was hydrolyzed by train with $LiOH.H_2O$ (134 mg, 3 eq, 3.18 mmol) in MeOH-THF-water solvent mixture at RT for 3-4 h. The reaction mixture was condensed, diluted with water and acidified (pH at 4) with aq. HCl. Finally the crude acid was extracted out by ethyl acetate. The ethyl acetate layer was dried ($Na_2SO_4$), condensed, and chromatographed using MeOH and $CHCl_3$ as eluents to obtain the desired compound as thick liquid (150 mg, 30%).

$^1$H NMR (200 MHz, $CDCl_3$) δ: 1.18 (t, J=6.9 Hz, 3H), 1.29 (bs, —NH—), 2.90-3.20 (m, 2H), 3.22-3.75 (m, 6H), 4.00-4.18 (m, 3H), 4.20-4.25 (m, 4H), 6.00 (bs, $CO_2H$), 6.60-6.90 (aromatics, 8H), 7.24 (d, J=8.3, 2H), 7.29 (d, J=8.3, 2H).

IR (neat) cm$^{-1}$: 3390 (br), 2927, 1725, 1605.

Mass m/z (CI): 476 [M], 477 [M+1].

EXAMPLE 33

2-Ethoxy-3-[4-[4-{2-(3,4-dihydro-2H-benzo[b][1,4]oxazin-4-yl)ethoxy}phenylaminomethyl]phenyl]propanoic acid arginine salt

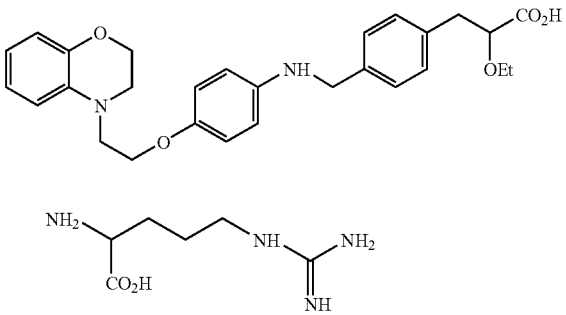

A mixture of 2-ethoxy-3-[4-[4-{2-(3,4-dihydro-2H-benzo[b][1,4]oxazin-4-yl)ethoxy}phenylaminomethyl]phenyl]propanoic acid (110 mg, 1 eq, 0.23 mmol), obtained in example 32, and L-arginine (40 mg, 1 eq, 0.23 mmol) taken in dry MeOH (2 ml) was stirred at RT for 2 h to get a clear solution. The solvent was condensed, the residue was azeotroped with dry benzene and dried over vacuum pump to obtain a solid mass (100% yield), mp: 154-156° C.

EXAMPLE 34

[2S,N(1R)]-N-(2-hydroxy-1-phenylethyl)-2-ethoxy-3-[4-{3-(3,4-dihydro-2H-benzo[b][1,4]oxazin-4-yl)propylamino}phenyl]propanamide

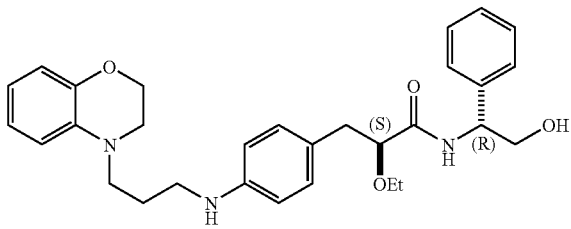

To a solution of racemic 2-ethoxy-3-[4-{3-(3,4-dihydro-2H-benzo[b][1,4]oxazin-4-yl)propylamino}phenyl]propanoic acid (2.0 g, 1.0 eq, 5.20 mmol) obtained in example 2, in DCM (26 ml) and triethylamine (3.61 ml, 5 eq, 26 mmol), isobutylchloroformate (1.35 ml, 2 eq, 10.4 mmol) was added dropwise at 0° C. The reaction mixture was stirred at RT for 30 min followed by addition of (R)-phenylglycinol (1.42 g, 2 eq, 10.4 mmol). The reaction mixture was further stirred at RT for 16 h, which was then diluted with DCM, washed with water and brine, dried (Na$_2$SO$_4$), and codensed. The residue was chromatographed using ethyl acetate and hexane to obtain the title compound as faster moving (S,R)-diastereomer (620 mg, 23.7% yield), follolwed by relatively slower moving (R,R)-diastereomer, (630 mg, 24% yield), both as viscous liquid. Characterization of (R,R)-diastereomer is described in example 35.

$^1$H NMR (200 MHz, CDCl$_3$) δ: 1.14 (t, J=6.8 H, 3H), 1.24 (s, 1H), 1.91 (quintet, J=6.8 Hz, 2H), 2.90 (dd, J=12 and 5.8 Hz, 1H), 3.06 (dd, J=12 and 3.9 Hz, 1H), 3.19 (t, J=6.8 Hz, 2H), 3.25-3.60 (m, 6H), 3.60-3.70 (m, 2H), 3.97 (dd, J=5.8 and 3.9 Hz, 1H), 4.22 (t, J=4.4 Hz, 2H), 4.88-5.00 (m, 1H), 6.50-7.40 (aromatic and amide-NH, 14H).

IR (neat) cm$^{-1}$: 3393 (br), 2927, 1660.

Mass m/z (CI): 503 [M], 504 [M+1].

EXAMPLE 35

[2R,N(1R)]-N-(2-hydroxy-1phenylethyl)-2-ethoxy-3-[4-{3-(3,4-dihydro-2H-benzo[b][1,4]oxazin-4-yl)propylamino}phenyl]propanamide

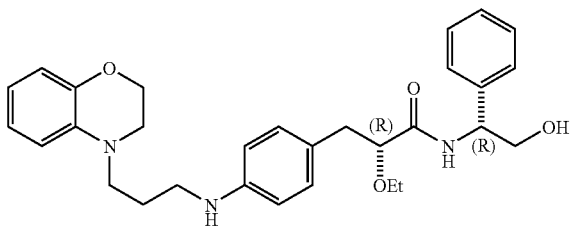

The title compound is obtained by following the similar procedure described in example 34.

$^1$H NMR (200 MHz, CDCl$_3$) δ: 1.16 (t, J=6.8 Hz, 3H), 1.24 (s, 1H), 1.91 (quintet, J=6.8 Hz, 2H), 2.80 (dd, J=14, 7.5 Hz, 1H), 3.06 (dd, J=14, 3.9 Hz, 1H), 3.17 (t, J=6.8 Hz, 2H), 3.25-3.60 (m, 6H), 3.78-3.90 (m, 2H), 3.89 (dd, J=7.5, 3.9 Hz, 1H), 4.22 (t, J=4.4 Hz, 2H), 4.88-5.00 (m, 1H), 6.45-7.35 (aromatics and amide-NH, 14H).

IR (neat) cm$^{-1}$: 3399 (br), 2927, 1660.

Mass m/z (CI): 503 [M], 504 [M+1].

EXAMPLE 36

[2S,N(1R)]-N-(2-hydroxy-1-phenylethyl)-2-ethoxy-3-[4-{3-(3,4-dihydro-2H-benzo[b][1,4]oxazin-4-yl)propylamino}phenyl]propanamide hydrochloride salt

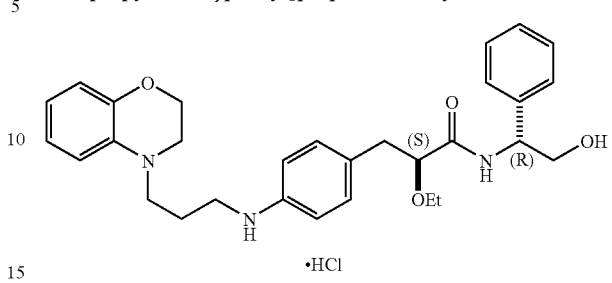

To a dry methanolic HCl solution (2 ml) [2S,N(1R)]-N-(2-hydroxy-1-phenylethyl)-2-ethoxy-3-[4-{3-(3,4-dihydro-2H-benzo[b][1,4]oxazin-4-yl)propylamino}phenyl]propanamide (95 mg, 0.19 mmol) obtained in example 34, was added and the mixture was stirred at RT for 5 min. Then the reaction mixture was condensed and azeotroped using dry benzene on rotary evaporator. The residue was dried on high-vacuum to obtain the title compound as a brown solid mass (100% yield, mp: 74-75° C.).

EXAMPLE 37

[2R,N(1R)]-N-(2-hydroxy-1-phenylethyl)-2-ethoxy-3-[4-{3-(3,4-dihydro-2H-benzo[b][1,4]oxazin-4-yl)propylamino}phenyl]propanamide hydrochloride salt

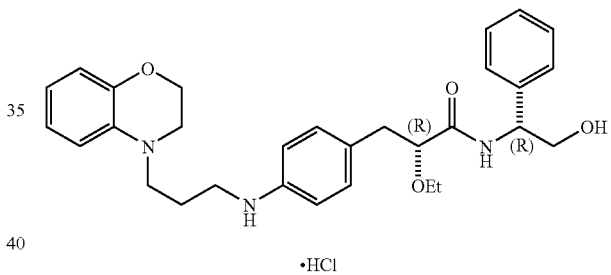

To a dry methanolic HCl solution (2 ml) [2R,N(1R)]-N-(2-hydroxy-1-phenylethyl)-2-ethoxy-3-[4-{3-(3,4-dihydro-2H-benzo[b][1,4]oxazin-4-yl)propylamino}phenyl]propanamide (95 mg, 0.19 mmol) obtained in example 35, was added and the mixture was stirred at RT for 5 min. Then the reaction mixture was condensed and azeotroped using dry benzene on rotary evaporator. The residue was dried on high-vacuum to obtain the title compound as a brown solid mass (100% yield, mp: 69-70° C.).

EXAMPLE 38

2-Ethoxy-3-[4-{3-(3,4-dihydro-2H-benzo[b][1,4]oxazin-4-yl)propylamino}phenyl]propanoic acid magnesium salt

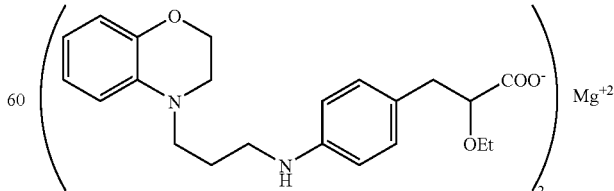

A mixture of methanolic solution (2 ml) of 2-ethoxy-3-[4-{3-(3,4-dihydro-2H-benzo[b][1,4]oxazin-4-yl)propylamino}phenyl]propanoic acid (75 mg, 1 eq, 0.19 mmol) obtained in example 2 and magnesium hydroxide (5.6 mg, 0.5 eq, 0.095 mmol) was heated at 50° C. for 5 h. The resulting solution was condensed, azeotroped with benzene and then finally dried on high vacuum pump to obtain the title compound as freed flowing solid (100% yield, mp: 132-134° C.).

EXAMPLE 39

[2S,N(1R)]-N-(2-hydroxy-1-phenylethyl)-2-ethoxy-3-[4-{3-(7-fluoro-3,4-dihydro-2H-benzo[b][1,4]oxazin-4-yl)propylamino}phenyl]propanamide

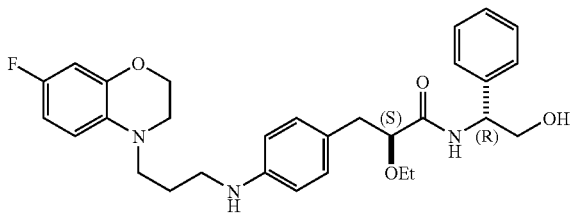

To a solution of racemic 2-ethoxy-3-[4-{3-(7-fluoro-3,4-dihydro-2H-benzo[b][1,4]oxazin-4-yl)propylamino}phenyl]propanoic acid (1.8 g, 1.0 eq, 4.48 mmol) obtained in example 17, in DCM (25 ml) and triethylamine (2.49 ml, 4 eq, 17.92 mmol); isobutylchloroformate (875 µL, 1.5 eq, 6.72 mmol) was added dropwise at 0° C. The reaction mixture was stirred at RT for 30 min followed by addition of (R)-phenylglycinol (1.23 g, 2 eq, 8.96 mmol). The reaction mixture was further stirred at RT for 16 h, which was then diluted with DCM, washed with water and brine, dried ($Na_2SO_4$), and condensed. The residue was chromatographed using ethyl acetate and hexane to obtain the title compound as faster moving (S,R)-diastereomer (370 mg, 32% yield), followed by relatively slower moving (R,R)-diastereomer, (370 mg, 32% yield), both as viscous liquid. Characterization of (R,R)-diastereomer is described in example 40 (next example).

$[\alpha]_D$: −7.0° (c, 1.0 $CHCl_3$).

$^1$H NMR (200 MHz, $CDCl_3$) δ: 1.16 (t, J=6.8 Hz, 3H), 1.92 (quintet, J=6.8 Hz, 2H), 2.92 (dd, J=14, 5.6 Hz, 1H), 3.08 (dd, J=14, 3.5 Hz, 1H), 3.22 (t, J=6.4 Hz, 2H), 3.20-3.40 (m, 4H), 3.40-3.80 (m, 4H), 3.99 (t, J=5.2 Hz, 1H), 4.23 (t, J=4.4 Hz, 2H), 4.88-5.02 (m, 1H), 6.40-6.60 and 6.90-7.40 (aromatics and amide-NH, 13H).

IR (neat) $cm^{-1}$: 3405 (br), 2933, 1660, 1615, 1514.

Mass m/z (CI): 521 [M], 522 [M+1].

EXAMPLE 40

[2R,N(1R)]-N-(2-hydroxy-1-phenylethyl)-2-ethoxy-3-[4-{3-(7-fluoro-3,4-dihydro-H-benzo[b][1,4]oxazin-4-yl)propylamino}phenyl]propanamide

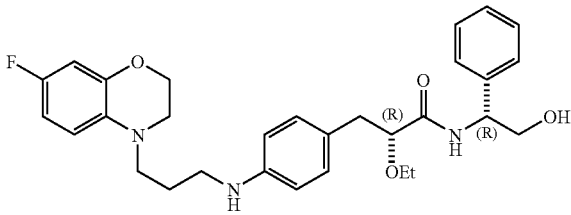

The title compound is obtained during syntheis of example 39 as another diastereomer (R,R).

$[\alpha]_D$: 17.4° (c, 1.0 $CHCl_3$).

$^1$H NMR (200 MHz, $CDCl_3$) δ: 1.18 (t, J=6.8 Hz, 3H), 1.91 (quintet, J=6.8 Hz, 2H), 2.51 (bs, NH, OH); 2.82 (dd, J=14.2 and 7.3 Hz, 1H), 3.04 (dd, J=14.2 and 3.4 Hz, 1H), 3.20 (t, J=6.4 Hz, 2H); 3.25-3.40 (m, 4H), 3.42-3.70 (m, 2H), 3.80-3.90 (m, 2H), 3.98 (dd, J=7.3 and 4.0 Hz, 1H), 4.24 (t, J=4.8 H, 2H), 4.88-5.2 (m, 1H), 6.4-6.60 and 7.00-7.40 (aromatic and amide-NH, 13H).

IR (neat) $cm^{-1}$: 3398 (br), 2929, 1660, 1616, 1513.

Mass m/z (CI): 521 [M], 522 [M+1].

EXAMPLE 41

[2S,N(1R)]-N-(2-hydroxy-1-phenylethyl-2-ethoxy-3-[4-{3-(3,4-dihydro-2H-benzo[b][1,4]oxazin-4-yl)propylamino}phenyl]propanamide hydrochloride salt

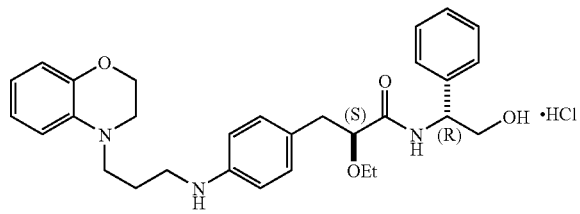

To a dry methanolic HCl solution (2 ml) [2S,N(1R)]-N-(2-hydroxy-1-phenylethyl)-2-ethoxy-3-[4-{3-(3,4-dihydro-2H-benzo[b][1,4]oxazin-4-yl)propylamino}phenyl]propanamide (95 mg, 0.19 mmol) obtained in example 34, was added and the mixture was stirred at RT for 5 min. Then the reaction mixture was condensed and azeotroped using dry benzene on rotary evaporator. The residue was dried on high-vacuum to obtain the title compound as a brown solid mass (100% yield, mp: 74-75° C.).

EXAMPLE 42

[2R,N(1R)]-N-(2-hydroxy-1-phenylethyl-2-ethoxy-3-[4-{3-(3,4-dihydro-2H-benzo[b][1,4]oxazin-4-yl)propylamino}phenyl]propanamide hydrochloride salt

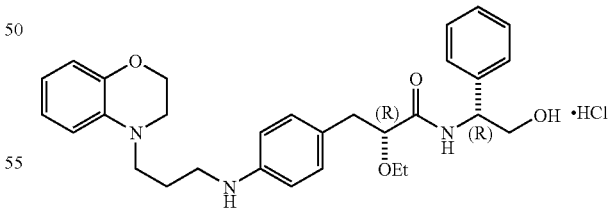

To a dry methanolic HCl solution (2 ml) [2R,N(1R)]-N-(2-hydroxy-1-phenylethyl)-2-ethoxy-3-[4-{3-(3,4-dihydro2H-benzo[b][1,4]oxazin-4-yl)propylamino}phenyl]propanamide (95 mg, 0.19 mmol) obtained in example 35, was added and the mixture was stirred at RT for 5 min. Then the reaction mixture was condensed and azeotroped using dry benzene on rotary evaporator. The residue was dried on high-vacuum to obtain the title compound as a brown solid mass (100% yield, mp: 69-70° C.).

EXAMPLE 43

(−)-(S)-3-[4-{3-(3,4-Dihydro-2H-benzo[b][1,4]ox-azin-4-yl)propylamino}phenyl]-2-ethoxypropanoic acid

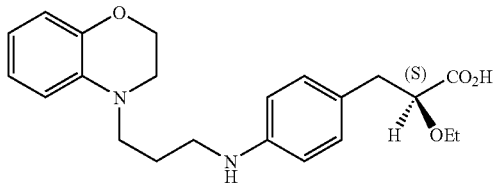

[α]$_D$: −17° (c, 1.0 MeOH).

$^1$H NMR (200 MHz, CDCl$_3$) δ: 1.19 (t, J=7.4 Hz, 3H), 1.94 (q, J=7.4 Hz, 2H), 2.90 (dd, J=14.0 and 7.0 Hz, 1H), 3.05 (dd, J=14.0 and 4.9 Hz, 1H), 3.21 (t, J=6.8 Hz, 2H), 3.25-3.40 (m, 5H), 3.40-3.62, (m, 1H), 4.00-4.17 (m, 1H), 4.18-4.22 (m, 2H), 6.59 (d, J=8.3 Hz, 2H), 6.65-6.85 (m, 4H), 7.06 (d, J=8.3 Hz, 2H).

IR (neat) cm$^{-1}$: 3500, 1725.

Mass m/z (CI): 385 (M+1).

EXAMPLE 44

(+)-(R)-3-[4-{3-(3,4-Dihydro-2H-benzo[b][1,4]ox-azin-4-yl)propylamino}phenyl]-2-ethoxypropanoic acid

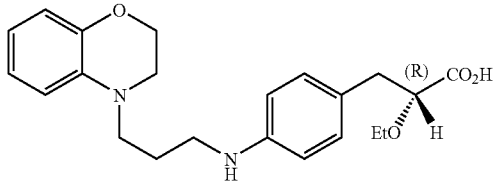

[α]$_D$: 16.8° (c, 1.0 MeOH).

$^1$H NMR (200 MHz, CDCl$_3$) δ: 1.19 (t, J=7.4 Hz, 3H), 1.94 (q, J=7.4 Hz, 2H), 2.90 (dd, J=14.0 and 7.0 Hz, 1H, 3.05 (dd, J=14.0 and 4.9 Hz, 1H), 3.21 (t, J=6.8 Hz, 2H), 3.25-3.40 (m, 5H), 3.40-3.62 (m, 1H), 4.00-4.17 (m, 1H), 4.18-4.22 (m, 2H), 6.59 (d, J=8.3 Hz, 2H), 6.65-6.85 (m, 4H), 7.06 (d, J=8.3 Hz, 2H).

IR (neat) cm$^{-1}$: 3500, 1725.

Mass m/z (CI): 385 (M+1).

EXAMPLE 45

Ethyl 3-[4-{3-(7-fluoro-3,4-dihydro-2H-benzo[b][1,4]oxazin-4-yl)pryopylamino}phenyl]-2-ethoxypropanoate

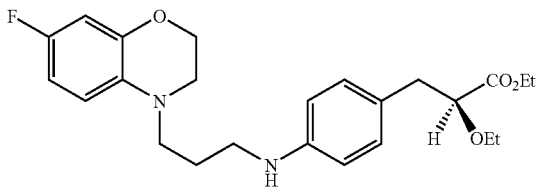

(S)-Ethyl 2-ethoxy-3-(4-aminophenyl)propanoate (2.20 g, 1 eq, 9.28 mmol) obtained in preparation 20, 3-(7-fluoro-3,4-dihydro-2H-benzo[b][1,4]oxazin-4-yl)propylbromide (3.30 g, 1.3 eq, 12.06 mmol) obtained in preparation 10, and anhydrous K$_2$CO$_3$ (3.84 g, 3 eq, 27.84 mmol), and tetrabutyl ammonium bromide (597 mg, 0.2 eq., 1.85 mmol) were heated at 90° C. in dry toluene (47 mL) for 20 h. The reaction time was diluted with ethyl acetate, washed with water and brine. The residue was chromatographed using ethyl acetate and hexane to afford the title compound (1.78 g, yield 44.5%) as viseous liquid.

[α]$_D$: −9.20 (c 1.0, MeOH).

$^1$H NMR (200 MHz, CDCl$_3$) δ: 1.17 (t, J=7 Hz, 3H), 1.23 (t, J=7 Hz, 3H), 1.89 (q, J=6.8 Hz, 2H), 2.90 (d, J=6.5 Hz, 2H), 3.10-3.42 (m, 7H), 3.45-3.65 (m, 1H), 3.95 (t, J=6.7 Hz, 1H), 4.10-4.30 (m, 4H), 6.40-6.70 (m, aromatics, 5H), 7.05 (d, J=8.4 Hz, 2H).

IR (neat) cm$^{-1}$: 3394 (br), 2978, 1740, 1617, 1514.

Mass m/z (CI): 431 (M+1).

EXAMPLE 46

(S)-3-[4-{3-(7-Fluoro-3,4-dihydro-2H-benzo[b][1,4]oxazin-4-yl)propylamino}phenyl]-2-ethoxypropanoic acid

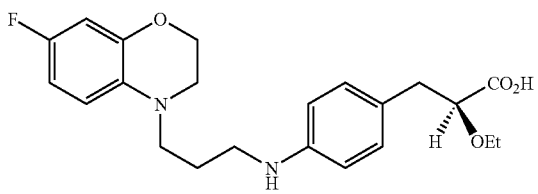

(S)-Ethyl 3-[4-{3-(7-fluoro-3,4-dihydro-2H-benzo[b][1,4]oxazin-4-yl)propylamino}phenyl]-2-ethoxypropanoate (1.7 g, 1 eq, 3.95 mmol) obtained in example 45, was hydrolyzed using lithium hydroxide monohydrate (249 mg, 1.5 eq, 5.93 mmol), in methanol-THF-water at RT till all the starting material is consumed (4 to 5 h). The reaction mixture was diluted with water, acidified (pH ~4-5) with dil. HCl and then extracted with ethyl acetate. The ethyl acetate layer was dried over anhydrous sodium sulfate and concentrated on rotary evaporator. The residue was chromatographed using ethyl acetate and hexanes→methanol and chloroform to afford the title compound (1.5 g, yield 94%) as viscous liquid.

[α]$_D$: −16.1° (c 1.0, MeOH).

Chiral HPLC: >98% ee.

$^1$H NMR (200 MH, CDCl$_3$) δ: 1.19 (t, J=7.4 Hz, 3H), 1.94 (quintet, J=7.4 Hz, 2H), 2.85-3.10 (m, 2H), 3.10-3.20 (m, 6H), 3.40-3.70 (m, 2H), 3.90-4.10 (m, 1H), 4.10-4.30 (m, 2H), 6.20 (bs, NH, CO$_2$H), 6.42-6.70 (m, aromatics, 5H), 7.07 (d, J=8.3 Hz, 2H).

IR (KBr) cm$^{-1}$: 3394, 1725, 1619.

Mass m/z (CI): 403 (M+1).

EXAMPLE 47

(S)-3-[4-{3-(7-Fluoro-3,4-dihydro-2H-benzo[b][1,4]oxazin-4-yl)propylamino}phenyl]-2-ethoxypropanoic acid L-arginine salt

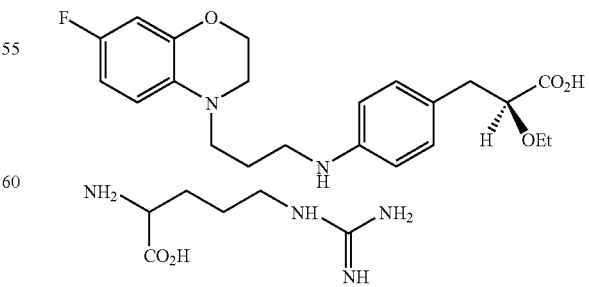

(S)-3-[4-{3-(7-Fluoro-3,4-dihydro-2H-benzo[b][1,4]ox-azin-4-yl)propylamino}phenyl]-2-ethoxypropanoic acid (300 mg, 1 eq, 0.74 mmol) obtained in example 46, and L-arginine (130 mg, 1 eq, 0.74 mmol) were taken in dry methanol (4 ml), and stirred at RT for 2-3 h. The solvent was removed on rotavapour followed by benzene azeotrope. The residue was dried under high vacuum pump to yield the title compound as a free following solid (yield 100%).

Mp: 114-116° C.

EXAMPLE 48

(S)-3-[4-{3-(7-Fluoro-3,4-dihydro-2H-benzo-[b][1,4]oxazin-4-yl)propylamino}phenyl]-2-exthoxypropanoic acid magnesium salt

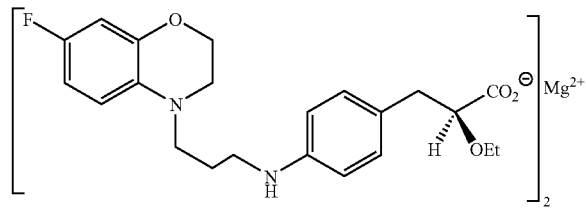

(S)-3-[4-{3-(7-Fluoro-3,4-dihydro-2H-benzo-[b][1,4]oxazin-4-yl)propylamino}phenyl]-2-exthoxypropanoic acid (1.13 g, 1.0 eq, 2.81 mmol), obtained in example 46, in dry ethanol (15 mL) was treated with Mg(OMe)$_2$ (121 mg, 0.5 eq, 1.4 mmol). The resulting mixture was heated at 55-60° C. for 7-8 h. The reaction mixture was condensed on rotavapour, azeotroped with benzene, and finally dried on high vacuum pump. The sticky mass was triturated with hexanes to obtain the desired salt as a powdery solid (quantitative yield).

Mp: 240-242° C. (dec.).

EXAMPLE 49

Ethyl 3-[4-{3-(7-fluoro-3,4-dihydro-2H-benzo[b][1,4]oxazin-4-yl)propylamino}phenyl]-2-methoxypropanoate

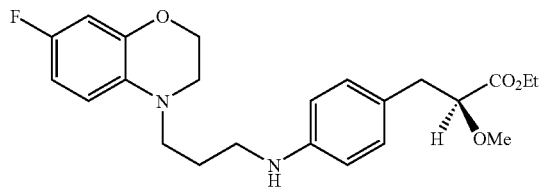

(S)-Ethyl 2-methoxy-3-(4-aminophenyl)propanoate (800 mg, 1.0 eq, 3.58 mmol) obtained in preparation 21, 3-(7-fluoro-3,4-dihydro-2H-benzo[b][1,4]oxazin-4-yl)propyl-bromide (1.27 g, 1.3 eq, 4.65 mmol) obtained in preparation 10, and anhydrous K$_2$CO$_3$ (1.48 g, 3 eq, 10.79 mmol), and tetrabutyl ammonium bromide (576 mg, 0.5 eq., 1.79 mmol) were heated at 90° C. in dry toluene (20 mL) for 9 h. The reaction mixture was diluted with ethyl acetate, washed with water and brine. The residue was chromatographed using ethyl acetate and hexane to afford the title compound (1.1 g, yield 73%) as viscous liquid.

[α]$_D$: −4.0° (c 1.0, MeOH).

$^1$H NMR (200 MHz, CDCl$_3$) δ: 1.25 (t, J=7.3 Hz, 3H), 1.89 (q, J=7.0 Hz, 2H), 2.91 (d, J=6.0 Hz, 2H), 3.05-3.42 (m, 6H), 3.36 (s, 3H); 3.90 (t, J=6.4 Hz, 1H), 4.10-4.30 (m, 4H), 6.40-6.70 (m, aromatics, 5H); 7.05 (aromatics, 2H).

IR (neat) cm$^{-1}$: 3385 (br), 2934, 1741, 1617, 1514.

Mass m/z (CI): 417 (M+1).

EXAMPLE 50

(S)-3-[4-{3-(7-Fluoro-3,4-dihydro-2H-benzo[b][1,4]oxazin-4-yl)propylamino}phenyl]-2-methoxypropanoic acid

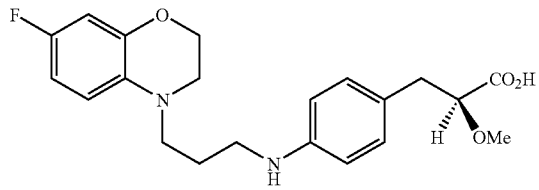

(S)-Ethyl 3-[4-{3-(7-fluoro-3,4-dihydro-2H-benzo[b][1,4]oxazin-4-yl)propylamino}phenyl]-2-methoxypropanoate (1.0 g, 1 eq, 2.4 mmol) obtained in example 49, was hydrolyzed using lithium hydroxide monohydrate (151 mg, 1.5 eq, 3.6 mmol) in methanol-THF-water at RT till all the starting material is consumed (4 to 5 h). The reaction mixture was diluted with water, acidified (pH ~4-5) with dil. HCl and then extracted with ethyl acetate. The ethyl acetate layer was dried over anhydrous sodium sulfate and concentrated on rotary evaporator. The residue was chromatographed using ethyl acetate and hexanes→methanol and chloroform to afford the title compound (650 mg, yield 70%) as viscous liquid.

[α]$_D$: −14.2° (c 1.0, MeOH).

Chiral HPLC: >98% ee.

$^1$H NMR (200 MHz, CDCl$_3$) δ: 1.9 (quintet, J=7.4 Hz, 2H), 2.85-3.10 (m, 2H), 3.10-3.38 (m, 6H), 3.40 (s, 3H); 3.90-4.05 (m, 1H); 4.24 (t, J=4.2 Hz, 2H); 6.42-6.70 (m, aromatics, 5H); 7.05 (d, J=8.0 Hz, 2H).

IR (neat) cm$^{-1}$: 3396, 2936, 1727, 1614, 1513.

Mass m/z (CI): 389 (M+1).

EXAMPLE 51

(S)-3-[4-{3-(7-Fluoro-3,4-dihydro-2H-benzo[b][1,4]oxazin-4-yl)propylamino}phenyl]-2-methoxypropanoic acid magnesium salt

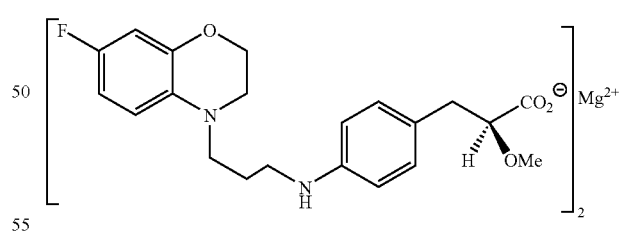

(S)-3-[4-{3-(7-Fluoro-3,4-dihydro-2H-benzo[b][1,4]oxazin-4-yl)propylamino}phenyl]-2-methoxypropanoic acid (400 mg, 1.0 eq, 1.03 mmol), obtained in example 50, in dry methanol (5 mL) was treated with Mg(OMe)$_2$ (44.3 mg, 0.5 eq, 0.51 mmol). The resulting mixture was heated at 55-60° C. for 7-8 h. The reaction mixture was condensed on rotavapour, azeotroped with benzene, and finally dried on high vacuum pump. The sticky mass was triturated with hexanes to obtain the desired salt as a powdery solid (quantitative yield).

Mp: 210-212° C. (dec.).

EXAMPLE 52

Ethyl 3-[4-{3-(2-methyl-7-fluoro-3,4-dihydro-2H-benzo[b][1,4]oxazin-4-yl)propylamino}phenyl]-2-ethoxypropanoate

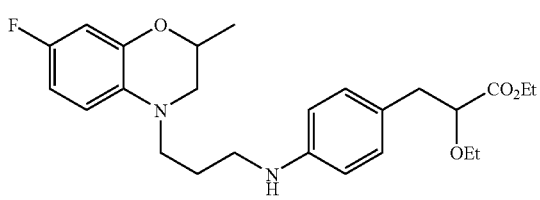

Ethyl 2-ethoxy-3-(4-aminophenyl)propanoate (500 mg, 1 eq, 2.11 mmol) obtained in preparation 1, 3-(2-methyl-7-fluoro-3,4-dihydro-2H-benzo[b][1,4]oxazin-4-yl)propylbromide (670 mg, 1.1 eq, 2.32 mmol) obtained in preparation 17, and anhydrous $K_2CO_3$ (875 mg, 3 eq, 6.33 mmol), and tetrabutyl ammonium bromide (340 mg, 0.5 eq., 1.05 mmol) were heated at 90° C. in dry toluene (11 mL) for 12 h. The reaction mixture was diluted with ethyl acetate, washed with water and brine. The residue was chromatographed using ethyl acetate and hexane to afford the title compound (320 mg, yield 32%) in the form of mixture of diastereomers as viscous liquid.

$^1$H NMR (200 MHz, $CDCl_3$) δ: 1.10-1.25 (m, 9H), 1.80-2.00 (m, 2H), 2.82-3.02 (m, 2H), 3.10-3.50 (m, 2H), 3.28-3.44 (m, 3H), 3.50-3.65 (m, 1H); 3.90-4.00 (m, 1H), 4.10-4.30 (m, 3H), 6.40-6.80 (aromatics, 5H), 7.00-7.20 (aromatics, 2H).

IR (neat) $cm^{-1}$: 3389 (br), 2929, 1740, 1617, 1515.

Mass m/z (CI): 445 (M+1).

EXAMPLE 53

3-[4-{3-(2-methyl-7-Fluoro-3,4-dihydro-2H-benzo[b][1,4]oxazin-4-yl)propylamino}phenyl]-2-ethoxypropanoic acid

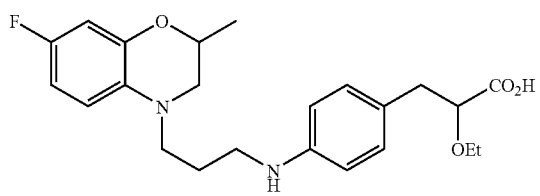

Ethyl 3-[4-{3-(2-methyl-7-fluoro-3,4-dihydro-2H-benzo[b][1,4]oxazin-4-yl)propylamino}phenyl]-2-ethoxypropanoate (320 mg, 1 eq, 0.72 mmol) obtained in example 52, was hydrolyzed using lithium hydroxide monohydrate (46 mg, 1.5 eq, 1.08 mmol), in methanol-THF-water at RT till all the starting material is consumed (4 to 5 h). The reaction mixture was diluted with water, acidified (pH ~4-5) with dil. HCl and then extracted with ethyl acetate. The ethyl acetate layer was dried over anhydrous sodium sulfate and concentrated on rotary evaporator. The residue was chromatoghaphed using methanol and chloroform to afford the title compound (190 mg, yield 64%) as viscous liquid.

$^1$H NMR (200 Mz, $CDCl_3$) δ: 1.21 (t, J=7.1 Hz, 3H), 1.36 (d, J=6.4 Hz, 3H), 1.92 (quintet, J=6.8 Hz, 2H), 2.90-3.10 (m, 2H), 3.10-3.40 (m, 6H), 3.42-3.60 (m, 2H); 4.06 (dd, J=6.8, 3.9 Hz, 1H), 4.20-4.35 (m, 1H); 6.50-6.62 (aromatics, 5H), 7.07 (d, J=8.3 Hz, 2H).

IR (KBr) $cm^{-1}$: 3387, 2927, 1726, 1615, 1514.

Mass m/z (CI): 417 (M+1).

EXAMPLE 54

3-[4-{3-(2-methyl-7-Fluoro-3,4-dihydro-2H-benzo[b][1,4]oxazin-4-yl)propylamino}phenyl]-2-ethoxypropanoic acid magnesium salt

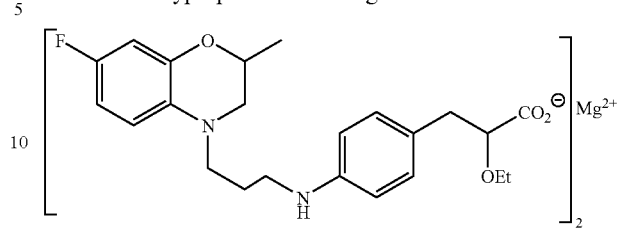

3-[4-{3-(2-methyl-7-Fluoro-3,4-dihydro-2H-benzo[b][1,4]oxazin-4-yl)propylamino}phenyl]-2-ethoxypropanoic acid (170 mg, 1.0 eq, 0.41 mmol), obtained in example 53, in dry methanol (5 mL) was treated with $Mg(OMe)_2$ (17.6 mg, 0.5 eq, 0.21 mmol). The resulting mire was heated at 55-60° C. for 7-8 h. The reaction mixture was condensed on rotavapour, azeotroped with benzene, and finally dried one high vacuum pump. The sticky mass was triturated with hexanes to obtain the desired salt as a powdery solid (quantitative yield).

Mp: 110-112° C.

EXAMPLE 55

Ethyl 3-[4-{3-(2-methyl-3,4-dihydro-2H-benzo[b][1,4]oxazin-4-yl)propylamino}phenyl]-2-ethoxypropanoate

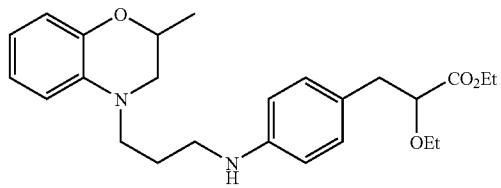

Starting from ethyl 2-ethoxy-3-(4-aminophenyl)propanoate (438 mg, 1 eq, 1.85 mmol) obtained in preparation 1, and 3-(2-methyl-3,4-dihydro-2H-benzo[b][1,4]oxazin-4-yl)propylbromide (550 mg, 1.1 eq, 2.32 mmol) obtained in preparation 18, and following the procedure of example 52 the title compound (300 mg, yield 35%) was obtained in the form of mixture of diastereomers as viscous liquid.

$^1$H NMR (200 MHz, $CDCl_3$) δ: 1.17 (t, J=7.0 Hz, 3H); 1.23 (t, J=7.0 Hz, 3H); 1.35 (d, J=6.4 Hz, 3H); 1.80-2.00 (m, 2H), 2.91 (d, J=6.7 Hz, 2H); 3.00-3.42 (m, 7H); 3.45-3.65 (m, 1H); 3.95 (t, J=6.7 Hz, 1H), 4.10-4.30 (m, 3H), 6.53 (d, J=8.3 Hz, 2H); 6.65 (t, J=7.8 Hz, 2H); 6.79 (d, J=7.8 Hz, 2H); 7.06(d, J=8.3 Hz, 2H).

IR (neat) $cm^{-1}$: 3400 (br), 2976, 1741, 1616, 1520.

Mass m/z (CI): 427 (M+1).

EXAMPLE 56

3-[4-{3-(2-methyl-3,4-dihydro-2H-benzo[b][1,4]oxazin-4-yl)propylamino}phenyl]-2-ethoxypropanoic acid

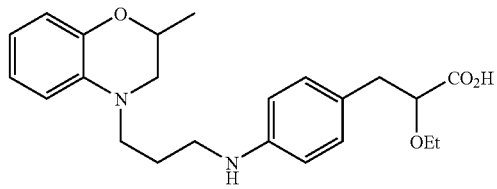

Ethyl 3-[4-{3-(2-methyl-3,4-dihydro-2H-benzo[b][1,4]oxazin-4-yl)propylamino}phenyl]-2-ethoyxypropanoate (300 mg, 1 eq, 0.72 mmol), obtained in example 55 was hydrolyzed following the procedure of example 53 to obtain the title compound (170 mg, yield 61%) as viscouis liquid.

$^1$H NMR (200 MHz, CDCl$_3$) δ: 1.17 (t, J=7.0 Hz, 3H); 1.34 (d, J=6.1 Hz, 3H); 1.80-2.00 (m, 2H), 2.80-3.70 (m, 10H), 4.02 (dd, J=7.3, 4.5 Hz, 1H), 4.10-4.30 (m, 1H), 5.6 (bs, 2H, CO$_2$H, NH); 6.55 (d, J=8.3 Hz, 2H); 6.64 (t, J=7.8 Hz, 2H); 6.79 (d, J=7.8 Hz, 2H); 7.06 (d, J=8.3 Hz, 2H).

IR (KBr) cm$^{-1}$: 3393, 2974, 1726, 1617, 1503.

Mass m/z (CI): 399 (M+1).

EXAMPLE 57

3-[4-{3-(2-methyl-3,4-dihydro-2H-benzo[b][1,4] oxazin-4-yl)propylamino}phenyl]-2-ethoxypropanoic acid magnesium salt

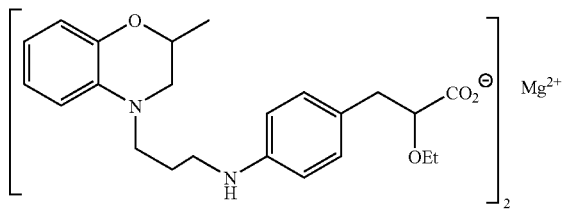

From 3-[4-{3-(2-methyl-3,4-dihydro-2H-benzo[b][1,4] oxazin-4-yl)propylamino}phenyl]-2ethoxypropanoic acid (155 mg, 1.0 eq, 0.39 mmol), obtained in example 56 and Mg(OMe)$_2$ (16.5 mg, 0.5 eq, 0.20 mmol) the desired salt as a powdery solid (quantitative yield) following the procedure of example 54.

Mp: 102-104° C.

EXAMPLE 58

Ethyl (2S)-3-[4-{3-(2-methyl-3,4-dihydro-2H-benzo[b][1,4]oxazin-4-yl)propylamino}phenyl]-2-methoxypropanoate

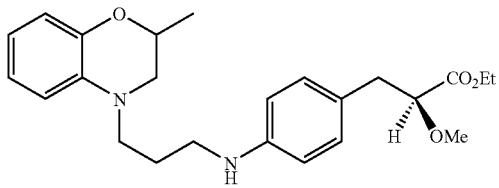

Starting from ethyl (S)-2-methoxy-3-(4-aminophenyl) propanoate (500 mg, 1 eq, 2.24 mmol) obtained in preparation 21, and 3-(2-methyl-3,4-dihydro-2H-benzo[b][1,4] oxazin-4-yl)propylbromide (666 mg, 1.1 eq, 2.47 mmol) obtained in preparation 18, and following the procedure of example 52, the title compound (340 mg, yield 38%) was obtained in the form of mixture of diastereomers as viscous liquid.

$^1$H NMR (200 MHz, CDCl$_3$) δ: 1.25 (t, J=7.2 Hz, 3H); 1.36 (d, J=6.4 Hz, 3H); 1.80-2.00 (m, 2H), 2.92 (d, J=6.2 Hz, 2H); 3.02-3.50 (m, 9H); 3.90 (t, J=6.2 Hz, 1H), 4.10-4.30 (m, 3H), 6.54 (d, J=8.3 Hz, 2H); 6.65 (t, J=7.2 Hz, 2H); 6.80 (d, J=7.2 Hz, 2H); 7.05 (d, J=8.3 Hz, 2H).

IR (neat) cm$^{-1}$: 3398 (br), 2928, 1741, 1613, 1520.

Mass m/z (CI): 413 (M+1).

EXAMPLE 59

(2S)-3-[4-{3-(2-methyl-3,4-dihydro-2H-benzo[b][1, 4]oxazin-4-yl)propylamino}phenyl]-2-methoxypropanoic acid

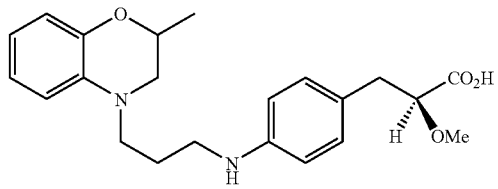

Ethyl (2S)-3-[4-{3-(2-methyl-3,4-dihydro-2H-benzo[b] [1,4]oxazin-4-yl)propylamino}phenyl]-2-methoxypropanoate (170 mg, 1 eq, 0.413 mmol), obtained in example 58, was hydrolyzed following the procedure of example 53, to obtain the title compound (100 mg, yield 63%) as viscous liquid.

$^1$H NMR (200 MHz, CDCl$_3$) δ: 1.35 (d, J=6.5 Hz, 3H); 1.80-2.00 (m, 2H), 2.85-3.60 (m, 11H); 3.98 (dd, J=7.0, 4.3 Hz, 1H), 4.15-4.30 (m, 1H), 6.55 (d, J=8.3 Hz, 2H); 6.65 (t, J=7.2 Hz, 2H); 6.79 (d, J=7.2 Hz, 2H); 7.05 (d, J=8.3 Hz, 2H).

IR (KBr) cm$^{-1}$: 3391, 2930, 1727, 1608, 1506.

Mass m/z (CI): 385 (M+1).

EXAMPLE 60

(2S)-3-[4-{3-(2-methyl-3,4-dihydro-2H-benzo[b][1, 4]oxazin-4-yl)propylamino}phenyl]-2-methoxypropanoic acid magnesium salt

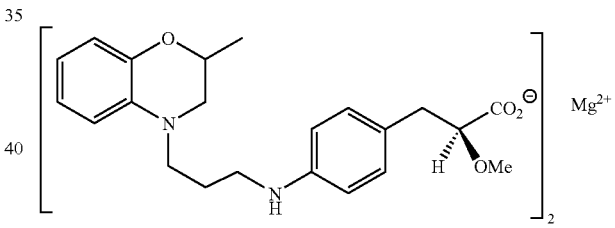

From (2S)-3-[4-{3-(2-methyl-3,4-dihydro-2H-benzo[b] [1,4]oxazin-4-yl)propylamino}phenyl]-2-ethoxypropanoic acid (90 mg, 1.0 eq, 0.23 mmol), obtained in example 59, and Mg(OMe)$_2$ (10.1 mg, 0.5 eq, 0.12 mmol) the desired salt as a powdery solid (quantitative yield) following the procedure of example 54.

Mp: 160-162° C.

EXAMPLE 61

Ethyl 3-[4-{3-(2-propyl-3,4-dihydro-2H-benzo[b][1, 4]oxazin-4-yl)propylamino}phenyl]-2-ethoxypropanoate

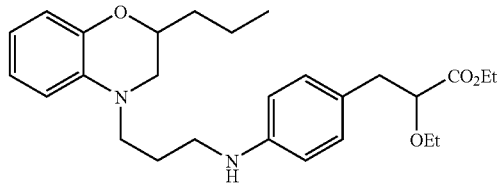

Starting from ethyl 2-ethoxy-3-(4-aminophenyl)propanoate (325 mg, 1 eq, 1.37 mmol) obtained in preparation 1, and 3-(2-propyl-3,4-dihydro-2H-benzo[b][1,4]oxazin-4-yl)propylbromide (450 mg, 1.1 eq, 1.51 mmol) obtained in preparation 19, and following the procedure of example 52, the title compound (343 mg, yield 69%) was obtained in the form of mixture of diastereomers as viscous liquid.

$^1$H NMR (200 MHz, CDCl$_3$) δ: 0.97 (t, J=7.0 Hz, 3H); 1.17 (t, J=7.2 Hz, 3H); 1.22 (t, J=7.3 Hz, 3H); 1.40-1.80 (m, 4H); 1.91 (quintet, J=6.7 Hz, 2H); 2.90 (d, J=6.4 Hz, 2H); 3.00-3.42 (m, 7H); 3.45-3.65 (m, 1H); 3.94 (t, J=6.4 Hz, 1H), 4.00-4.22 (m, 3H); 6.52 (d, J=8.3 Hz, 2H); 6.64 (t, J=7.0 Hz, 2H); 6.78 (d, J=7.2 Hz, 2H); 7.05 (d, J=8.3 Hz, 2H).

IR (neat) cm$^{-1}$: 3400 (br), 2959, 1741, 1616, 1520.

Mass m/z (CI): 455 (M+1).

EXAMPLE 62

3-[4-{3-(2-propyl-3,4-dihydro-2H-benzo[b][1,4]oxazin-4-yl)propylamino}phenyl]-2-ethoxypropanoic acid

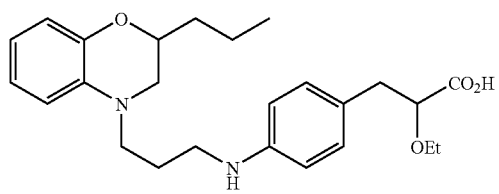

Ethyl 3-[4-{3-(2-propyl-3,4-dihydro-2H-benzo[b][1,4]oxazin-4-yl)propylamino}phenyl]-2-ethoxypropanoate (305 mg, 1 eq, 0.67 mmol), obtained in example 61, was hydrolyzed following the procedure of example 53 to obtain the title compound (177 mg, yield 62%) as viscous liquid.

$^1$H NMR (200 MHz, CDCl$_3$) δ: 0.97 (t, J=7.0 Hz, 3H); 1.18 (t, J=7.2 Hz, 3H); 1.40-1.80 (m, 4H); 1.92 (quintet, J=6.7 Hz, 2H), 2.80-3.62 (m, 10 H); 3.95-4.15 (m, 2H); 4.60 (bs, 2H); 6.55 (d, J=8.3 Hz, 2H); 6.64 (t, J=7.0 Hz, 2H); 6.79 (d, J=7.2 Hz, 2H); 7.06 (d, J=8.3 Hz, 2H).

IR (KBr) cm$^{-1}$: 3500, 2931, 1724, 1606, 1504.

Mass m/z (ES): 427 (M+1), 853 (M$_2$+1).

EXAMPLE 63

3-[4-{3-(2-propyl-3,4-dihydro-2H-benzo[b][1,4]oxazin-4-yl)propylamino}phenyl]-2-ethoxypropanoic acid magnesium salt

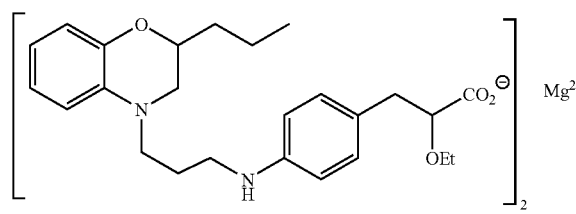

From, 3-[4-{3-(2-propyl-7-3,4-dihydro-2H-benzo[b][1,4]oxazin-4-yl)propylamino}phenyl]-2-ethoxypropanoic acid (164 mg, 1.0 eq, 0.39 mmol), obtained in example 62, and Mg(OMe)$_2$ (16.5 mg, 0.5 eq, 0.20 mmol) the desired salt as a powdery solid (quantitative yield) following the procedure of example 54.

Mp: 104-106° C.

EXAMPLE 64

Ethyl (2S)-3-[4-{3-(2-propyl-3,4-dihydro-2H-benzo[b][1,4]oxazin-4-yl)propylamino}phenyl]-2-methoxypropanoate

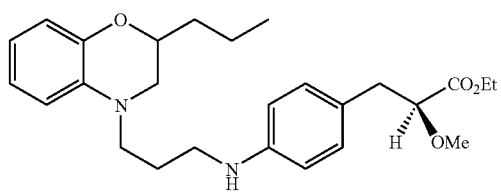

Starting from ethyl (S)-2-methoxy-3(4-aminophenyl)propanoate (312 mg, 1 eq, 1.1.40 mmol) obtained in preparation 21, and 3-(2-propyl-3,4-dihydro-2H-benzo[b][1,4]oxazin-4-yl)propylbromide (460 mg, 1.1 eq, 1.54 mmol) obtained in preparation 19, and following the procedure of example 52, the title compound (255 mg, yield 69%) was obtained in the form of mixture of diastereomers as viscous liquid.

$^1$H NMR (400 MHz, CDCl$_3$) δ: 0.99 (t, J=6.8 Hz, 3H); 1.26 (t, J=7.2 Hz, 3H); 1.47-1.61 (m, 3H); 1.69-1.74 (m, 1H); 1.89-1.97 (m, 2H), 2.92 (d, J=4.0 Hz, 1H); 2.93 (d, J=2.0 Hz, 1H); 3.09 (dd, J=11.2, 7.8 Hz, 1H); 3.18-3.30 (m, 3H; 3.36 (s, 3H); 3.31-3.48 (m, 2H); 3.90 (t, J=6.0 Hz, 1H), 4.06-4.10 (m, 1H); 4.19 (q, J=7.2 Hz, 2H); 6.54 (d, J=8.8 Hz, 2H); 6.55-6.65 (aromatics, 2H); 6.79 (d, J=7.2 Hz, 2H); 7.04 (d, J=8.8 Hz, 2H).

IR (neat) cm$^{-1}$: 3396 (br), 2930, 1741, 1613, 1518.

Mass m/z (CI): 441 (M+1).

EXAMPLE 65

(2S)-3-[4-{3-(2-propyl-3,4-dihydro-2H-benzo[b][1,4]oxazin-4-yl)propylamino}phenyl]-2-methoxypropanoic acid

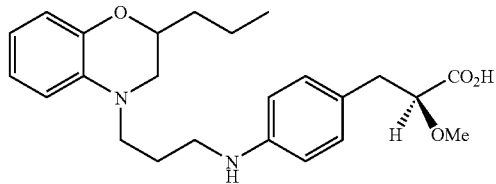

Ethyl (2S)-3-[4-{3-(2-propyl-3,4-dihydro-2H-benzo[b][1,4]oxazin-4-yl)propylamino}phenyl]-2-methoxypropanoate (240 mg, 1 eq, 0.55 mmol), obtained in example 64, was hydrolyzed following the procedure of example 53 to obtain the title compound (164 mg, yield 73%) as viscous liquid.

$^1$H NMR (200 MHz, CDCl$_3$) δ: 0.96 (t, J=7.0 Hz, 3H); 1.44-1.67 (m, 4H); 1.91 (quintet, J=7.0 Hz, 2H), 2.90-3.33 (m, 8 H); 3.38 (s, 3H); 3.92-4.06 (m, 2H); 4.60 (bs, 2H); 6.55-6.66 (aromatics, 4H); 6.78 (d, J=7.4 Hz, 2H); 7.06 (d, J=8.2 Hz, 2H).

IR (KBr) cm$^{-1}$: 3397, 2930, 1727, 1606, 1504.

Mass m/z (ES): 413 (M+1), 825 (M$_2$+1), 1237 (M$_3$+1).

EXAMPLE 66

(S)-3-[4-{3-(2-propyl-3,4-dihydro-2H-benzo[b][1,4]oxazin-4-yl)propylamino}phenyl]-2-methoxypropanoic acid magnesium salt

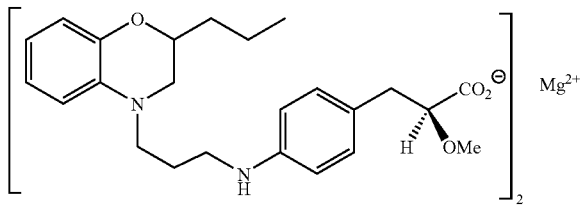

From (2S)-3-[4-{3-(2-propyl-7-3,4-dihydro-2H-benzo[b][1,4]oxazin-4-yl)propylamino}phenyl]-2-ethoxypropanoic acid (140 mg, 1.0 eq, 0.34 mmol), obtained in example 65 and mg(OMe)$_2$ (14.5 mg, 0.5 eq, 0.17 mmol) the desired salt as a powdery solid (quantitative yield) following the procedure of example 54.
Mp: 172-174° C.

EXAMPLE 67

Ethyl 2-isopropoxy-3-[4-{3-(7-fluoro-3,4-dihydro-2H-benzo[b][1,4]oxazin-4-yl)propylamino}phenyl]propanoate

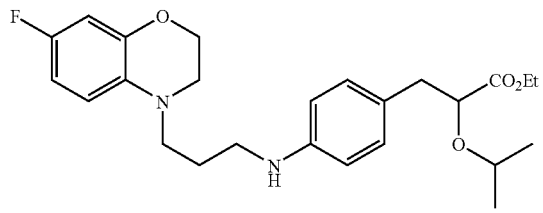

Starting from ethyl 2-isopropoxy-3-(4-aminophenyl)propanoate (650 mg, 1 eq, 2.59 mmol) obtained in preparation 22 and 3-(7-fluoro-3,4-dihydro-2H-benzo[b][1,4]oxazin-4-yl)propylbromide (781 mg, 1.1 eq, 2.85 mmol) obtained in preparation 10, and following the procedure of example 52, the title compound (700 mg, yield 61%) was obtained a viscous liquid.
$^1$H NMR (200 MHz, CDCl$_3$) δ: 0.98 (d, J=6.2 Hz, 3H); 1.16 (d, J=6.2 Hz, 3H); 1.23 (t, J=7.2 Hz, 3H); 1.81-1.88 (m, 2H; 2.85-2.89 (m, 2H); 3.17-3.24 (m, 4H); 3.33 (t, J=7.3 H, 2H); 3.40-3.60 (m, 1H); 3.99 (t, J=6.0 Hz, 1H); 4.11-4.23 (m, 4H); 6.48-6.55 (aromatics, 3H); 6.63 (d, J=8.3 Hz, 2H); 7.08 (d, J=8.3 Hz, 2H).
IR (neat) cm$^{-1}$: 3396 (br), 2939, 1729, 1615, 1514.
Mass m/z (CI): 445 (M+1).

EXAMPLE 68

2-Isopropoxy-3-[4-{3-(7-fluoro-3,4-dihydro-2H-benzo[b][1,4]oxazin-4-yl)propylamino}phenyl]propanoic acid

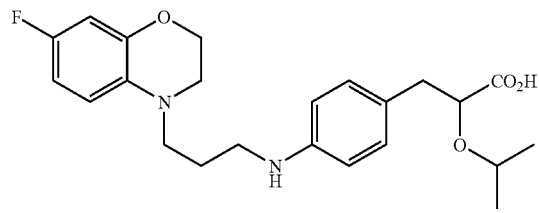

Ethyl 2-isopropoxy-3-[4-{3-(7-fluoro-3,4-dihydro-2H-benzo[b][1,4]oxazin-4-yl)propylamino}phenyl]propanoate (600 mg, 1 eq, 1.35 mmol), obtained in example 67, was hydrolyzed following the procedure of example 53 to obtain the title compound (240 mg, yield 43%) as viscous liquid.

$^1$H NMR (200 MHz, CDCl$_3$) δ: 1.01 (d, J=6.2 Hz, 3H); 1.16 (d, J=6.2 Hz, 3H); 1.91(quintet, J=6.7 Hz, 2H); 2.84 (dd, J=14, 8.1 Hz, 1H); 3.00 (dd, J=14, 4.2 Hz, 1H); 3.16-3.34 (m, 6H); 3.42-3.60 (m, 1H); 4.06 (dd, J=8.1, 4.2 Hz, 1H), 4.20-4.25 (m, 2H), 6.09 (bs, 2H); 6.47-6.58 (aromatics, 5H); 7.06 (d, J=8.3 Hz, 2H).
IR (neat) cm$^{-1}$: 3388 (br), 2932, 1722, 1616, 1513.
Mass m/z (CI): 417 (M+1).

EXAMPLE 69

2-isopropoxy-3-[4-{3-(7-fluoro-3,4-dihydro-2H-benzo[b][1,4]oxazin-4-yl)propylamino}phenyl]propanoic acid magnesium salt

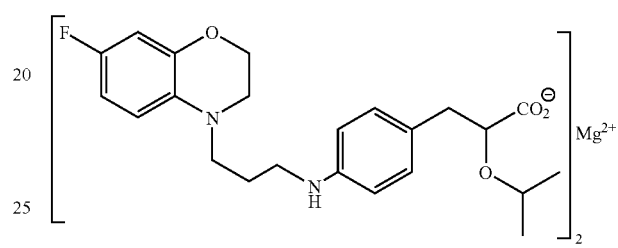

From 2-isopropoxy-3-[4-{3-(7-fluoro-3,4-dihydro-2H-benzo[b][1,4]oxazin-4-yl)propylamino}phenyl]propanoic acid (240 mg, 1.0 eq, 0.57 mmol), obtained from example 68, and Mg(OMe)$_2$ (25 mg, 0.5 eq, 0.29 mmol) the desired salt as a powdery solid (quantitative yield) following the procedure of example 54.
Mp: 110° C.

EXAMPLE 70

Ethyl (2S)-3-[4-{3-(2-methyl-7-fluoro-3,4-dihydro-2H-benzo[b][1,4]oxazin-4-yl)propylamino}phenyl]-2-methoxypropanoate

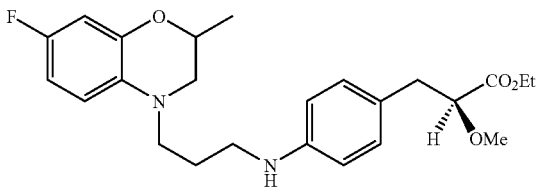

Starting from ethyl (S)-2-methoxy-3-(4-aminophenyl)propanoate (500 mg 1 eq, 2.24 mmol) obtained in preparation 21 and 3-(2-methyl-7-fluoro-3,4-dihydro-2H-benzo[b][1,4]oxazin-4-yl)propylbromide (711 mg, 1.1 eq, 2.47 mmol) obtained in preparation 17, and following the procedure of example 52, the title compound (380 mg, yield 40%) was obtained in the form of mixture of diastereomers as viscous liquid.
$^1$H NMR (200 MHz, CDCl$_3$) δ: 1.20-1.40 (m, 6H); 1.80-2.00 (m, 2H), 2.90-3.02 (m, 2H); 3.02-3.40 (m, 9H); 3.90 (t, J=6.3 Hz, 1H), 4.10-4.30 (m, 3H), 6.40-6.60 (aromatics, 5H); 7.05 (d, J=8.3 Hz, 2H).
IR (neat) cm$^{-1}$: 3450 (br), 2926, 1740, 1611, 1515.
Mass m/z (CI): 431 (M+1).

EXAMPLE 71

(2S)-3-[4-{3-(2-methyl-7-fluoro-3,4-dihydro-2H-benzo[b][1,4]oxazin-4-yl)propylamino}phenyl]-2-methoxypropanoic acid

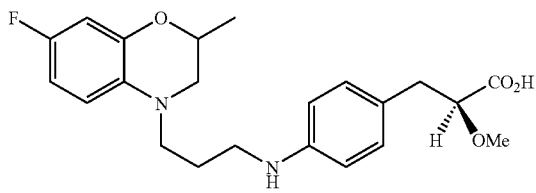

Ethyl (2S)-3-[4-{3-(2-methyl-7-fluoro-3,4-dihydro-2H-benzo[b][1,4]oxazin-4-yl)propylamino}phenyl]-2-methoxypropanoate (380 mg, 1 eq, 0.88 mmol), obtained in example 70, was hydrolyzed following the procedure of example 53, to obtain the title compound (150 mg, yield 43%) as viscous liquid.

$^1$H NMR (200 MHz, CDCl$_3$) δ: 1.37 (d, J=6.2 Hz, 3H); 1.80-2.00 (m, 2H), 2.90-3.60 (m, 13H); 3.98 (dd, J=7.0, 4.3 Hz, 1H), 4.18-4.35 (m, 1H), 6.55-6.70 (aromatics, 5H); 7.10 (d, J=8.0 Hz, 2H).

IR (KBr) cm$^{-1}$: 3400 (br), 2930, 1729, 1614, 1513.

Mass m/z (ES): 403.3 (M+1), 805.5 (M$_2$+1).

EXAMPLE 72

(2S)-3-[4-{3-(2-methyl-7-fluoro-3,4-dihydro-2H-benzo[b][1,4]oxazin-4-yl)propylamino}phenyl]-2-methoxypropanoic acid magnesium salt

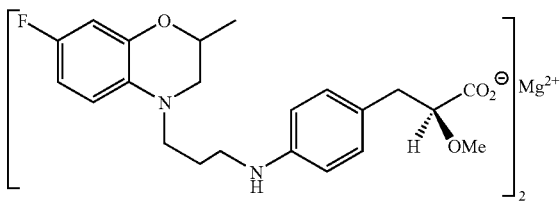

From (2S)-3-[4-{3-(2-methyl-7-fluoro-3,4-dihydro-2H-benzo[b][1,4]oxazin-4-yl)propylamino}phenyl]-2-ethoxypropanoic acid (150 mg, 1.0 eq, 0.37 mmol), obtained in example 71, and Mg(OMe)$_2$ (16 mg, 0.5 eq, 0.185 mmol) the desired salt as a powdery solid (quantitative yield) following the procedure of example 54.

Mp: 208-210° C.

The compounds of the present invention lowered random blood sugar level, triglyceride, total cholesterol, LDL, VLDL and increased HDL. This was demonstrated by in vitro as well as in vivi animal experiments.

Demonstration of Efficacy of Compounds

A) In Vitro:

a) Determination of hPPARα Activity

Ligand binding domain of hPPARα was fused to DNA binding domain of Yeast transcription factor Gal 4 in eucaryotic expression vector. Using superfect (Qiagen, Germany) as transfecting reagent HEK-293 cells are transfected with this plasmid and a reporter plasmid harboring the luciferace gene driven by a GAL4 specific promoter. Compound can be added at different concentrations after 42 hrs of transfection and incubated overnight. Luiciferase activity as a function of compound binding/activation capacity of PPARα will be measured using Packard Luclite kit (Packard, USA) in Top Count (Ivan Sadowsi, Brendan Bell, Peter Broag and Melvyn Hollis. Gene. 1992. 118: 137-141; Superfect Transfetion Reagent Handbook February 1997. Qiagen, Germany.

b) Determination of hPPARγ Activity

Ligand binding domain of hPPARγ is fused to DNA binding domain of Yeast transcription factor GAL4 in eucaryotic expression vector. Using lipofectamine (Gibco BRL, USA) as transfecting reagent HEK-293 cells are transfected with this plasmid and a reporter plasmid harboring the luciferase gene driven by a GAL4 specific promoter. Compound can be added at 1 μM concentration after 48 hrs of transfection and incubated overnight Luciferase activity as a function of drug binding/activation capacity of PPARγ1 will be measured using Packard Luclite kit (Packard, USA) in Packard Top Cout (Ivan Sadowski, Brendan Bell, Peter Broag and Melvyn Hollis. Gene. 1992. 118: 137-141; Guide to Eukaryotic Transfections with Cationic Lipid Reagents. Life Technologies, GIBCO BRL, USA).

| Example No | Concentration | PPARα | Concentration | PPARγ |
|---|---|---|---|---|
| 3 | 50 μM | 4.7 | 1 μM | 3.0 |
| 9 | 50 μM | 4.6 | 1 μM | 6.2 |
| 18 | 50 μM | 4.4 | 1 μM | 1.2 |
| 23 | 50 μM | 4.2 | 1 μM | 4.4 |
| 27 | 50 μM | 4.3 | 1 μM | 3.5 | c) Determination of HMG CoA Reductase Inhibition Activity

Liver microsome bound reductase is prepared from 2% cholestyarmine fed rats at mid-dark cycle. Spectrophotometric assays are carried out in 100 mM KH$_2$PO$_4$, 4 mM DTT, 0.2 mM NADPH, 0.3 mM HMG CoA and 125 μg of liver microsomal enzyme. Total reaction mixture volume was kept as 1 ml. Reaction was started by addition of HMG CoA. Reaction mixture is incubated at 37° C. for 30 min and decrease in absorbance at 340 nm was recorded. Reaction mixture without substrate was used as blank (Goldstein, J. L and Brown, M. S. Progress in understanding the LDL receptor and HMG CoA reductase, two membrane proteins that regulate the plasma cholesterol. J. Lipid Res. 1984, 25: 1450-1461). The test compounds will inhibit the HMG CoA reductase enzyme.

B) In Vivo a) Efficacy in Genetic Models

Mutation in colonies of laboratory animals and different sensitivities to dietary regimens have made the development of animal models with non-insulin dependent diabetes and hyperlipidemia associated with obesity and insulin resistance possible. Genetic models such as db/db and ob/ob (Diabetes, (1982) 31(1): 1-6) mice and zucker fa/fa rats have been developed by the various laboratories for understanding the pathophysiology of disease and testing the efficacy of new antidiabetic compounds (Diabetes, (1983) 32: 830-838; Annu. Rep. Sankyo Res. Lab. (1994). 46: 1-57). The homozygous animals, C57 BL/KsJ-db/db mice developed by Jackson Laboratory, US, are obese, hyperglycemic, hyperinsulinemic and insulin resistant (J. Clin. Invest., (1990) 85 : 962-967), whereas heterozygous are lean and normoglycemic. In db/db model, mouse progressively develops insulinopenia with age, a feature commonly observed in late stages of human type II diabetes when blood sugar levels are insufficiently controlled. The state of pancreas and its course vary according to the models. Since this model resembles that of type II diabetes mellitus, the compounds of the present invention will be tested for blood sugar and triglycerides lowering activities.

Male C57BL/KsJ-db/db mice of 8 to 14 weeks age, having body weight range of 35 to 60 grams, bred at Dr. Reddy's Research Foundation (DRF) animal house, were used in the experiment. The mice are provided with standard feed (National Institute of Nutrition (NIN), Hyderabad, India) and acidified water, ad libitum. The animals having more than 350 mg/dl blood sugar will be used for testing. The number of animals in each group was 4.

Test compounds are suspended on 0.25% carboxymethyl cellulose and administered to test group at a dose of 0.1 mg to 30 mg/kg through oral gavage daily for 6 days. The control group receives vehicle (dose 10 ml/kg). On 6th day the blood samples will be collected one hour after administration of test compounds/vehicle for assessing the biological activity.

The random blood sugar and triglyceride levels can be measured by collecting blood (100 μl) through orbital sinus, using heparinised capillary in tubes containing EDTA which was centrifuged to obtain plasma. The plasma glucose and triglyceride levels can be measured spectrometrically, by glucose oxidase and glycerol-3-$PO_4$ oxidase/peroxidse enzyme (Dr. Reddy's Lab. Diagnostic Division Kits, Hyderabad, India) methods respectively.

The blood sugar and triglycerides lowering activities of the test compound are calculated according to the formula.

No adverse effects were observed for any of the mentioned compounds of invention in the above test.

| Compound | Dose (mg/kg) | Reduction in Blood Glucose Level (%) | Triglyceride Lowering (%) |
|---|---|---|---|
| 3 | 3 | 33 | 29 |
| 18 | 3 | 16 | 35 |

The ob/ob mice were obtained at 5 weeks of age from Bornholtgard, Denmark and were used at 8 weeks of age. Zucker fa/fa fatty rats were obtained from IffaCredo, France at 10 weeks of age and were used at 13 weeks of age. The animals were maintained under 12 hour light and dark cycle at 25±1° C. Animals were given standard laboratory chow (NIN, Hyderabad, India) and water, ad libiturn (Fujiwara, T., Yoshioka, S., Yoshioka, I., Ushiyama, I and Horikoshi, H. Characterization of new oral anitidiabetic agent CS-045. Studies in KK and ob/ob mice and Zucker fatty rats. Diabetes. 1988. 37: 1549-1558).

The test compounds were administered at 0.1 to 30 mg/kg dose for 9 days. The control animals received the vehicle (0.25% carboxymethylcelllose, dose 10 mL/kg) through oral gavage.

The blood samples were collected in fed state 1 hour after drug administration on 0 and 9 day of treatment The blood was collected from the retro-orbital sinus through heparinised capillary in EDTA containing tubes. After centrifugation, plasma sample was separated for triglyceride, glucose, free fatty acid, total cholesterol and insulin estimations. Measurement of plasma triglyceride, glucose, total cholesterol was done using commercial kits (Dr. Reddy's Laboratory, Diagnostic Division, India). The plasma free fatty acid was measured using a commercials kit from Boehringer Mannheim, Germany. The plasma insulin was measured using a RIA kit (BARC, India). The reduction of various parameters examined are calculated according to the formula given below.

In ob/ob mice oral glucose tolerance test was performed after 9 days treatment. Mice were fasted for 5 hrs and challenged with 3 gm/kg of glucose orally. The blood samples were collected at 0, 15, 30, 60 and 120 min for estimation of plasma glucose levels.

The experimental results from the db/db mice, ob/ob mice, Zucker falfa rats suggest that the novel compounds of the present invention also possess therapeutic utility as a prophylactic or regular treatment for diabetes, obesity, cardiovascular disorders such as hypertension, hyperlipidaemia and other diseases; as it is known from the literature that such diseases are interrelated to each other.

Blood glucose level and triglycerides are also lowered at doses greater than 10 mg/kg. Normally, the quantum of reduction is dose dependent and plateaus at certain dose.

b) Plasma Triglyceride and Cholesterol Lowering Activity in Hypercholesterolemic Rat Models Male Sprague Dawley rats (NIN stock) were bred in DRF animal house. Animals were maintained under 12 hour light and dark cycle at 25±1° C. Rats of 180-200 gram body weight range were used for the experiment. Animals are made hypercholesterolemic by feeding 2% cholesterol and 1% sodium cholate mixed with standard laboratory chow [National Institute of Nutrition (NIN), Hyderabad, India] 30 for 6 days. Throughout the experimental period the animals were maintained on the same diet (Petit, D., Bonnefis, M. T., Rey, C and Infante, R. Effects of ciprofibrate on liver lipids and lipoprotein synthesis in normo- and hyperlipidemic rats. Atherosclerosis. 1988. 74 : 215-225).

The test compounds can be administered orally at a dose 0.1 to 30 mg/kg/day for 3 days. Control group was treated with vehicle alone (0.25% Carboxymethylcellulose; dose 10 ml/kg).

The blood samples were collected in fed state 1 hour after drug administration on 0 and 3 day of compound treatment. The blood was collected from the retro-orbital sinus through heparinsed capillary in EDTA containing tubes. After centrifugation, plasma sample was separated for total cholesterol, HDL and triglyceride estimations. Measurement of plasma, triglyceride, total cholesterol and HDL are were done using commercial kits (Dr. Reddy's Laboratory, Diagnostic Division, India). LDL and VLDL cholesterol were calculated from the data obtained for total cholesterol, HDL and triglyceride. The reduction of various parameters examined are calculated according to the formula.

| Example No. | Dose mg/kg | Triglyceride (%) ↓ | Total Cholesterol (%) ↓ | HDL (%) ↑ | LDL (%) ↓ | VLDL (%) ↓ |
|---|---|---|---|---|---|---|
| 3 | 10 | 77 | 69 | 254 | 80 | 77 |
| 3 | 10 | 77 | 64 | 260 | 74 | 77 |

↓ reduction; ↑ increase c) Plasma Triglyceride and Total Cholesterol Lowering Activity in Swiss Albino Mice and Gunie Pigs Male Swiss albino mice (SAM) and male Guinea pigs were obtained from NIN and housed in DRF animal house. All these animals are maintained under 12 hour light and dark cycle at 25±1° C. Animals were given standard laboratory chow (NIN, Hyderabad, India) and water, ad libitum.

SAM of 20-25 g body weight range and Guinea pigs of 500-760 g body weight range are used (Oliver, P., Plancke, M. O., Marzin, D., Clavey, V., Sauzieres, J and Fruchatt, J. C. Effects of fenofibrate, gemfibrozil and nicotinic acid on plasma lipoprotein levels in normal and hyperlipidemic mice. Atherosclerosis. 1988. 70 : 107-114).

The test compounds were administered orally to Swiss albino mice at 0.3 to 30 mg/kg/day dose for 6 days. Control mice are treated with vehicle (0.25% Carboxymethylcellulose; dose 10 ml/kg). The test compounds are administered orally to Guinea pigs at 0.3 to 30 mg/kg/day dose for 6 days. Control animals are treated with vehicle (0.25% Carboxymethylcellulose; dose 5 ml/kg).

The blood samples were collected in fed state 1 hour after drug administration on 0 and 6 day of treatment The blood was collected from the retro-orbital sinus through heparinised capillary in EDTA containing tubes. After centrifugation, plasma sample was separated for triglyceride and total cholesterol (Wieland, O. Methods of Enzymatic analysis. Bergermeyer, H. O., Ed., 1963. 211-214; Trinder, P. Ann. Clin. Biochem. 1969. 6: 24-27). Measurement of plasma triglyceride were done using commercial kits (Dr. Reddy's Diagnostic Division, Hyderabad, India).

| Compound | Dose (mg/kg) | Triglyceride Lowering (%) |
|---|---|---|
| 3 | 10 | 70 |
| 6 | 10 | 27 |
| 15 | 10 | 43 |
| 18 | 10 | 61 | d) Body Weight Reducing Effect in Cholesterol Fed Hamsters:

Male Syrian Hamsters were procured from NIN, Hyderabad, India. Animals were housed at DRF animal house under 12 hour light and dark cycle at 25±1° C. with free access to food and water. Animals are maintained with 1% cholesterol containing standard laboratory chow (NIN) from the day of treatment.

The test compounds can be administered orally at 1 to 30 mg/kg/day dose for 15 days. Control group animals were treated with vehicle (Mill Q water, dose 10 ml/kg/day). Body weights are measured on every $3^{rd}$ day.

Formulae for Calculation:

1. Percent reduction in Blood sugar/triglycerides/total cholesterol will be calculated according to the formula:

$$\text{Percent reduction (\%)} = \left[1 - \frac{TT/OT}{TC/OC}\right] \times 100$$

OC=Zero day control group value
OT=Zero day treated group value
TC=Test day control group value
TT=Test day treated group value 2. LDL and VLDL cholesterol levels will be calculated according to the formula:

$$\text{LDL cholesterol in mg/dl} = \left[\text{Total cholesterol} - \text{HDL cholesterol} - \frac{\text{Triglyceride}}{5}\right] \text{mg/dl}$$

VLDL cholesterol in mg/dl=[Total cholesterol−HDL cholesterol−LDL cholesterol]mg/dl.

We claim:

1. A compound of formula (I)

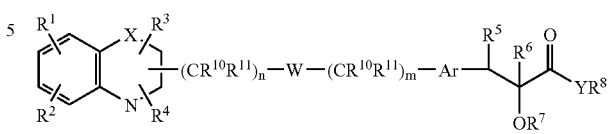

(I)

its tautomeric forms, its stereoisomers, its pharmaceutically acceptable salts, or its pharmaceutically acceptable solvates wherein $R^1$, $R^2$ and $R^3$, $R^4$ when attached to the carbon atom, are the same or different and represent hydrogen, halogen, hydroxy, nitro, cyano, formyl or a a group selected from alkyl, cycloalkyl, alkoxy, cycloalkoxy, aryl, aryloxy, aralkyl, aralkoxy, heterocyclyl, heteroaryl, heteroaralkyl, heteroaryloxy, heteroaralkoxy, acyloxy, hydroxyalkyl, amino, acylamino, monoalkylamino, dialkylamino, arylamino, aralkylamino, alkoxycarbonyl, aryloxycarbonyl, aralkoxycarbonyl, alkoxyalkyl, aryloxyalkyl, aralkoxyalkyl, alkylthio, thioalkyl, alkoxycarbonylamino, aryloxycarbonylamino, aralkoxycarbonylamino, carboxylic acid or its derivatives, or sulfonic acid or its derivatives, one or both of $R^3$ and $R^4$ represents oxo or thioxo group attached to carbon atom; $R^3$ and $R^4$ when attached to a nitrogen atom represent hydrogen, hydroxy, formyl or a group selected from alkyl, cycloalkyl, alkoxy, cycloalkoxy, aryl, aralkyl, heterocyclyl, heteroaryl, heteroaralkyl, acyloxy, hydroxyalkyl, amino, acylamino, monoalkylamino, dialkylamino, arylamino, aralkylamino, aminoalkyl, aryloxy, aralkoxy, heteroaryloxy, heteroaralkoxy, alkoxycarbonyl, aryloxycarbonyl, aralkoxycarbonyl, alkoxyalkyl, aryloxyalkyl, aralkoxyalkyl, alkylthio, thioalkyl groups, carboxylic acid derivatives, or sulfonic acid derivatives; X is oxygen; W represents $NR^{12}$, $-C(=O)-(CR^{10}R^{11})_o NR^{12}$, or $-O\text{-aryl-}(CR^{10}R^{11})_o NR^{12}$, where $R^{12}$ represents hydrogen or a group selected from alkyl, aryl or aralkyl group; o is an integer of from 0 to 6; $R^{10}$ and $R^{11}$ are same or different and represent hydrogen or a group selected from alkyl, alkoxy, aryl or aralkyl group; Ar represents a divalent single or fused aromatic or heterocyclic group selected from divalent phenylene, naphthylene, pyrrolyl, pyridyl, quinolinyl, benzofuryl, dihydrobenzofuryl, benzopyranyl, dihydrobenzopyranyl, indolyl, indolinyl, azaindolyl, azaindolinyl, pyrazolyl, benzothiazolyl or benzoxazolyl; $R^5$ represents hydrogen atom, hydroxy, alkoxy, halogen, alkyl, aralkyl group or forms a bond together with the adjacent group $R^6$; $R^6$ represents hydrogen, hydroxy, alkoxy, halogen, alkyl group, aralkyl or $R^6$ forms a bond together with $R^5$; $R^7$ represents hydrogen or a group selected from alkyl, cycloalkyl, aryl, aralkyl, alkoxyalkyl, alkoxycarbonyl, aryloxycarbonyl, alkylaminocarbonyl, arylaminocarbonyl, heterocyclyl, heteroaryl, or heteroaralkyl $R^8$ represents hydrogen or a group selected from alkyl, cycloalkyl, aryl, aralkyl, heterocyclyl, heteroaryl or heteroaralkyl; Y represents oxygen, sulfur or $NR^9$, where $R^9$ represents hydrogen or a group selected from alkyl, aryl, hydroxyalkyl, aralkyl heterocyclyl, heteroaryl, or heteroaralkyl or $NR^9$ represents chiral amine, or a chiral amine alcohol derived from a chiral amino acid; and m and n are integers from 0 to 6.

2. A compound according to claim 1, wherein when $R^1$, $R^2$, $R^3$ or $R^4$ are substituted the substituents are selected from halogen, hydroxyl, nitro, thio or groups selected from alkyl, cycloalkyl, alkoxy, cycloalkoxy, aryl, aralkyl, aryloxy, aralkoxy, alkoxyalkyl, aryloxyalkyl, arolkoxyalkyl, heterocyclyl, heteroaryl, heteroaralkyl, acyloxy, hydroxyalkyl, amino, acylamino, arylamino, aminoalkyl, alkoxycarbonyl, alkylamino, alkylthio groups, carboxylic acid or its derivatives or sulfonic acid or its derivatives.

3. A compound according to claim 1, wherein $R^1$, $R^2$, $R^3$, or $R^4$ when attached to the carbon atom, are the same or different and represent hydrogen, halogen or alkyl; or one or both of $R^3$ and $R^4$ represent oxo or thioxo group when attached to a carbon atom; or one or both of $R^3$ and $R^4$ when attached to nitrogen atom represent hydrogen or alkyl; $R^5$ represents a hydrogen atom or forms a bond together with the adjacent group $R^6$; $R^6$ represents hydrogen or forms a bond together with $R^5$; $R^7$ represents hydrogen alkyl, aryl or aralkyl; $R^5$ represents hydrogen or groups selected from alkyl, aryl or aralkyl; and m and n are integers from 0 to 2.

4. A compound according to claim 1, which is selected from the group consisting of:
- (±) Ethyl 3-[4-{3(3-(3,4-dihydro-2H-benzo[b][1,4]oxazin-4-yl)propylamino}phenyl]-2-ethoxypropanoate;
- (+) Ethyl 3-[4-{3-(3,4-dihydro-2H-benzo[b][1,4]oxazin-4-yl)propylamino}phenyl]-2-ethoxypropanoate;
- (−) Ethyl 3-[4-{3-(3,4-dihydro-2H-benzo[b][1,4]oxazin-4-yl)propylamino}phenyl]-2-ethoxypropanoate;
- (±) 3-[4-{3-(3,4-Dihydro-2H-benzo[b][1,4]oxazin-4-yl)propylamino}phenyl]-2-ethoxypropanoic acid or its salts;
- (+) 3-[4-{3-(3,4-Dihydro-2H-benzo[b][1,4]oxazin-4-yl)propylamino}phenyl]-2-ethoxypropanoic acid or its salts;
- (−) 3-[4-{3-(3,4-Dihydro-2H-benzo[b][1,4]oxazin-4-yl)propylamino}phenyl]-2-ethoxypropanoic acid or its salts;
- (±) Ethyl-[4-N-heptyl-N-{2-(3-oxo-3,4-dihydro-2H-benzo[b][1,4]oxazin-4-yl)ethylamino}phenyl]-2-ethoxypropanoate;
- (+) Ethyl 3-[4-N-heptyl-N-{2-(3-oxo-3,4-dihydro-2H-benzo[b][1,4]oxazin-4-yl)ethylamino}phenyl]-2-ethoxypropanoate;
- (−) Ethyl 3-[4-N-heptyl-N-{2-(3-oxo-3,4-dihydro-2H-benzo[b][1,4]oxazin-4-yl)ethylamino}phenyl]-2-ethoxypropanoate;
- (±) 3-[4-N-Heptyl-N-{2-(3-oxo-3,4-dihydro-2H-benzo[b][1,4]oxazin-4-yl)ethylamino}phenyl]-2-ethoxypropanoic acid or its salts;
- (+) 3-[4-N-Heptyl-N-{2-(3-oxo-3,4-dihydro-2H-benzo[b][1,4]oxazin-4-yl)ethylamino}phenyl]-2-ethoxypropanoic acid or its salts;
- (−) 3-[4-N-Heptyl-N-{2-(3-oxo-3,4-dihydro-2H-benzo[b][1,4]oxazin-4-yl)ethylamino}phenyl]-2-ethoxypropanoic acid or its salts;
- (±) Methyl 2-ethoxy-3-[4-{N-heptyl-N-(2-(3,4-dihydro-2H-benzo[b]oxazin-4-yl)-2-oxoethyl)aminomethyl}phenyl]propanoate;
- (+) Methyl 2-ethoxy-3-[4-{N-heptyl-N-(2-(3,4-dihydro-2H-benzo[b]oxazin-4-yl)-2-oxoethyl)aminomethyl}phenyl]propanoate;
- (−) Methyl 2-ethoxy-3-[4-{N-heptyl-N-(2-(3,4-dihydro-2H-benzo[b]oxazin-4-yl)-2-oxoethyl)aminomethyl}phenyl]propanoate;
- (±) 2-Ethoxy-3-[4-{N-heptyl-N-(2-(3,4-dihydro-2H-benzo[b]oxazin-4-yl)-2-oxoethyl)aminomethyl}phenyl]propanoic acid or its salts;
- (+) 2-Ethoxy-3-[4-{N-heptyl-N-(2-(3,4-dihydro-2H-benzo[b]oxazin-4-yl)-2-oxoethyl)aminomethyl}phenyl]propanoic acid or its salts;
- (−) 2-Ethoxy-3-[4-{N-heptyl-N-(2-(3,4-dihydro-2H-benzo[b]oxazin-4-yl)-2-oxoethyl)aminomethyl}phenyl]propanoic acid or its salts;
- (±) Methyl 3-[4-{5-(3,4-dihydro-2H-benzo[b][1,4]oxazin-4-yl)-5-oxopentylamino}phenyl]-2-ethoxypropanoate;
- (+) Methyl 3-[4-{5-(3,4-dihydro-2H-benzo[b][1,4]oxazin-4-yl)-5-oxopentylamino}phenyl]-2-ethoxypropanoate;
- (−) Methyl 3-[4-{5-(3,4-dihydro-2H-benzo[b][1,4]oxazin-4-yl)-5-oxopentylamino}phenyl]-2-ethoxypropanoate;
- (±) 3-[4-{5-(3,4-Dihydro-2H-benzo[b][1,4]oxazin-4-yl)-5-oxopentylamino}phenyl]-2-ethoxypropanoic acid ox its salts;
- (+) 3-[4-{5-(3,4-Dihydro-2H-benzo[b][1,4]oxazin-4-yl)-5-oxopentylamino}phenyl]-2-ethoxypropanoic acid or its salts;
- (−) 3-[4-{5-(3,4-Dihydro-2H-benzo[b][1,4]oxazin-4-yl)-5-oxopentylamino}phenyl]-2-ethoxypropanoic acid or its salts;
- (±) Methyl 3-[3-{3-(3,4-dihydro-2H-benzo[b][1,4]oxazin-4-yl)propylamino}phenyl]-2-ethoxypropanoate;
- (+) Methyl 3-[3-{3-(3,4-dihydro-2H-benzo[b][1,4]oxazin-4-yl)propylamino}phenyl]-2-ethoxypropanoate;
- (−) Methyl 3-[3-{3-(3,4-dihydro-2H-benzo[b][1,4]oxazin-4-yl)propylamino}phenyl]-2-ethoxypropanoate;
- (±) 3-[3-{3-(3,4-Dihydro-2H-benzo[b][1,4]oxazin-4-yl)propylamino}phenyl]-2-ethoxypropanoic acid or its salts;
- (+) 3-[3-{3-(3,4-Dihydro-2H-benzo[b][1,4]oxazin-4-yl)propylamino}phenyl]-2-ethoxypropanoic acid or its salts;
- (−) 3-[3-{3-(3,4-Dihydro-2H-benzo[b][1,4]oxazin-4-yl)propylamino}phenyl]-2-ethoxypropanoic acid or its salts;
- (±) Methyl 3-[4-{3-(7-fluoro-3,4-dihydro-2H-benzo[b][1,4]oxazin-4-yl)propylamino}phenyl]-2-ethoxypropanoate;
- (+) Methyl 3-[4-{3-(7-fluoro-3,4-dihydro-2H-benzo[b][1,4]oxazin-4-yl)propylamino}phenyl]-2-ethoxypropanoate;
- (−) Methyl 3-[4-{3-(7-fluoro-3,4-dihydro-2H-benzo[b][1,4]oxazin-4-yl)propylamino}phenyl]-2-ethoxypropanoate;
- (±) 3-[4-{3-(7-Fluoro-3,4-dihydro-2H-benzo[b][1,4]oxazin-4-yl)propylamino}phenyl]-2-ethoxypropanoic acid or its salts;
- (+) 3-[4-{3-(7-Fluoro-3,4-dihydro-2H-benzo[b][1,4]oxazin-4-yl)propylamino}phenyl]-2-ethoxypropanoic acid ox its salts;
- (−) 3-[4-{3-(7-Fluoro-3,4-dihydro-2H-benzo[b][1,4]oxazin-4-yl)propylamino}phenyl]-2-ethoxypropanoic acid or its salts,
- (±) Methyl 2-ethoxy-3-[4-{4-(3-(3,4-dihydro-2H-benzo[b][1,4]oxazin-4-yl)propyloxy)benzyl}aminophenyl]propanoate;
- (+) Methyl 2-ethoxy-3-[4-{4-(3-(3,4-dihydro-2H-benzo[b][1,4]oxazin-4-yl)propyloxy)benzyl}aminophenyl]propanoate;
- (−) Methyl 2-ethoxy-3-[4-{4-(3-(3,4-dihydro-2H-benzo[b][1,4]oxazin-4-yl)propyloxy)benzyl}aminophenyl]propanoate;
- (±) Methyl 2-ethoxy-3-[3-{4-(3-(3,4-dihydro-2H-benzo[b][1,4]oxazin-4-yl)propyloxy)benzyl}aminophenyl]propanoate;
- (+) Methyl 2-ethoxy-3-[3-{4-(3-(3,4-dihydro-2H-benzo[b][1,4]oxazin-4-yl)propyloxy)benzyl}aminophenyl]propanoate;

(−) Methyl 2-ethoxy-3-[3-{4-(3-(3,4-dihydro-2H-benzo[b][1,4]oxazin-4-yl)propyloxy)benzyl}aminophenyl]propanoate;

(±) 2-Ethoxy-3-[4-{4-(3-(3,4-dihydro-2H-benzo[b][1,4]oxazin-4-yl)propyloxy)benzyl}aminophenyl]propanoic acid or its salts;

(+) 2-Ethoxy-3-[4-{4-(3-(3,4-dihydro-2H-benzo[b][1,4]oxazin-4-yl)propyloxy)benzyl}aminophenyl]propanoic acid or its salts;

(−) 2-Ethoxy-3-[4-{4-(3-(3,4-dihydro-2H-benzo[b][1,4]oxazin-4-yl)propyloxy)benzyl}aminophenyl]propanoic acid or its salts;

(±) 2-Ethoxy-3-[3-{4-(3-(3,4-dihydro-2H-benzo[b][1,4]oxazin-4-yl)propyloxy)benzyl}aminophenyl]propanoic acid or its salts;

(+) 2-Ethoxy-3-[3-{4-(3-(3,4-dihydro-2H-benzo[b][1,4]oxazin-4-yl)propyloxy)benzyl}aminophenyl]propanoic acid or its salts;

(−) 2-Ethoxy-3-[3-{4-(3-(3,4-dihydro-2H-benzo[b][1,4]oxazin-4-yl)propyloxy)benzyl}aminophenyl]propanoic acid or its salts;

(±) Ethyl 2-ethoxy-3-[4-{2-(3,4-dihydro-2H-benzo[b][1,4]oxazin-4-yl)ethylamino}phenyl]propanoate;

(+) Ethyl 2-ethoxy-3-[4-{2-(3,4-dihydro-2H-benzo[b][1,4]oxazin-4-yl)ethylamino}phenyl]propanoate;

(−) Ethyl 2-ethoxy-3-[4-{2-(3,4-dihydro-2H-benzo[b][1,4]oxazin-4-yl)ethylamino}phenyl]propanoate;

(±) 2-Ethoxy-3-[4-{2-(3,4-dihydro-2H-benzo[b][1,4]oxazin-4-yl)ethylamino}phenyl]propanoic acid or its salts;

(+) 2-Ethoxy-3-[4-{2-(3,4-dihydro-2H-benzo[b][1,4]oxazin-4-yl)ethylamino}phenyl]propanoic acid or its salts;

(−) 2-Ethoxy-3-[4-{2-(3,4-dihydro-2H-benzo[b][1,4]oxazin-4-yl)ethylamino}phenyl]propanoic acid or its salts;

(±) Methyl 2-ethoxy-3-[4-[4-{2-(3,4-dihydro-2H-benzo[b][1,4]oxazin-4-yl)ethoxy}phenylaminomethyl]phenyl]propanoate;

(+) Methyl 2-ethoxy-3-[4-[4-{2-(3,4-dihydro-2H-benzo[b][1,4]oxazin-4-yl)ethoxy}phenylaminomethyl]phenyl]propanoate;

(−) Methyl 2-ethoxy-3-[4-[4-{2-(3,4-dihydro-2H benzo[b][1,4]oxazin-4-yl)ethoxy}phenylaminomethyl]phenyl]propanoate;

(±) 2-Ethoxy-3-[4-[4-{2-(3,4-dihydro-2H-benzo[b][1,4]oxazin-4-yl)ethoxy}phenylaminomethyl]phenyl]propanoic acid or its salts;

(+) 2-Ethoxy-3-[4-[4-{2-(3,4-dihydro-2H-benzo[b][1,4]oxazin-4-yl)ethoxy}phenylaminomethyl]phenyl]propanoic acid or its salts;

(−) 2-Ethoxy-3-[4-[4-{2-(3,4-dihydro-2H-benzo[b][1,4]oxazin-4-yl)ethoxy}phenylaminomethyl]phenyl]propanoic acid or its salts;

(±) Ethyl 3-[4-{3-(7-fluoro-3,4-dihydro-2H-benzo[b][1,4]oxazin-4-yl)propylamino}phenyl]-2-ethoxypropanoate;

(+) Ethyl 3-[4-{3-(7-fluoro-3,4-dihydro-2H-benzo[b][1,4]oxazin-4-yl)propylamino}phenyl]-2-ethoxypropanoate;

(−) Ethyl 3-[4-{3-(7-fluoro-3,4-dihydro-2H-benzo[b][1,4]oxazin-4-yl)propylamino}phenyl]-2-ethoxypropanoate;

(±) Ethyl 3-[4-{3-(7-fluoro-3,4-dihydro-2H-benzo[b][1,4]oxazin-4-yl)propylamino}phenyl]-2-methoxypropanoate;

(+) Ethyl 3-[4-{3-(7-fluoro-3,4-dihydro-2H-benzo[b][1,4]oxazin-4-yl)propylamino}phenyl]-2-methoxypropanoate;

(−) Ethyl 3-[4-{3-(7-Fluoro-3,4-dihydro-2H-benzo[b][1,4]oxazin-4-yl)propylamino}phenyl]-2-methoxypropanoate;

(±) 3-[4-{3-(7-Fluoro-3,4-dihydro-2H-benzo[b][1,4]oxazin-4-yl)propylamino}phenyl]-2-methoxypropanoic acid or its salts;

(+) 3-[4-{3-(7-Fluoro-3,4-dihydro-2H-benzo[b][1,4]oxazin-4-yl)propylamino}phenyl]-2-methoxypropanoic acid or its salts;

(−) 3-[4-{3-(7-Fluoro-3,4-dihydro-2H-benzo[b][1,4]oxazin-4-yl)propylamino}phenyl]-2-methoxypropanoic acid ox its salts;

(±) Ethyl 3-[4-{3-(2-methyl-7-fluoro-3,4-dihydro-2H-benzo[b][1,4]oxazin-4-yl)propylamino}phenyl]-2-ethoxypropanoate;

(+) Ethyl 3-[4-{3-(2-methyl-7-fluoro-3,4-dihydro-2H-benzo[b][1,4]oxazin-4-yl)propylamino}phenyl]-2-ethoxypropanoate;

(−) Ethyl 3-[4-{3-(2-methyl-7-fluoro-3,4-dihydro-2H-benzo[b][1,4]oxazin-4-yl)propylamino}phenyl]-2-ethoxypropanoate;

(±) 3-[4-{3-(2-methyl-7-Fluoro-3,4-dihydro-2H-benzo[b][1,4]oxazin-4-yl)propylamino}phenyl]-2-ethoxypropanoic acid or its salts;

(+) 3-[4-{3-(2-methyl-7-Fluoro-3,4-dihydro-2H-benzo[b][1,4]oxazin-4-yl)propylamino}phenyl]-2-ethoxypropanoic acid or its salts;

(−) 3-[4-{3-(2-methyl-7-Fluoro-3,4-dihydro-2H-benzo[b][1,4]oxazin-4-yl)propylamino}phenyl]-2-ethoxypropanoic acid or its salts;

(±) Ethyl 3-[4-{3-(2-methyl-3,4-dihydro-2H-benzo[b][1,4]oxazin-4-yl)propylamino}phenyl]-2-ethoxypropanoate;

(+) Ethyl 3-[4-{3-(2-methyl-3,4-dihydro-2H-benzo[b][1,4]oxazin-4-yl)propylamino}phenyl]-2-ethoxypropanoate;

(−) Ethyl 3-[4-{3-(2-methyl-3,4-dihydro-2H-benzo[b][1,4]oxazin-4-yl)propylamino}phenyl]-2-ethoxypropanoate;

(±) 3-[4-{3-(2-methyl-3,4-dihydro-2H-benzo[b][1,4]oxazin-4-yl)propylamino}phenyl]-2-ethoxypropanoic acid or its salts;

(+) 3-[4-{3-(2-methyl-3,4-dihydro-2H-benzo[b][1,4]oxazin-4-yl)propylamino}phenyl]-2-ethoxypropanoic acid or its salts;

(−) 3-[4-{3-(2-methyl-3,4-dihydro-2H-benzo[b][1,4]oxazin-4-yl)propylamino}phenyl]-2-ethoxypropanoic acid or its salts;

(±) Ethyl 3-[4-{3-(2-methyl-3,4-dihydro-2H-benzo[b][1,4]oxazin-4-yl)propylamino}phenyl]-2-methoxypropanoate;

(+) Ethyl 3-[4-{3-(2-methyl-3,4-dihydro-2H-benzo[b][1,4]oxazin-4-yl)propylamino}phenyl]-2-methoxypropanoate;

(−) Ethyl 3-[4-{3-(2-methyl-3,4-dihydro-2H-benzo[b][1,4]oxazin-4-yl)propylamino}phenyl]-2-methoxypropanoate;

(±) 3-(4-{3-(2-methyl-3,4-dihydro-2H-benzo[b][1,4]oxazin-4-yl)propylamino}phenyl]-2-methoxypropanoic acid or its salts;

(+) 3-[4-{3-(2-methyl-3,4-dihydro-2H-benzo[b][1,4]oxazin-4-yl)propylamino}phenyl]-2-methoxypropanoic acid or its salts;

(−) 3-[4-{3-(2-methyl-3,4-dihydro-2H-benzo[b][1,4]oxazin-4-yl)propylamino}phenyl]-2-methoxypropanoic acid or its salts;

(±) Ethyl 3-[4-{3-(2-propyl-3,4-dihydro-2H-benzo[b][1,4]oxazin-4-yl)propylamino}phenyl]-2-ethoxypropanoate;

(+) Ethyl 3-[4-{3-(2-propyl-3,4-dihydro-2H-benzo[b][1,4]oxazin-4-yl)propylamino}phenyl]-2-ethoxypropanoate;

(−) Ethyl 3-[4-{3-(2-propyl-3,4-dihydro-2H-benzo[b][1,4]oxazin-4-yl)propylamino}phenyl]-2-ethoxypropanoate;

(±) 3-[4-{3-(2-propyl-3,4-dihydro-2H-benzo[b][1,4]oxazin-4-yl)propylamino}phenyl]-2-ethoxypropanoic acid or its salts;

(+) 3-[4-{3-(2-propyl-3,4-dihydro-2H-benzo[b][1,4]oxazin-4-yl)propylamino}phenyl]-2-ethoxypropanoic acid or its salts;

(−) 3-[4-{3-(2-propyl-3,4-dihydro-2H-benzo[b][1,4]oxazin-4-yl)propylamino}phenyl]-2-ethoxypropanoic acid or its salts;

(±) Ethyl(2S)-3-[4-{3-(2-propyl-3,4-dihydro-2H-benzo[b][1,4]oxazin-4-yl)propylamino}phenyl]-2-methoxypropanoate;

(+) Ethyl(2S)-3-[4-{3-(2-propyl-3,4-dihydro-2H benzo[b][1,4]oxazin-4-yl)propylamino}phenyl]-2-methoxypropanoate;

(−) Ethyl(2S)-3-[4-{3-(2-propyl-3,4-dihydro-2H-benzo[b][1,4]oxazin-4-yl)propylamino}phenyl]-2-methoxypropanoate;

(±) 3-[4-{3-(2-propyl-3,4-dihydro-2H-benzo[b][1,4]oxazin-4-yl)propylamino}phenyl]-2-methoxypropanoic acid and its salts;

(+) 3-[4-{3-(2-propyl-3,4-dihydro-2H-benzo[b][1,4]oxazin-4-yl)propylamino}phenyl]-2-methoxypropanoic acid and its salts;

(−) 3-[4-{3-(2-propyl-3,4-dihydro-2H-benzo[b][1,4]oxazin-4-yl)propylamino}phenyl]-2-methoxypropanoic acid and its salts;

(±) Ethyl 2-isopropoxy-3-[4-{3-(7-fluoro-3,4-dihydro-2H-benzo[b][1,4]oxazin-4-yl)propylamino)phenyl]propanoate;

(+) Ethyl 2-isopropoxy-3-[4-{3-(7-fluoro-3,4-dihydro-2H-benzo[b][1,4]oxazin-4-yl)propylamino)phenyl]propanoate;

(−) Ethyl 2-isopropoxy-3-[4-{3-(7-fluoro-3,4-dihydro-2H-benzo[b][1,4]oxazin-4-yl)propylamino)phenyl]propanoate;

(±) 2-Isopropoxy-3-[4-{3-(7-fluoro-3,4-dihydro-2H-benzo[b][1,4]oxazin-4-yl)propylamino}phenyl]propanoic acid and its salts;

(+) 2-Isopropoxy-3-[4-{3-(7-fluoro-3,4-dihydro-2H-benzo[b][1,4]oxazin-4-yl)propylamino}phenyl]propanoic acid and its salts;

(−) 2-Isopropoxy-3-[4-{3-(7-fluoro-3,4-dihydro-2H-benzo[b][1,4]oxazin-4-yl)propylamino}phenyl]propanoic acid and its salts;

(±) Ethyl 3-[4-{3-(2-methyl-7-fluoro-3,4-dihydro-2H-benzo[b][1,4]oxazin-4-yl)propylamino}phenyl]-2-methoxypropanoate;

(+) Ethyl 3-[4-{3-(2-methyl-7-fluoro-3,4-dihydro-2H-benzo[b][1,4]oxazin-4-yl)propylamino}phenyl]-2-methoxypropanoate;

(−) Ethyl 3-[4-{3-(2-methyl-7-fluoro-3,4-dihydro-2H-benzo[b][1,4]oxazin-4-yl)propylamino}phenyl]-2-methoxypropanoate;

(±)3-[4-{3-(2-methyl-7-fluoro-3,4-dihydro-2H-benzo[b][1,4]oxazin-4-yl)propylamino}phenyl]-2-methoxypropanoic acid and its salts;

(+) 3-[4-{3-(2-methyl-7-fluoro-3,4-dihydro-2H-benzo[b][1,4]oxazin-4-yl)propylamino}phenyl]-2-methoxypropanoic acid and its salts;

(−) 3-[4-{3-(2-methyl-7-fluoro-3,4-dihydro-2H-benzo[b][1,4]oxazin-4-yl)propylamino}phenyl]-2-methoxypropanoic acid and its salts;

[2S,N(1R)]-N-(2-hydroxy-1-phenylethyl)-2-ethoxy-3-[4-{3-(3,4-dihydro-2H-benzo[b][1,4]oxazin-4-yl) propylamino}phenyl]propanamide;

[2R,N(1R)]-N-(2-hydroxy-1-phenylethyl)-2-ethoxy-3-[4-{3-(3,4-dihydro-2H-benzo[b][1,4]oxazin-4-yl) propylamino}phenyl]propanamide;

2S,N(1R)]-N-(2-hydroxy-1-phenylethyl) 2-ethoxy-3-[4-{3-(7-fluoro-3,4-dihydro-2H-benzo[b][1,4]oxazin-4-yl)propylamino}phenyl]propanamide;

[2R,N(1R)]-N-(2-hydroxy-1-phenylethyl)-2-ethoxy-3-[4-{3-7-fluoro-3,4-dihydro-2H-benzo[b][1,4]oxazin-4-yl) propylamino}phenyl]propanamide;

[2S,N(1R)]-N-(2-hydroxy-1-phenylethyl)-2-ethoxy-3-[4-{3-(3,4-dihydro-2H-benzo[b][1,4]oxazin-4-yl) propylamino}phenyl]propanamide hydrochloride salt; and

[2R,N(1R)]-N-(2-hydroxy-1-phenylethyl)-2-ethoxy-3-[4-{3-(3,4-dihydro-2H-benzo[b][1,4]oxazin-4-yl) propylamino}phenyl]propanamide hydrochloride salt.

5. A compound according to claim 1, wherein the pharmaceutically acceptable salt is selected from the group consisting of Li, Na, K, Ca, Mg, Fe, Cu, Zn, Mn; NN'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or amino acids; guanidine, substituted guanidine wherein the substituents are selected from nitro, amino, alkyl, alkenyl, alkynyl, ammonium or ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, ketoglutarates, ammonium or ammonium salts or aluminium salt.

6. A pharmaceutical composition, which comprises a compound of formula (I) as defined in claim 1 and a pharmaceutically acceptable carrier, diluent, excipient or solvate.

7. The composition of claim 6, further including HMG CoA reductase inhibitor, fibrate, nicotinic acid, cholestyramine, cholestipol, probucol or combinations thereof.

8. A pharmaceutical composition, which comprises a compound of formula (I) as defined in claim 4 and a pharmaceutically acceptable carrier, diluent, excipient or solvate.

9. The composition of claim 8, further including HMG CoA reductase inhibitor, fibrate, nicotinic acid, cholestyramine, cholestipol, probucol or combination thereof.

10. A method of treating hyperlipemia, hypercholesteremia, hyperglycemia, osteoporosis, obesity, impaired glucose tolerance, atherosclerosis, leptin resistance, insulin resistance or a disease in which insulin resistance is the underlying pathophysiological mechanism comprising administering a compound of formula (I) as defined in claim 1 to a patient in need thereof.

11. The method according to claim 10, wherein the disease is type II diabetes, impaired glucose tolerance, dyslipidemia, Syndrome X, hypertension, obesity, insulin resistance, coronary artery disease, glomerulonephritis, glomeruloscierosis, nephrotic syndrome, hypertensive nephrosclerosis, psoriasis, polycystic ovarian syndrome (PCOS), dementia, inflammatory bowel disease, myotonic dystrophy, pancreatitis, arteriosclerosis, xanthoma, prostate cancer, colon cancer, rectum cancer or osteoporosis.

12. A method of treating hyperlipemia, hypercholesteremia, hyperglycemia, osteoporosis, obesity, impaired glucose tolerance, atherosclerosis, leptin resistance, insulin resistance or a disease in which insulin resistance is the underlying pathophysiological mechanism comprising administering a compound of formula (I) as defined in claim 4 to a patient in need thereof.

13. The method according to claim 12, wherein the disease is type II diabetes, impaired glucose tolerance, dyslipidemia, Syndrome X, hypertension, obesity, insulin resistance, coronary artery disease, glomerulonephritis, glomeruloscierosis, nephrotic syndrome, hypertensive nephrosclerosis, psoriasis, polycystic ovarian syndrome (PCOS), dementia, inflammatory bowel disease, myotonic dystrophy, pancreatitis, arteriosclerosis, xanthoma, prostate cancer, colon cancer, rectum cancer or osteoporosis.

14. A method of treating hyperlipemia, hypercholesteremia, hyperglycemia, osteoporosis, obesity, impaired glucose tolerance, atherosclerosis, leptin resistance, insulin resistance or a disease in which insulin resistance is the underlying pathophysiological mechanism comprising administering a compound of formula (I) as defined in claim 5 to a patient in need thereof.

15. The method according to claim 14, wherein the disease is type II diabetes, impaired glucose tolerance, dyslipidemia, Syndrome X, hypertension, obesity, insulin resistance, coronary artery disease, glomerulonephritis, glomeruloscierosis, nephrotic syndrome, hypertensive nephrosclerosis, psoriasis, polycystic ovarian syndrome (PCOS), dementia, inflammatory bowel disease, myotonic dystrophy, pancreatitis, arteriosclerosis, xanthoma, prostate cancer, colon cancer, rectum cancer or osteoporosis.

16. A method of treating hyperlipemia, hypercholesteremia, hyperglycemia, osteoporosis, obesity, impaired glucose tolerance, atherosclerosis, leptin resistance, insulin resistance or a disease in which insulin resistance is the underlying pathophysiological mechanism comprising administering a pharmaceutical composition as defined in claim 6 to a patient in need thereof.

17. The method according to claim 16, wherein the disease is type II diabetes, impaired glucose tolerance, dyslipidemia, Syndrome X, hypertension, obesity, insulin resistance, coronary artery disease, glomerulonephritis, glomeruloscierosis, nephrotic syndrome, hypertensive nephrosclerosis, psoriasis, polycystic ovarian syndrome (PCOS), dementia, inflammatory bowel disease, myotonic dystrophy, pancreatitis, arteriosclerosis, xanthoma, prostate cancer, colon cancer, rectum cancer or osteoporosis.

* * * * *